US010612026B2

(12) United States Patent
Lee et al.

(10) Patent No.: US 10,612,026 B2
(45) Date of Patent: Apr. 7, 2020

(54) PHARMACEUTICAL COMPOSITION FOR TREATING CANCER COMPRISING MICRORNA AS ACTIVE INGREDIENT

(71) Applicant: BIONEER CORPORATION, Daejeon (KR)

(72) Inventors: Taewoo Lee, Seoul (KR); Sanghyung Shim, Daejeon (KR); Ungsik Yu, Daejeon (KR); Han Oh Park, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 0 days.

(21) Appl. No.: 16/371,026

(22) Filed: Mar. 31, 2019

(65) Prior Publication Data

US 2019/0218555 A1 Jul. 18, 2019

Related U.S. Application Data

(62) Division of application No. 15/553,097, filed as application No. PCT/KR2016/001828 on Feb. 25, 2016, now Pat. No. 10,351,849.

(30) Foreign Application Priority Data

Feb. 25, 2015 (KR) ........................ 10-2015-0026557

(51) Int. Cl.

| C12N 15/113 | (2010.01) |
| A61K 48/00 | (2006.01) |
| A61K 31/7105 | (2006.01) |
| A61K 31/713 | (2006.01) |
| A61P 35/00 | (2006.01) |

(52) U.S. Cl.
CPC .......... *C12N 15/113* (2013.01); *A61K 31/713* (2013.01); *A61K 31/7105* (2013.01); *A61K 48/00* (2013.01); *A61P 35/00* (2018.01); *C12N 15/1138* (2013.01); *C12N 2310/141* (2013.01)

(58) Field of Classification Search
None
See application file for complete search history.

(56) References Cited

U.S. PATENT DOCUMENTS

| 2009/0227533 A1 | 9/2009 | Bader et al. |
| 2012/0302626 A1 | 11/2012 | Dave et al. |
| 2014/0080894 A1 | 3/2014 | Mcelligott |

FOREIGN PATENT DOCUMENTS

| CN | 103505743 A | 1/2014 |
| RU | 2476239 C2 | 2/2013 |
| WO | WO2014048441 A1 | 4/2014 |
| WO | 2014100252 A1 | 6/2014 |
| WO | WO2014078686 A1 | 5/2018 |

OTHER PUBLICATIONS

Wang, Z., et al., "miRNA Mimic Technology", "MicroRNA Interference Technologies", 2009, Page(s) DOI: 10.1007/978-3-642-00489-6_4,Publisher: Springer-Verlag Berline Heidelberg.
Tanaka, M., et al., "A Novel RNA-Binding Protein, Oss/C9orf10, Regulates Activity of Src Kinases to Protect Cells from Oxidative Stress-Induced Apoptosis", "Molecular and Cellular Biology", Jan. 2009, pp. 402-413, vol. 29, No. 2.
Tang, Y., et al., "Rapid induction of apoptosis during Kinesin-5 inhibitor-induced mitotic arrest in HL60 cells", "Cancer Letters", 2011, pp. 15-24, vol. 310.
Tanji, C., et al., "A-Kinase Anchoring Protein AKAP220 Binds to Glycogen Synthase Kinase-3b (GSK-3b) and Mediates Protein Kinase A-dependent Inhibition of GSK-3b", "The Journal of Biological Chemistry", Oct. 4, 2002, pp. 36955-36961, vol. 277, No. 40.
Tennakoon, S., et al., "The calcium-sensing receptor and the hallmarks of cancer", "Biochimica et Biophysica Acta", 2015, Page(s) http://dx.doi.org/10.1016/j.bbamcr.2015.11.017.
Tomari, Y., et al., "Perspective: machines for RNAi", "Genes & Development", 2005, pp. 517-529, vol. 19.
Ueno, K., et al., "Tumor Suppressor MicroRNA-493 Decreases Cell Motility and Migration Ability in Human Bladder Cancer Cells by Downregulating RhoC and FZD4", "Molecular Cancer Therapeutics", Jan. 2012, pp. 244-253, vol. 11, No. 1.
Van Rooij, E., et al., "Developing MicroRNA Therapeutics", "Circulation Research", 2012, pp. 496-507, vol. 110.
Venere, M., et al., "The mitotic kinesin KIF11 is a driver of invasion, proliferation, and self-renewal in glioblastoma", "Science Translational Medicine", Sep. 9, 2015, pp. 113; DOI: 10.1126/scitranslmed.aac6762, vol. 7, No. 304.
Whiting, J. L., et al., "Protein Kinase A Opposes the Phosphorylation-dependent Recruitment of Glycogen Synthase Kinase 3b to A-kinase Anchoring Protein 220", "The Journal of Biological Chemistry", Aug. 7, 2015, pp. 19445-19457, vol. 290, No. 32.
Wiggins, J. F., et al., "Development of a Lung Cancer Therapeutic Based on the Tumor Suppressor MicroRNA-34", "Cancer Research", Jul. 15, 2010, pp. 5923-5930, vol. 70, No. 14.
Zhang, L., et al., "Development of transcriptomic biomarker signature in human saliva to detect lung cancer", "Cellular and Molecular Life Sciences", Jun. 12, 2012, pp. 3341-3350, vol. 69.
Zhang, Q., et al., "Role of microRNA-30c Targeting ADAM19 in Colorectal Cancer", "PLoS One", Mar. 23, 2015, Page(s) DOI:10.1371/journal.pone.0120698, vol. 10, No. 3.

(Continued)

*Primary Examiner* — J. E Angell
(74) *Attorney, Agent, or Firm* — Hultquist, PLLC; Steven J. Hultquist

(57) ABSTRACT

The present invention relates to a pharmaceutical composition for treatment of cancer, which comprises, as an active ingredient, one or more miRNAs selected from the group consisting of miR-3670, miR-8078, and miR-4477a. The pharmaceutical composition for treatment of cancer according to the present invention exhibits excellent effects of inhibiting cancer cell proliferation and inducing cancer cell apoptosis. Thus, the pharmaceutical composition of the present invention can be effectively used as an anticancer therapeutic agent.

15 Claims, 3 Drawing Sheets
(2 of 3 Drawing Sheet(s) Filed in Color)
Specification includes a Sequence Listing.

(56) References Cited

OTHER PUBLICATIONS

Zheng, C., et al., "microRNA-195 functions as a tumor suppressor by inhibiting CBX4 in hepatocellular carcinoma", "Oncology Reports", 2015, pp. 1115-1122, vol. 33.
Agostini, M., et al., "miR-34: from bench to bedside", "Oncotarget", Apr. 21, 2014, pp. 872-881, vol. 5, No. 4.
Bartel, D. P., "MicroRNAs: Target Recognition and Regulatory Functions", "Cell", Jan. 23, 2009, pp. 215-233, vol. 136.
Bartolome, R. A., et al., "IL-13 receptor a2 signaling requires a scaffold protein, FAM120A, to activate the FAK and PI3K pathways in colon cancer metastatis", "Cancer Research", 2015, Page(s) DOI: 10.1158/0008-5472.CAN-14-3650.
Brodersen, P., et al., "Revisiting the principles of microRNA target recognition and mode of action", "Nature Reviews", Feb. 2009, pp. 141-148, vol. 10.
Burnett, J. C., et al., "RNA-Based Therapeutics: Current Progress and Future Prospects", "Chemistry & Biology", Jan. 27, 2012, pp. 60-71, vol. 19.
Calin, G. A., et al., "MicroRNA signatures in human cancers", "Nature Reviews", Nov. 2006, pp. 857-866 vol. 6.
Carthew, R. W., et al., "Origins and Mechanisms of miRNAs and siRNAs", "Cell", Feb. 20, 2009, pp. 342-655, vol. 136.
Chang, T.-C., et al., "Transactivation of miR-34a by p53 broadly influences gene expression and promotes apoptosis", "Molecular Cell", Jun. 8, 2007, pp. 745-752, vol. 26, No. 5.
Chu, C.-Y., et al., "Potent RNAi by short RNA triggers", "RNA", Jul. 24, 2008, pp. 1714-1719, vol. 24.
Dangwal, S., et al., "microRNA Therapeutics in Cardiovascular Disease Models", "Annual Review of Pharmacology and Toxicology", Sep. 17, 2013, p. 10.1-10.19, vol. 54.
Erez, A., et al., "Sil overexpression in lung cancer characterizes tumors with increased mitotic activity", "Oncogene", Apr. 26, 2004, pp. 5371-5377, vol. 23.
Erez, A., et al., "The SIL Gene Is Essential for Mitotic Entry and Survival of Cancer Cells", "Cancer Research", May 1, 2007, pp. 4022-4027, vol. 67, No. 9.
Fujii, M., et al., "SNIP1 Is a Candidate Modifier of the Transcriptional Activity of c-Myc on E Box-Dependent Target Genes", "Molecular Cell", Dec. 8, 2006, pp. 771-783, vol. 24.
Hermeking, H., "The miR-34 family in cancer and apoptosis", "Cell Death and Differentiation", May 22, 2009, pp. 193-199, vol. 17.
Huang, XD., et al., "Phosphorylation of Dishevelled by Protein Kinase RIPK4 Regulates Wnt Signaling", "Science Express", Jan. 31, 2013, pp. 17.
Iorns, E., et al., "Utilizing RNA interference to enhance cancer drug discovery", "Nature Reviews", Jul. 2007, pp. 556-568, vol. 6.
Jackson, A. L., et al., "Expression profiling reveals off-target gene regulation by RNAi", "Nature Biotechnology", Jun. 2003, pp. 635-637, vol. 21, No. 6.
Jackson, A. L., et al., "Position-specific chemical modification of siRNAs reduces off-target transcript silencing", "RNA", 2006, pp. 1197-1205, vol. 12.
Jackson, A. L., et al., "Widespread siRNA off-target transcript silencing mediated by seed region sequence complementarity", "RNA", 2006, pp. 1179-1187, vol. 12.
Jeon, H.-S., et al., "High expression of SNIP1 correlates with poor prognosis in Non-small cell lung cancer and SNIP1 interferes with the recruitment of HDAC1 to RB in vitro", "Lung Cancer", 2013, pp. 24-30, vol. 82.
Jiao, H.-K., et al., "Prognostic significance of Cbx4 expression and its beneficial effect for transarterial chemoembolization in hepatocellular carcinoma", "Cell Death and Disease", Mar. 12, 2015, pp. 19; doi:10.10381/cddis.2015.57, vol. 6, No. e1689.
Kota, J., et al., "Therapeutic microRNA Delivery Suppresses Tumorigenesis in a Murine Liver Cancer Model", "Cell", Jun. 12, 2009, pp. 1005-1017, vol. 137.
Landi D., et al., "Role of variations within microRNA-binding sites in cancer", "Mutagenesis", 2012, pp. 205-210, vol. 27, No. 2.
Laviolette, L. A., et al., "17b-Estradiol upregulates GREB1 and accelerates ovarian tumor progression in vivo", "International Journal of Cancer", 2014, pp. 1072-1084, vol. 135.
Li, M., et al., "MicroRNA-561 Promotes Acetaminophen-Induced Hepatotoxicity in Hepg2 Cells and Primary Human Hepatocytes through Down-Regulation of the Nuclear Receptor Co-Repressor Dosage-Sensitive Sex Reversal Adrenal Hypoplasia Congenital Critical Region on X Chromosom", "Drug Metabolism and Disposition", 2014, pp. 44-61; DOI: 10.1124/dmd.113.052670, vol. 42.
Li, Q., et al., "SNIP1: a new activator of HSE signaling pathway", "Molecular and Cellular Biochemistry", Oct. 22, 2011, pp. 16, vol. 362.
Li, Y., et al., "The HECTD3 E3 ubiquitin ligase facilitates cancer cell survival by promoting K63-linked polyubiquitination of caspase-8", "Cell Death and Disease", Nov. 28, 2013, pp. 1-11; doi:10.1038/cddis.2013.464, vol. 4, No. e935.
Li, Y., et al., "The HECTD3 E3 Ubiquitin Ligase Suppresses Cisplatin-Induced Apoptosis via Stabilizing MALT1", "Neoplasia", Jan. 2013, pp. 39-48, vol. 15, No. 1.
Liang, X., et al., "Hypoxia-inducible factor-1 alpha, in association with TWIST2 and SNIP1, is a critical prognostic factor in patients with tongue squamous cell carcinoma", "Oral Oncology", 2011, pp. 92-97, vol. 47.
Lin, Z.-Y., et al., "MicroRNA-224 inhibits progression of human prostate cancer by downregulating TRIB1", "International Journal of Cancer", 2014, pp. 541-550, vol. 135.
Liu, D., et al., "Identification of Aberrantly Expressed miRNAs in Gastric Cancer", "Gastroenterology Research and Practice", 2014, pp. 1-9.
Logue, J. S., et al., "AKAP220 Protein Organizes Signaling Elements That Impact Cell Migration", "The Journal of Biological Chemistry", Nov. 11, 2011, pp. 39269-39281, vol. 286, No. 45.
Ma, Z., et al., "MicroRNA-34a Inhibits the Proliferation and Promotes the Apoptosis of Non-Small Cell Lung Cancer H1299 Cell Line by Targeting TGF[beta]R2", "Tumor Biology", 2015, pp. 2481-2490, vol. 36.
MacFarlane, L.-A., et al., "MicroRNA: Biogenesis, Function and Role in Cancer", "Current Genomics", 2010, pp. 537-561, vol. 11.
Malone, C. D., et al., "Small RNAs as Guardians of the Genome", "Cell", 2009, pp. 656-668, vol. 136.
Martens-De Kemp, S. R., et al., "Functional Genetic Screens Identify Genes Essential for Tumor Cell Survival in Head and Neck and Lung Cancer", "Clinical Cancer Research", Apr. 15, 2013, pp. 1994-2003, vol. 19, No. 8.
Mashidori, T., et al., "Increased alpha-taxilin protein expression is associated with the metastatic and invasive potential of renal cell cancer", "Biomedical Research", 2011, pp. 103-110, vol. 32, No. 2.
Mittal, V., "Improving the Efficiency of RNA Interference in Mammals", "Nature Reviews", May 2004, pp. 355-365, vol. 5.
Nicoloso, M. S., et al., "MicroRNAs the micro steering wheel of tumour metastases", "Nature Reviews", Apr. 2009, pp. 293-302, vol. 9.
Nielsen, C. B., et al., "Determinants of targeting by endogenous and exogenous microRNAs and siRNAs", "RNA", 2007, pp. 1894-1910, vol. 13.
Ohashi, K., et al., "Characteristics of Lung Cancers Harboring NRAS Mutations", "Clinical Cancer Research", Mar. 20, 2013, pp. 2584-2591, vol. 19.
Ohtomo, N., et al., "Expression of -taxilin in hepatocellular carcinoma correlates with growth activity and malignant potential of the tumor", "International Journal of Oncology", 2010, pp. 1417-1423, vol. 37.
Orouji, E., et al., "MAP kinase pathway gene copy alterations in NRAS/BRAF wild-type advanced melanoma", "International Journal of Cancer", Dec. 18, 2015, pp. 2257-2262, vol. 138.
Pecina-Slaus, N., et al., "Wnt signaling transcription factors TCF-1 and LEF-1 are upregulated in malignant astrocytic brain tumors", "Histology and Histopathology", 2014, pp. 1557-1564, vol. 29, No. 12.
Peek, A. S., et al., "Design of active small interfering RNAs", "Current Opinion in Molecular Therapeutics", 2007, pp. 110-118, vol. 9, No. 2.

(56) References Cited

OTHER PUBLICATIONS

Rae, J. M., et al., "GREB1 is a Novel Androgen-Regulated Gene Required for Prostate Cancer Growth", "The Prostate", 2006, pp. 886-894, vol. 66.

Reynolds, A., et al., "Rational siRNA design for RNA interference", "Nature Biotechnology", Mar. 2004, pp. 326-330, vol. 22, No. 3.

Roche, K. C., et al., "Regulation of ATR-dependent pathways by the FHA domain containing protein SNIP1", "Oncogene", 2007, pp. 4523-4530, vol. 26.

Shan, N., et al., "MiR-153 inhibits migration and invasion of human non-small-cell lung cancer by targeting ADAM19", "Biochemical and Biophysical Research Communications", Dec. 2, 2014, pp. 385-391, vol. 456.

Soubeyrand, S., et al., "ERK1/2 regulates hepatocyte Trib1 in response to mitochondrial dysfunction", "Biochimica et Biophysica Acta", Oct. 24, 2013, pp. 3405-3414, vol. 1833.

PHARMACEUTICAL COMPOSITION FOR TREATING CANCER COMPRISING MICRORNA AS ACTIVE INGREDIENT

CROSS-REFERENCE TO RELATED APPLICATIONS

This is a continuation under the provisions of 35 U.S.C. § 119 of U.S. patent application Ser. No. 15/553,097 filed Aug. 23, 2017, which in turn is a U.S. national phase under the provisions of 35 U.S.C. § 371 of International Patent Application No. PCT/KR2016/001828 filed Feb. 25, 2016, which in turn claims priority of Korean Patent Application No. 10-2015-0026557 filed Feb. 25, 2015. The disclosures of U.S. patent application Ser. No. 15/553,097, International Patent Application No. PCT/KR2016/001828, and Korean Patent Application No. 10-2015-0026557 are hereby incorporated herein by reference in their respective entireties, for all purposes.

TECHNICAL FIELD

The present invention relates to an anticancer pharmaceutical composition comprising double-stranded miRNA as an active ingredient. More specifically, the present invention relates to an anticancer pharmaceutical composition comprising, as pharmaceutically active ingredient, miR-3670, miR-8078, or miR-4477a which is capable of effectively inhibiting cancer cell proliferation or inducing cancer cell apoptosis, together with a pharmaceutically acceptable carrier.

BACKGROUND ART

As effective and traditional methods for treating diseases caused by uncontrolled gene control, particularly diseases referred to as cancers, methods of removing tumors by surgical excision have been used. However, where primary cancer is metastasized to other organs, surgical excision is impossible and anticancer chemotherapies have been used. As anticancer agents for chemotherapy, monomolecular compounds synthesized by organic or inorganic methods have been mainly used. Such anticancer drugs have been developed and used against cancer diseases in order mainly to effectively target proteins that disturb signaling pathways by overexpression of phosphorylation proteins included in signaling pathways, thereby inhibiting the activity of the proteins. Such traditional chemotherapies may cause many side effects, because anticancer drugs used are artificially synthesized foreign substances and target already overexpressed proteins.

The development of therapeutic drugs to replace the traditional chemotherapies has been attempted in various ways. One of such attempts is the use of small interfering RNA (hereinafter referred to as siRNA) (Iorns, E., Lord, C. J., Turner, N. & Ashworth, A. Utilizing RNA interference to enhance cancer drug discovery. Nat Rev Drug Discov 6, 556-68. 2007). siRNA is a single-stranded RNA consisting of 16 to 27 nucleotides and serves as one component of a ribonucleoprotein complex known as an RNA Induced Silencing Complex (RISC) in cells (Tomari, Y. & Zamore, P. D. Perspective: machines for RNAi. Genes Dev 19, 517-29, 2005, Chu, C. Y. & Rana, T. M. Potent RNAi by short RNA triggers. Rna 14, 1714-9, 2008, Mittal, V. Improving the efficiency of RNA interference in mammals. Nat Rev Genet 5, 355-65, 2004, Reynolds, A. et al. Rational siRNA design for RNA interference. Nat Biotechnol 22, 326-30. 2004). The RISC functions as RNA scissors to cleave messenger RNA (hereinafter referred to as mRNA) to thereby inhibit the production of protein from mRNA. siRNA contained in the RISC may bind to mRNA having a sequence complementary to the siRNA sequence to form double-stranded RNA, and the RISC may act as RNA scissors to cleave target mRNA so that the mRNA can no longer function as a template that repeatedly produces protein.

The siRNA-based anticancer drugs as described above are considered advanced over the monomolecular anticancer drugs in that they cleave mRNA before protein production and use RNA and the intracellular RISC pathway. However, there is a side effect that cannot be solved even by the siRNA-based technology (Jackson, A. L. et al. Widespread siRNA "off-target" transcript silencing mediated by seed region sequence complementarity. Rna 12, 1179-87, 2006., Jackson, A. L. et al. Position-specific chemical modification of siRNAs reduces "off-target" transcript silencing. Rna 12, 1197-205, 2006., Jackson, A. L. et al. Expression profiling reveals off-target gene regulation by RNAi. Nat Biotechnol 21, 635-7, 2003., Nielsen, C. B. et al. Determinants of targeting by endogenous and exogenous microRNAs and siRNAs. Rna 13, 1894-910, 2007., Peek, A. S. & Behlke, M. A. Design of active small interfering RNAs. Curr Opin Mol Ther 9, 110-8, 2007.). This side effect is a phenomenon known as the off-target effect. As described above, siRNA acts to cleave mRNA having a sequence complementary to the siRNA sequence. However, siRNA may also bind to and cleave a non-target mRNA which is not complementary to the entire sequence of the siRNA, but is complementary to only a portion of the siRNA sequence. This phenomenon is known as the off-target effect.

To overcome the above-described technical disadvantage of siRNA-based anticancer agents, studies on the use of microRNA (hereinafter referred to as "miRNA") as therapeutic agents are in progress (Agostini, M. & Knight, R. A. miR-34: from bench to bedside. Oncotarget 5, 872-81, 2014., van Rooij, E., Purcell, A. L. & Levin, A. A. Developing MicroRNA Therapeutics. Circulation Research 110, 496-507, 2012., Burnett, J. C. & Rossi, J. J. RNA-based therapeutics: current progress and future prospects. Chem Biol 19, 60-71, 2012., Dangwal, S. & Thum, T. microRNA therapeutics in cardiovascular disease models. Annu Rev Pharmacol Toxicol 54, 185-203, 2014.). miRNA is an RNA consisting of 16 to 27 nucleotides and is classified as protein non-coding RNA against a messenger RNA (mRNA) that is translated into protein (Carthew, R. W. & Sontheimer, E. J. Origins and Mechanisms of miRNAs and siRNAs. Cell 136, 642-55, 2009., MacFarlane, L.-A. & Murphy, P. R. MicroRNA: Biogenesis, Function and Role in Cancer. Current Genomics 11, 537-561, 2010., Bartel, D. P. MicroRNAs: target recognition and regulatory functions. Cell 136, 215-33, 2009.). miRNA is found in the genome of higher animal and plant cells, and is known to play a key role in regulating cell metabolisms and functions, including cell production, growth, differentiation and death. Until now, about 2000 kinds of miRNAs have been found in the human genome, and the functions of a considerable amount of the miRNAs are not yet known.

miRNA is transcribed from the genome into RNA by RNA polymerase known as Pol II, and the initial length of the miRNA is various without being specified (Carthew, R. W. & Sontheimer, E. J. Origins and Mechanisms of miRNAs and siRNAs. Cell 136, 642-55, 2009., Brodersen, P. & Voinnet, O. Revisiting the principles of microRNA target recognition and mode of action. Nat Rev Mol Cell Biol 10, 141-148, 2009). This is attributable to the positional variety of miRNA in the genome. This is because miRNA is produced in various ways, including the case in which miRNA located in an intron (mRNA non-coding region) is transcribed at the same time point as mRNA production and in the case in which miRNA located in the intergenic region of the genome is transcribed individually (Malone, C. D. & Hannon, G. J. Small RNAs as guardians of the genome. Cell 136, 656-68, 2009.). miRNA produced in the initial stage as described above is known as primary microRNA (miR). Primary miR is processed into precursor miR (precursor miRNA, or pre-miR) by, for example, RNase known as intranuclear Drosha (Bartel, D. P. MicroRNAs: target recognition and regulatory functions. Cell 136, 215-33, 2009). Pre-miR has an RNA hairpin structure and consists of about 70-80 nucleotides. Pre-miR in the cellular nucleus is transported from the nucleus to the cytosol by exportin protein or the like, and is further processed in the cytosol by another RNase known as Dicer to thereby produce double-stranded mature microRNA (hereinafter, miR described without a qualifier means mature miR) consisting of 16-27 nucleotides. One RNA strand of double-stranded miR is selected, activated by binding to the ribonucleoprotein complex RISC, and binds to target mRNA based on the sequence of miR.

Generally, mRNA can be largely divided into three regions based on whether or not these regions are involved in protein coding: a coding region containing protein coding translation information, and 5'-UTR (Un-Translated Region) and 3'-UTR which have no protein coding information. While siRNA that induces cleavage of target mRNA having a sequence complementary thereto acts regardless of the 5'-UTR, 3'-UTR and coding region of mRNA, miR binds mainly to the 3'-UTR (Carthew, R. W. & Sontheimer, E. J. Origins and Mechanisms of miRNAs and siRNAs. Cell 136, 642-55, 2009., Bartel, D. P. MicroRNAs: target recognition and regulatory functions. Cell 136, 215-33, 2009.).

In addition to the difference in the position of binding to mRNA, the characteristic difference between siRNA and miRNA is that siRNA binds mainly to mRNA having a sequence complementary to the entire sequence of siRNA, whereas miRNA recognizes target mRNA, mainly through a seed region sequence located 2-8 nucleotides from the 5' end of the miRNA and having a limited length. Thus, even when the entire sequence of miRNA is not completely complementary to the sequence of a target sequence and contains a non-complementary sequence portion, the activity of the miRNA is not affected by the non-complementary sequence portion (Bartel, D. P. MicroRNAs: target recognition and regulatory functions. Cell 136, 215-33, 2009). Since the seed region is 6-8 nucleotides in length, there are various kinds of mRNAs whose 3' UTR has a sequence complementary to the seed region, and for this region, several kinds of mRNAs can be simultaneously controlled using one kind of miRNA. This nature of miRNA enables the miRNA to function as an efficient regulator in the control of many cellular physiological aspects, including cell division, growth, differentiation and death. Furthermore, the function of miRNA as a regulator provides an advantage in achieving effective anticancer effects. This is because miRNA can inhibit expression of a number of oncogenes at the same time, whereas siRNA aims to inhibit expression of a single gene.

The 3' UTR of many mRNAs contains a portion to which one or more miRNAs can bind. According to bioinformatics calculation, it is known that about 30% of all mRNAs is regulated by miRNA.

The fact that miRNA acts as a major regulator in signaling pathways can be seen from the fact that miRNA plays an important role in major diseases, including cancer (MacFarlane, L.-A. & Murphy, P. R. MicroRNA: Biogenesis, Function and Role in Cancer. Current Genomics 11, 537-561. 2010., Malone, C. D. & Hannon, G. J. Small RNAs as guardians of the genome. Cell 136, 656-68. 2009., Nicoloso, M. S., Spizzo, R., Shimizu, M., Rossi, S. & Calin, G. A. MicroRNAs—the micro steering wheel of tumour metastases. Nat Rev Cancer 9, 293-302. 2009., Landi, D., Gemignani, F. & Landi, S. Role of variations within microRNA-binding sites in cancer. Mutagenesis 27, 205-10. 2012.). In fact, several studies revealed that expression patterns of miRNAs in cancer cells greatly differ from expression patterns of miRNAs in normal cells. In addition, it is known that expression patterns of miRNAs greatly differ depending on primary organs in which cancer occurred. Specifically, various cancers, including lung cancer, liver cancer, skin cancer and blood cancer, show characteristic miRNA expression patterns according to the primary organs, indicating that miRNA plays an important role in cancer biology. In particular, it is known that the expression levels of miRNAs in cancer cells are generally lower than their expression levels in normal cells.

Based on the deep connection of miRNA in cancer, it has recently been attempted to use miRNAs as anticancer therapeutic agents. For example, miRNA, named "miR-34a", is under clinical trials to verify its abilities to inhibit cancer cell proliferation and induce cancer cell apoptosis (Wiggins, J. F. et al. Development of a lung cancer therapeutic based on the tumor suppressor microRNA-34. Cancer Res 70, 5923-30. 2010., Bader, A. G. et al. miR-34 Regulated Genes and Pathways as Targets for Therapeutic Intervention. Google Patents, 2009., Hermeking, H. The miR-34 family in cancer and apoptosis. Cell Death Differ 17, 193-9. 2010., Chang, T. C. et al. Transactivation of miR-34a by p53 broadly influences gene expression and promotes apoptosis. Mol Cell 26, 745-52. 2007.).

Accordingly, the present inventors have made extensive efforts to identify miRNA having better abilities to inhibit cancer cell proliferation and induce cancer cell apoptosis than miR-34a which is under clinical trials. As a result, the present inventors have identified miR-3670, miR-8078 and miR-4477a, which have excellent anticancer efficacy, and have found that these miRNAs exhibit anticancer effects by effectively inhibiting expressions of a number of genes known as oncogenes, thereby competing the present invention.

DISCLOSURE OF INVENTION

Technical Problem

It is an object of the present invention to identify miRNA having excellent abilities to inhibit cancer cell proliferation and induce cancer cell apoptosis, and to provide a pharmaceutical composition for the treatment of cancer, which comprises the miRNA as an active ingredient.

Technical Solution

To achieve the above object, the present invention provides a pharmaceutical composition for treating cancer, which comprises, as an active ingredient, one or more miRNAs selected from the group consisting of miR-3670, miR-8078 and miR-4477a.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
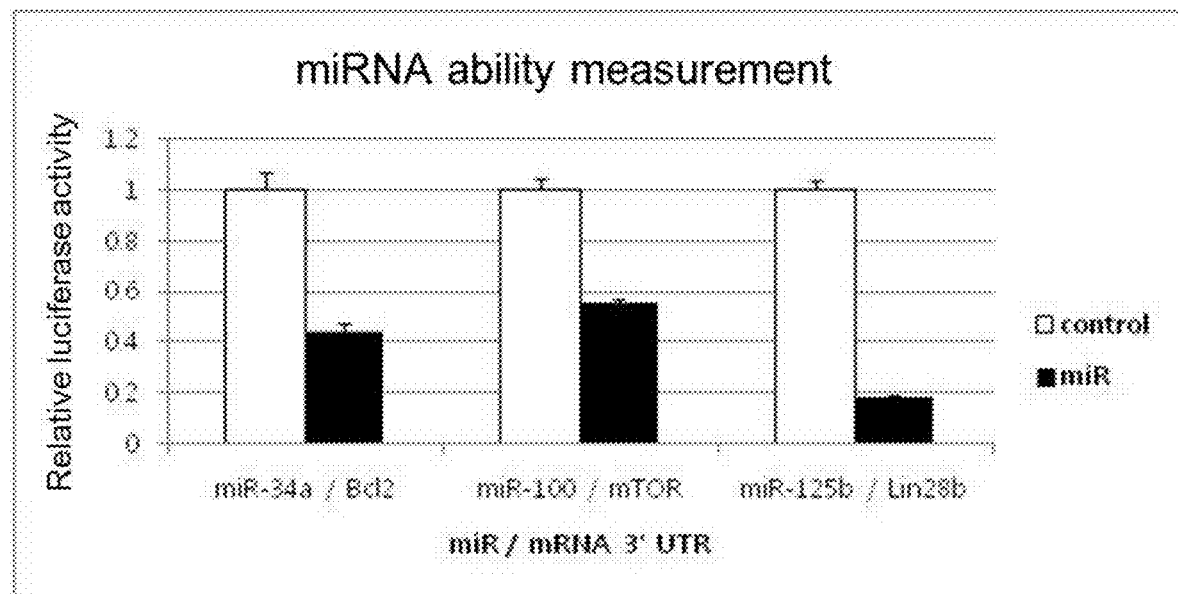
FIG. 1 shows the results of measuring the protein expression inhibitory abilities of miR-34a, miR-100 and miR-125b. In order to measure whether or not the miRNA used in construction of the screening library would have activity, miR-34a, miR-100 and miR-125b were typically selected from an entire screening library, and each of mRNA 3'UTRs known to be silenced by these miRNAs was inserted into the 3'UTR of luciferase expression vectors and the protein expression inhibitory abilities were measured.

Unless defined otherwise, all technical and scientific terms used herein have the same meaning as commonly understood by one of ordinary skill in the art to which the invention pertains. Generally, the nomenclature used herein is that which is well known and commonly employed in the art.

In the present invention, it has been attempted to identify miRNA having better efficacy than miR-34a known to have anticancer effects and to evaluate the anticancer effects of the identified miRNA.

In the present invention, a screening library consisting of about 1700 miRNAs was synthesized (Table 1). NCI-H460 (lung cancer cell line) was treated with the screening library, and the abilities of the miRNAs to inhibit the growth of the cancer cells were measured. As a result, miR-3670, miR-8078 and miR-4477a, which exhibited better efficacy than miR-34a and have the following nucleotide sequences, were identified (Table 3). It was found that the identified miRNAs have excellent anticancer effects (FIGS. 4 to 8).

Therefore, the present invention is directed to a pharmaceutical composition for treating cancer, which comprises as an active ingredient, one or more miRNAs selected from the group consisting of miR-3670, miR-8078 and miR-4477a.

In the present invention, the miR-3670 may comprise, as an active ingredient, a double-stranded RNA having the nucleotide sequences of SEQ ID NO: 35 and SEQ ID NO: 36 or SEQ ID NO: 35 and SEQ ID NO: 67.

In the present invention, the miR-4477a may comprise, as an active ingredient, a double-stranded RNA having the nucleotide sequences of SEQ ID NO: 43 and SEQ ID NO: 44 or SEQ ID NO: 43 and SEQ ID NO: 68.

In the present invention, the miR-8078 may comprise, as an active ingredient, a double-stranded RNA having the nucleotide sequences of SEQ ID NO: 65 and SEQ ID NO: 66 or SEQ ID NO: 65 and SEQ ID NO: 69.

In other words, an miR-3670 template strand of the present invention may be represented by SEQ ID NO: 35.

5'- AGAGCUCACAGCUGUCCUUCUCUA - 3' (MIMAT0018093.

SEQ ID NO: 35)

Although miRNA which is active in vivo is single-stranded, it should be delivered into cells, in a double-stranded form together with a nucleotide sequence having a length similar thereto, so that it will bind to the RISC. Herein, the antisense sequence binding to the sequence is complementary to the active sequence. The complementary sequence may be a perfect complementary sequence or an endogenous sequence. Nucleotides located either at the 3' end of each double-stranded sequence or at the 3' end of one strand may not bind with nucleotides of the antisense sequence, and such nucleotides are known as the 3'-overhang. The double-stranded sequence may comprise the 3'-overhang.

In other words, the perfect complementary sequence of the miR-3670 may be represented by SEQ ID NO: 36.

(SEQ ID NO: 36)
5' - GAGAAGGACAGCUGUGAGCUCUUU - 3'

In addition, the endogenous complementary sequence of the miR-3670 may be represented by SEQ ID NO: 67.

(SEQ ID NO: 67)
5' - GACUGGUAUAGCUGCUUUUGGAGCCUCA - 3'

As described in the Background Art section above, the seed sequence corresponding to 8-9$^{th}$ nucleotides counting from the second nucleotide of the active sequence of miRNA is the major factor of activity. A long double-stranded sequence comprising the seed region may be used in preparation of double-stranded RNA.

Similarly to miR-3670, active sequences of miR-4477a and miR-8078 and complementary sequences for forming double-stranded sequences therewith may be represented by the following sequences. These double-stranded sequences may comprise the 3'-overhang as described above to form long double-stranded sequences, and may also comprise the seed region to form long double-stranded sequences.

miR-4477a
5'- CUAUUAAGGACAUUUGUGAUUC -3' (MIMAT0019004 SEQ ID NO: 43)

The perfect complementary sequence of the miR-4477a:

(SEQ ID NO: 44)
5'- AUCACAAAUGUCCUUAAUAGUU -3'

The endogenous complementary sequence of the miR-4477a:

5'- AUCACAAAUGUCCUUAAUGGCA -3' (SEQ ID NO: 68)

miR-8078
5'- GGUCUAGGCCCGGUGAGAGACUC (MIMAT0031005, SEQ ID NO: 65)

The perfect complementary sequence of the miR-8078:

(SEQ ID NO: 66)
5'- GUCUCUCACCGGGCCUAGACCUU

The endogenous complementary sequence of the miR-8078:

(SEQ ID NO: 69)
5'- CUCCACCGGGCUGACCGGCCUG -3'

In the present invention, it was found that the miRNAs identified through library screening exhibit anticancer effects by controlling genes generally known to play a major role in the induction, production and growth of cancer cells. miRNAs characterized in that one kind of miRNA can simultaneously control expressions of a number of mRNA at the same time. This nature was also found in the present invention, and is useful for the development of new oligo-based anticancer drugs.

Figure 6:
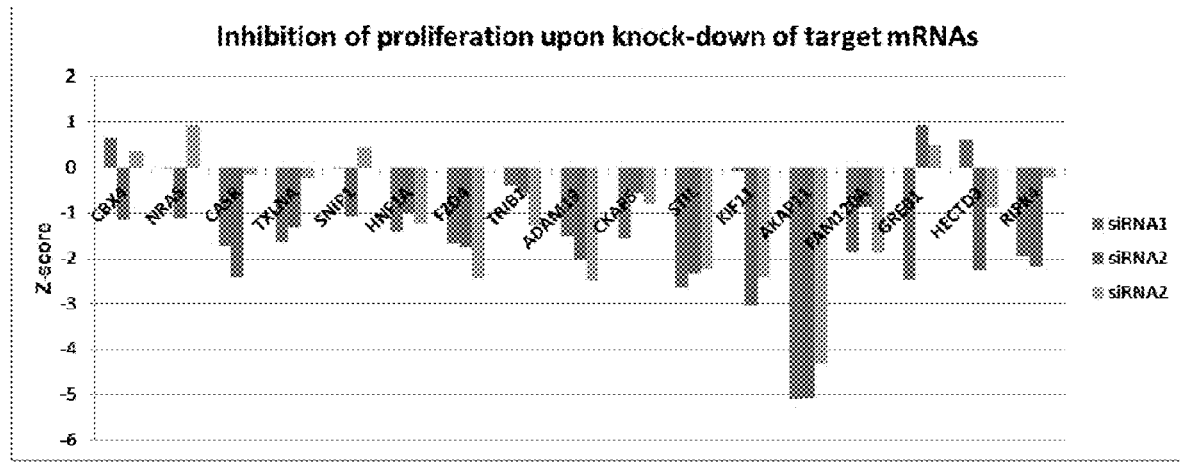
FIG. 6 shows the results obtained by selecting target candidates using the miRNA target prediction software, and expressing the apoptotic abilities of siRNAs, which target the selected candidates, as Z-score.

It was found that the miR-3670 of the present invention inhibits the expressions of the CBX4, NRAS, CASR, TXLNA, SNIP1, HNF1A, FZD4, TRIB1, ADMA19, and CKAP5 at the same time, the miR-8078 inhibits the expressions of GREB1, HECTD3, and RIPK4, and the miR-4477a inhibits the expressions of STIL, KIF11, AKAP11, and FAM120A at the same time (FIG. 6).

Target genes to be inhibited by the miRNA of the present invention are known to have the following functions.

It is known that CBX4 (polycomb chromobox 4) is involved in tumor angiogenesis and stimulation of tumor metastasis, and NRAS plays a major role in tumor growth and cell division (Orouji, E. et al. MAP Kinase pathway gene copy alterations in NRAS/BRAF wild-type advanced melanoma. Int J Cancer (2015); Zheng, C. et al. MicroRNA-195 functions as a tumor suppressor by inhibiting CBX4 in hepatocellular carcinoma. Oncol Rep 33, 1115-22 (2015); Jiao, H. K. et al. Prognostic significance of Cbx4 expression and its beneficial effect for transarterial chemoembolization in hepatocellular carcinoma. Cell Death Dis 6, e1689 (2015); Ohashi, K. et al. Characteristics of lung cancers harboring NRAS mutations. Clin Cancer Res 19, 2584-91 (2013)).

CASR is found to be overexpressed in tumors and is required for tumor metastasis, and TXLNA is known to be related to tumor growth and metastasis. Reported clinical results indicated that a patient group showing high expression levels of TXLNA has low survival rate (Mashidori, T., Shirataki, H., Kamai, T., Nakamura, F. & Yoshida, K. Increased alpha-taxilin protein expression is associated with the metastatic and invasive potential of renal cell cancer. Biomed Res 32, 103-10 (2011); Tennakoon, S., Aggarwal, A. & Kallay, E. The calcium-sensing receptor and the hallmarks of cancer. Biochim Biophys Acta (2015); Ohtomo, N. et al. Expression of alpha-taxilin in hepatocellular carcinoma correlates with growth activity and malignant potential of the tumor. Int J Oncol 37, 1417-23 (2010)).

SNIP1 known as a transcriptional coactivator stimulates expression of cyclin D1 which is essential for cell growth and division. It is known that a patient group showing high expression levels of SNIP1 has poor prognosis. Furthermore, it is known that SNIP1 binds to c-Myc functioning as a major regulator of cell proliferation to thereby stimulate tumor growth (Li, Q. et al. SNIP1: a new activator of HSE signaling pathway. Mol Cell Biochem 362, 1-6 (2012); Fujii, M. et al. SNIP1 is a candidate modifier of the transcriptional activity of c-Myc on E box-dependent target genes. Mol Cell 24, 771-83 (2006); Roche, K. C., Rocha, S., Bracken, C. P. & Perkins, N. D. Regulation of ATR-dependent pathways by the FHA domain containing protein SNIP1. Oncogene 26, 4523-30 (2007); Jeon, H. S. et al. High expression of SNIP1 correlates with poor prognosis in non-small cell lung cancer and SNIP1 interferes with the recruitment of HDAC1 to RB in vitro. Lung Cancer 82, 24-30 (2013); Liang, X. et al. Hypoxia-inducible factor-1 alpha, in association with TWIST2 and SNIP1, is a critical prognostic factor in patients with tongue squamous cell carcinoma. Oral Oncol 47, 92-7 (2011)).

HNF1A and FZD4 are components in the Wnt signaling pathway, which are deeply involved in tumor growth and survival. The Wnt signaling pathways have been intensively studied in tumor biology, and the importance thereof is widely known. TRIB1 is known to play a role to inhibit growth, metastasis and apoptosis of tumor cell and to regulate the MAPK signaling pathway which is a major signaling pathway of tumor growth (Pecina-Slaus, N. et al. Wnt signaling transcription factors TCF-1 and LEF-1 are upregulated in malignant astrocytic brain tumors. Histol Histopathol 29, 1557-64 (2014); Ueno, K. et al. Tumor suppressor microRNA-493 decreases cell motility and migration ability in human bladder cancer cells by down-regulating RhoC and FZD4. Mol Cancer Ther 11, 244-53 (2012); Lin, Z. Y. et al. MicroRNA-224 inhibits progression of human prostate cancer by downregulating TRIB1. Int J Cancer 135, 541-50 (2014); Soubeyrand, S., Naing, T., Martinuk, A. & McPherson, R. ERK1/2 regulates hepatocyte Trib1 in response to mitochondrial dysfunction. Biochim Biophys Acta 1833, 3405-14 (2013)).

ADAM19 is a protein distributed in the cell membrane, and is known to perform a variety of biological functions, including cell-cell interactions and cell-extracellular matrix interactions. As known in tumor biology, ADAM19 is deeply associated with tumor growth and metastasis. CKAP5 gene found to play an important role in tumor survival through gene functional screening was found to be controlled by the miRNA in the present invention. GREB1 is associated with the signaling pathways of tissues or tumors that respond to hormones, and is known to be overexpressed in various kinds of tumor cells to stimulate the growth of the cells (Zhang, Q. et al. Role of microRNA-30c targeting ADAM19 in colorectal cancer. PLoS One 10, e0120698 (2015); Shan, N., Shen, L., Wang, J., He, D. & Duan, C. MiR-153 inhibits migration and invasion of human non-small-cell lung cancer by targeting ADAM19. Biochem Biophys Res Commun 456, 385-91 (2015); Martens-de Kemp, S. R. et al. Functional genetic screens identify genes essential for tumor cell survival in head and neck and lung cancer. Clin Cancer Res 19, 1994-2003 (2013); Rae, J. M. et al. GREB1 is a novel androgen-regulated gene required for prostate cancer growth. Prostate 66, 886-94 (2006); Zhang, L. et al. Development of transcriptomic biomarker signature in human saliva to detect lung cancer. Cell Mol Life Sci 69, 3341-50 (2012); Laviolette, L. A., Hodgkinson, K. M., Minhas, N., Perez-Iratxeta, C. & Vanderhyden, B. C. 17beta-estradiol upregulates GREB1 and accelerates ovarian tumor progression in vivo. Int J Cancer 135, 1072-84 (2014)).

HECTD3 is E3 ubiquitin ligase and is known to attach polyubiquitin to caspase-8, which triggers apoptosis, to induce degradation of caspase-8, thereby inhibiting tumor cell apoptosis. Also, HECTD3 is known to stabilize MALT1 protein to thereby increase resistance to cisplatin anticancer drugs. RIPK4 is receptor-interacting protein kinase 4, and is known to induce accumulation of the cell growth signaling factor β-catenin and activate the Wnt signaling pathway. It is known that artificial removal of RIPK4 can inhibit tumor growth in tumor animal models (Li, Y. et al. The HECTD3 E3 ubiquitin ligase facilitates cancer cell survival by promoting K63-linked polyubiquitination of caspase-8. Cell Death Dis 4, e935 (2013); Li, Y. et al. The HECTD3 E3 ubiquitin ligase suppresses cisplatin-induced apoptosis via stabilizing MALT1. Neoplasia 15, 39-48 (2013); Huang, X. et al. Phosphorylation of Dishevelled by protein kinase RIPK4 regulates Wnt signaling. Science 339, 1441-5 (2013)).

The STIL gene, which is an essential factor in G2 phase-to-M phase transition in the cell cycle is known to be highly expressed in various kinds of cells and to be necessary for tumor growth and survival. It is known that KIF11 is also necessary for tumor cell growth and metastasis and that inhibition of the activity of KIF11 can inhibit tumor growth (Erez, A. et al. Sil overexpression in lung cancer characterizes tumors with increased mitotic activity. Oncogene 23, 5371-7 (2004); Erez, A. et al. The SIL gene is essential for mitotic entry and survival of cancer cells. Cancer Res 67, 4022-7 (2007); Tang, Y., Orth, J. D., Xie, T. & Mitchison, T. J. Rapid induction of apoptosis during Kinesin-5 inhibitor-induced mitotic arrest in HL60 cells. Cancer Lett 310, 15-24 (2011); Venere, M. et al. The mitotic kinesin KIF11 is a driver of invasion, proliferation, and self-renewal in glioblastoma. Sci Transl Med 7, 304ra143 (2015)).

AKAP11 that binds protein kinase A (PKA) to increase the PKA activity also binds to GSK-3 beta to promote PKA-mediated phosphorylation of GSK-3. Phosphorylated GSK-3 beta loses its activity, which is a major mechanism that is recognized as a growth stimulating signal in cells to induce tumor growth. Tumor cells are exposed to various stress conditions, such as acidic conditions, oxygen deficient conditions, etc., and maintain a mechanism by which death of tumor cells is inhibited even under such severe conditions. For example, it is known that FAM120A that is an RNA-binding protein activates kinases such as Src to inhibit cell apoptosis and increase drug resistance (Logue, J. S. et al. AKAP220 protein organizes signaling elements that impact cell migration. J Biol Chem 286, 39269-81 (2011); Whiting, J. L. et al. Protein Kinase A Opposes the Phosphorylation-dependent Recruitment of Glycogen Synthase Kinase 3beta to A-kinase Anchoring Protein 220. J Biol Chem 290, 19445-57 (2015); Tanji, C. et al. A-kinase anchoring protein AKAP220 binds to glycogen synthase kinase-3beta (GSK-3beta) and mediates protein kinase A-dependent inhibition of GSK-3beta. J Biol Chem 277, 36955-61 (2002); Tanaka, M. et al. A novel RNA-binding protein, Ossa/C9orf10, regulates activity of Src kinases to protect cells from oxidative stress-induced apoptosis. Mol Cell Biol 29, 402-13 (2009); Bartolome, R. A. et al. IL13 Receptor alpha2 Signaling Requires a Scaffold Protein, FAM120A, to Activate the FAK and PI3K Pathways in Colon Cancer Metastasis. Cancer Res 75, 2434-44 (2015)).

Figure 7:
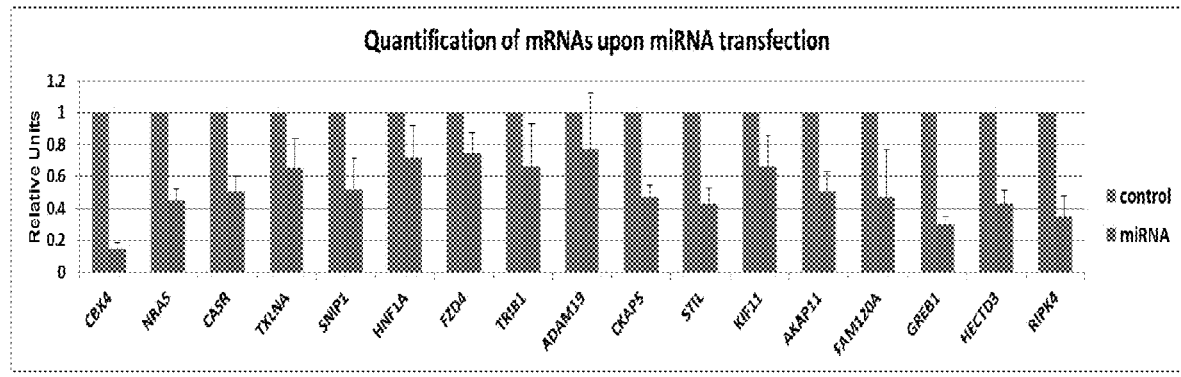
FIG. 7 shows the results of qPCR performed to analyze the extent to which the expression of the genes shown in FIG. 6 would be inhibited by miRNA.
Figure 8:
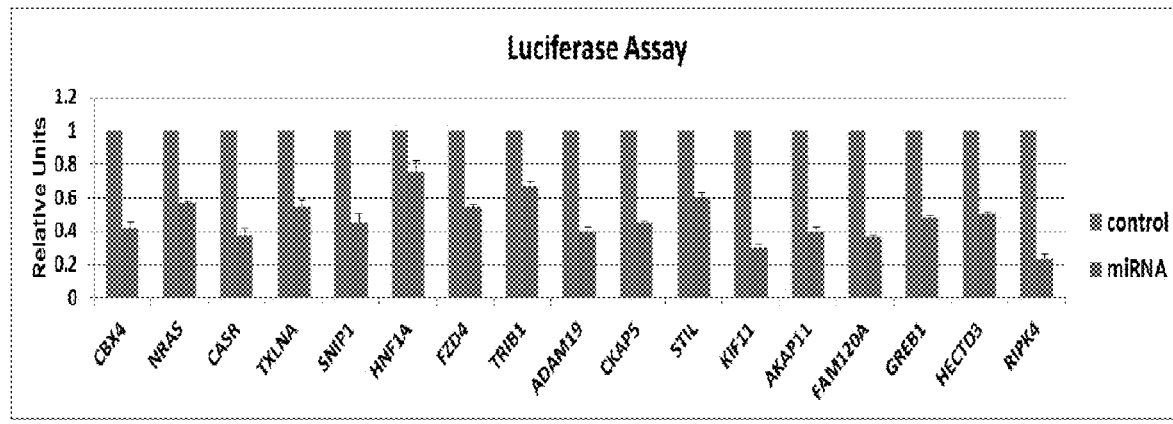
FIG. 8 shows the results obtained by cloning the 3' UTR of the genes, shown in FIG. 6, into the 3' UTR of luciferase, and measuring the extent to which the expression of the luciferase protein would be inhibited by miRNA.

In the present invention, it was shown that, when the intracellular contents of the above-described genes were reduced using siRNA, cell growth was inhibited, like when miR-3670, miR4477a or miR-8078 was used (FIG. 6). In addition, the results of qPCR indicated that when miR-3670, miR-4477a or miR-8078 was delivered into lung cancer cells, the mRNA expression levels of the genes were reduced (FIG. 7). Furthermore, the luciferase assay results indicated that the above-described genes are genes that are targeted directly by miR-3670, miR-4477a or miR-8078 (FIG. 8). This suggests that miR-3670, miR-4477a or miR-8078 directly and simultaneously inhibits expressions of various genes important in tumor cell growth and survival to thereby induce tumor cell apoptosis.

In the present invention, the cancer may be one or more cancers selected from the group consisting of: a primary cancer such as lung cancer, liver cancer, stomach cancer, colorectal cancer, pancreatic cancer, gallbladder and bile duct cancer, breast cancer, leukemia, esophageal cancer, non-Hodgkin lymphoma, thyroid cancer, cervical cancer, or skin cancer; a metastatic carcinoma arising from metastasis to other organs from the primary cancer site of origin; and a neoplastic cell disease caused by the promotion of abnormally excessive cell division, but is not limited thereto.

The sequence of miRNA that can be used as an active ingredient of a pharmaceutical composition for treating cancer according to the present invention is a sequence derived from the human genome, but may be an miRNA sequence obtained from other animal genomes without limiting the miRNA-derived genome to the human genome.

In the present invention, miRNA may be used as various miRNA mimics, which generates biologically equivalent effect. For example, modified miRNA comprising an miRNA sequence containing the same seed region may be used. Herein, the length of SEQ ID NO: 1 or SEQ ID NO: 2 may be reduced, and a short-length miRNA mimic consisting of 15 nucleotides may also be used.

In the present invention, miRNA mimics for the miRNA may partially comprise a phosphorothioate structure in which a RNA phosphate backbone structure is substituted with another element such as sulfur. Moreover, those obtained by wholly or partially substituting RNA with DNA, PNA (peptide nucleic acid) or LNA (locked nucleic acid) molecule may also be used. In addition, those obtained by substituting the 2' hydroxyl group of RNA sugar with various functional structures may also be used. Such modification includes, but not limited to, methylation, methoxylation, fluorination or the like.

In the present invention, miRNA is not limited to the mature miRNA and the double-stranded RNA of the miRNA mimic derived therefrom, but can be used in the form of an miRNA precursor. The miRNA precursor can also be obtained by substitution of the above-described RNA phosphate backbone structure, whole or partial substitution of RNA nucleic acid with a DNA, PNA or LNA molecule, or modification of the 2' hydroxyl group of RNA sugar.

In the present invention, miRNA can be used in the form of an miRNA precursor or a primary miRNA (pri-miRNA), and it can be synthesized by a chemical method or delivered to cells in the form of a plasmid so as to be expressed.

Examples of a method of delivering miRNA to cells cultured in a culture dish, which can be used in the present invention, include a method of using a mixture of miRNA and cationic lipid, a method of delivering miRNA to cells by electrical stimulus, and a method of using virus, but are not limited thereto.

A pharmaceutical composition for treating cancer comprising the miRNA of the present invention as an active ingredient may further comprise a pharmaceutically acceptable carrier, and may be formulated together with the carrier.

As used herein, the term "pharmaceutically acceptable carrier" refers to a carrier or diluent that does not impair the biological activity and characteristics of an administered compound without irritating an organism. As a pharmaceutically acceptable carrier in a composition that is formulated as a liquid solution, a sterile and biocompatible carrier is used. The pharmaceutically acceptable carrier may be physiological saline, sterile water, Ringer's solution, buffered saline, albumin injection solution, dextrose solution, maltodextrin solution, glycerol, ethanol, or a mixture of two or more thereof. In addition, the composition of the present invention may, if necessary, comprise other conventional additives, including antioxidants, buffers, and bacteriostatic agents. Further, the composition of the present invention may be formulated as injectable forms such as aqueous solutions, suspensions or emulsions with the aid of diluents, dispersants, surfactants, binders and lubricants. In addition, the composition according to the present invention may be formulated in the form of pills, capsules, granules, or tablets.

A composition for preventing or treating cancer, which comprises the miRNA of the present invention and a pharmaceutically acceptable carrier, can be applied as any formulation comprising it as an active ingredient and may be prepared as an oral or parenteral formulation. Pharmaceutical formulations of the present invention include those suitable for oral, rectal, nasal, topical (including buccal and sublingual), subcutaneous, vaginal or parenteral (including intramuscular, subcutaneous and intravenous) administration or a form suitable for administration by inhalation or insufflation.

Examples of oral formulations comprising the composition of the present invention as an active ingredient include tablets, troches, lozenges, aqueous or emulsified suspensions, powders, granules, emulsions, hard or soft capsules, syrups, or elixirs. Formulations such as tablets or capsules may include a binder such as lactose, saccharose, sorbitol, mannitol, starch, amylopectin, cellulose or gelatin, an expedient such as dicalcium phosphate, a disintegrant such as corn starch or sweet potato starch, and a lubricant such as magnesium stearate, calcium stearate, sodium stearyl fumarate or polyethylene glycol wax. Capsule formulations may comprise, in addition to the above-mentioned substances, a liquid carrier such as fatty oil.

Parenteral formulations comprising the composition of the present invention as an active ingredient include injectable forms for subcutaneous, intravenous or intramuscular injection, suppositories, or sprays inhalable via the respiratory organ, such as aerosols. Injectable formulations may be prepared by mixing the composition of the present invention with a stabilizer or a buffer in water to prepare a solution or a suspension, and loading the solution or suspension into ampules or vials to prepare unit dosage forms. Suppository formulations include suppositories or retention enemas, e.g. containing conventional suppository bases such as cocoa buffer or other glycerides. For spray formulations, such as aerosols, a propellant for spraying a water-dispersed concentrate or wet powder may be used in combination with an additive.

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1: Construction of miRNA Screening Library

Based on stem-loop structure the 21 version human miRNA sequence provided from the miRNA database miRBase (www.mirbase.org), a screening library consisting of about 1700 kinds of miRNAs was synthesized as double-stranded miRNA sequences by a solid synthesis method that is used in conventional oligo synthesis. Each strand of the synthesized miRNAs was purified by reverse phase separation using C18 resin. All the synthesized miRNA strands were analyzed by MALDI-TOF MS spectrometry to determine whether or not the desired sequences were synthesized. For synthesis of double-stranded miRNAs, complementary strands were heated in the presence of salt at 95° C. for 2 minutes, and then cooled slowly for preparation of double strands.

TABLE 1 miRNA Sequences

| miRNA | SEQ ID NO: | Sequence 1 | SEQ ID NO: | Sequence 2 |
|---|---|---|---|---|
| hsa-let-7a-1 | 70 | UGAGGUAGUAGGUUGUAUAGUU | 71 | CUAUACAAUCUACUGUCUUUC |
| hsa-let-7a-2 | 72 | UGAGGUAGUAGGUUGUAUAGUU | 73 | CUGUACAGCCUCCUAGCUUUCC |
| hsa-let-7b | 74 | CUAUACAACCUACUGCCUUCCC | 75 | UGAGGUAGUAGGUUGUGUGGUU |
| hsa-let-7c | 76 | UGAGGUAGUAGGUUGUAUGGUU | 77 | CUGUACAACCUUCUAGCUUUCC |
| hsa-let-7d | 78 | CUAUACGACCUGCUGCCUUUCU | 79 | AGAGGUAGUAGGUUGCAUAGUU |
| hsa-let-7e | 80 | CUAUACGGCCUCCUAGCUUUCC | 81 | UGAGGUAGGAGGUUGUAUAGUU |
| hsa-let-7f-1 | 82 | UGAGGUAGUAGAUUGUAUAGUU | 83 | CUAUACAAUCUAUUGCCUUCCC |
| hsa-let-7f-2 | 84 | UGAGGUAGUAGAUUGUAUAGUU | 85 | CUAUACAGUCUACUGUCUUUCC |

TABLE 1-continued miRNA Sequences

| miRNA | SEQ ID NO: | Sequence 1 | SEQ ID NO: | Sequence 2 |
|---|---|---|---|---|
| hsa-let-7g | 86 | CUGUACAGGCCACUGCCUUGC | 87 | UGAGGUAGUAGUUUGUACAGUU |
| hsa-let-7i | 88 | UGAGGUAGUAGUUUGUGCUGUU | 89 | CUGCGCAAGCUACUGCCUUGCU |
| hsa-miR-1 | 90 | UGGAAUGUAAAGAAGUAUGUAU | 91 | ACAUACUUCUUUAUAUGCCCAU |
| hsa-miR-100 | 92 | CAAGCUUGUAUCUAUAGGUAUG | 93 | AACCCGUAGAUCCGAACUUGUG |
| hsa-miR-101 | 94 | UACAGUACUGUGAUAACUGAA | 95 | CAGUUAUCACAGUGCUGAUGCU |
| hsa-miR-103a | 96 | AGCAGCAUUGUACAGGGCUAUGA | 97 | AGCUUCUUUACAGUGCUGCCUUG |
| hsa-miR-103b | 98 | UCAUAGCCCUGUACAAUGCUGCU | 99 | CAGCAUUGUACAGGGCUAUGAUU |
| hsa-miR-105 | 100 | UCAAAUGCUCAGACUCCUGUGGU | 101 | ACGGAUGUUUGAGCAUGUGCUA |
| hsa-miR-106a | 102 | CUGCAAUGUAAGCACUUCUUAC | 103 | AAAAGUGCUUACAGUGCAGGUAG |
| hsa-miR-106b | 104 | UAAAGUGCUGACAGUGCAGAU | 105 | CCGCACUGUGGGUACUUGCUGC |
| hsa-miR-107 | 106 | AGCAGCAUUGUACAGGGCUAUCA | 107 | AUAGCCCUGUACAAUGCUGCUUU |
| hsa-miR-10a | 108 | CAAAUUCGUAUCUAGGGGAAUA | 109 | UACCCUGUAGAUCCGAAUUUGUG |
| hsa-miR-10b | 110 | ACAGAUUCGAUUCUAGGGGAAU | 111 | UACCCUGUAGAACCGAAUUUGUG |
| hsa-miR-1178 | 112 | UUGCUCACUGUUCUUCCCUAG | 113 | CAGGGUCAGCUGAGCAUG |
| hsa-miR-1179 | 114 | AAGCAUUCUUUCAUUGGUUGG | 115 | AACCAAUGAAAGAAUGCUUUU |
| hsa-miR-1180 | 116 | UUUCCGGCUCGCGUGGGUGUGU | 117 | GGACCCACCCGGCCGGGAAUA |
| hsa-miR-1181 | 118 | CCGUCGCCGCCACCCGAGCCG | 119 | GCUCGGGUGGCGGCGACGGUU |
| hsa-miR-1182 | 120 | GAGGGUCUUGGGAGGGAUGUGAC | 121 | CACAUCCCUCCCAAGACCCUCUU |
| hsa-miR-1183 | 122 | CACUGUAGGUGAUGGUGAGAGUGGGCA | 123 | CCCACUCUCACCAUCACCUACAGUGUU |
| hsa-miR-1184 | 124 | CCUGCAGCGACUUGAUGGCUUCC | 125 | AAGCCAUCAAGUCGCUGCAGGUU |
| hsa-miR-1185-1 | 126 | AGAGGAUACCCUUUGUAUGUU | 127 | AUAUACAGGGGGAGACUCUAU |
| hsa-miR-1185-2 | 128 | AGAGGAUACCCUUUGUAUGUU | 129 | AUAUACAGGGGGAGACUCUCAU |
| hsa-miR-1193 | 130 | GGGAUGGUAGACCGGUGACGUGC | 131 | ACGUCACCGGUCUACCAUCCCUU |
| hsa-miR-1197 | 132 | UAGGACACAUGGUCUACUUCU | 133 | AAGUAGACCAUGUGUCCUAUU |
| hsa-miR-1199 | 134 | CCUGAGCCCGGGCCGCGCAG | 135 | UGCGGCCGGUGCUCAACCUGC |
| hsa-miR-1200 | 136 | CUCCUGAGCCAUUCUGAGCCUC | 137 | GGCUCAGAAUGGCUCAGGAGUU |
| hsa-miR-1202 | 138 | GUGCCAGCUGCAGUGGGGGAG | 139 | CCCCCACUGCAGCUGGCACUU |
| hsa-miR-1203 | 140 | CCCGGAGCCAGGAUGCAGCUC | 141 | GCUGCAUCCUGGCUCCGGGUU |
| hsa-miR-1204 | 142 | UCGUGGCCUGGUCUCCAUUAU | 143 | AAUGGAGACCAGGCCACGAUU |
| hsa-miR-1205 | 144 | UCUGCAGGGUUUGCUUUGAG | 145 | CAAAGCAAACCCUGCAGAUU |
| hsa-miR-1206 | 146 | UGUUCAUGUAGAUGUUUAAGC | 147 | UUAAACAUCUACAUGAACAUU |
| hsa-miR-1207 | 148 | UGGCAGGGAGGCUGGGAGGGG | 149 | UCAGCUGGCCCUCAUUUC |
| hsa-miR-1208 | 150 | UCACUGUUCAGACAGGCGGA | 151 | CGCCUGUCUGAACAGUGAUU |
| hsa-miR-122 | 152 | UGGAGUGUGACAAUGGUGUUUG | 153 | AACGCCAUUAUCACACUAAAUA |
| hsa-miR-1224 | 154 | CCCCACCUCCUCUCUCCUCAG | 155 | GUGAGGACUCGGGAGGUGG |
| hsa-miR-1225 | 156 | GUGGGUACGGCCCAGUGGGGG | 157 | UGAGCCCUGUGCCGCCCCAG |
| hsa-miR-1226 | 158 | GUGAGGGCAUGCAGGCCUGGAUGGGG | 159 | UCACCAGCCCUGUGUUCCCUAG |

TABLE 1-continued miRNA Sequences

| miRNA | SEQ ID NO: | Sequence 1 | SEQ ID NO: | Sequence 2 |
|---|---|---|---|---|
| hsa-miR-1227 | 160 | GUGGGGCCAGGCGGUGG | 161 | CGUGCCACCCUUUUCCCCAG |
| hsa-miR-1228 | 162 | GUGGGCGGGGGCAGGUGUGUG | 163 | UCACACCUGCCUCGCCCCCC |
| hsa-miR-1229 | 164 | GUGGGUAGGGUUUGGGGGAGAGCG | 165 | CUCUCACCACUGCCCUCCCACAG |
| hsa-miR-1231 | 166 | GUGUCUGGGCGGACAGCUGC | 167 | AGCUGUCCGCCCAGACACUU |
| hsa-miR-1233 | 168 | AGUGGGAGGCCAGGGCACGGCA | 169 | UGAGCCCUGUCCUCCCGCAG |
| hsa-miR-1234 | 170 | UCGGCCUGACCACCCACCCCAC | 171 | GGGGUGGGUGGUCAGGCCGAUU |
| hsa-miR-1236 | 172 | UGAGUGACAGGGGAAAUGGGGA | 173 | CCUCUUCCCCUUGUCUCUCCAG |
| hsa-miR-1237 | 174 | CGGGGGCGGGGCCGAAGCGCG | 175 | UCCUUCUGCUCCGUCCCCCAG |
| hsa-miR-1238 | 176 | CUUCCUCGUCUGUCUGCCCC | 177 | GUGAGUGGGAGCCCCAGUGUGUG |
| hsa-miR-124 | 178 | UAAGGCACGCGGUGAAUGCC | 179 | CGUGUUCACAGCGGACCUUGAU |
| hsa-miR-1243 | 180 | AACUGGAUCAAUUAUAGGAGUG | 181 | CUCCUAUAAUUGAUCCAGUUUU |
| hsa-miR-1244 | 182 | AAGUAGUUGGUUUGUAUGAGAUGGUU | 183 | CCAUCUCAUACAAACCAACUACUUUU |
| hsa-miR-1245a | 184 | AAGUGAUCUAAAGGCCUACAU | 185 | GUAGGCCUUUAGAUCACUUUU |
| hsa-miR-1245b | 186 | UCAGAUGAUCUAAAGGCCUAUA | 187 | UAGGCCUUUAGAUCACUUAAA |
| hsa-miR-1246 | 188 | AAUGGAUUUUUGGAGCAGG | 189 | UGCUCCAAAAAUCCAUUUU |
| hsa-miR-1247 | 190 | CCCCGGGAACGUCGAGACUGGAGC | 191 | ACCCGUCCCGUUCGUCCCCGGA |
| hsa-miR-1248 | 192 | ACCUUCUUGUAUAAGCACUGUGCUAAA | 193 | UAGCACAGUGCUUAUACAAGAAGGUUU |
| hsa-miR-1249 | 194 | ACGCCCUUCCCCCCCUUCUUCA | 195 | AGGAGGGAGGAGAUGGGCCAAGUU |
| hsa-miR-1250 | 196 | ACAUUUUCCAGCCCAUUCA | 197 | ACGGUGCUGGAUGUGGCCUUU |
| hsa-miR-1251 | 198 | CGCUUUGCUCAGCCAGUGUAG | 199 | ACUCUAGCUGCCAAAGGCGCU |
| hsa-miR-1252 | 200 | AGAAGGAAAUUGAAUUCAUUUA | 201 | CAAAUGAGCUUAAUUUCCUUUU |
| hsa-miR-1253 | 202 | AGAGAAGAAGAUCAGCCUGCA | 203 | CAGGCUGAUCUUCUUCUCUUU |
| hsa-miR-1254 | 204 | AGCCUGGAAGCUGGAGCCUGCAGU | 205 | UGCAGGCUCCAGCUUCCAGGCUUU |
| hsa-miR-1255a | 206 | AGGAUGAGCAAAGAAAGUAGAUU | 207 | UCUACUUUCUUUGCUCAUCCUUU |
| hsa-miR-1255b | 208 | AACCACUUUCUUUGCUCAUCCA | 209 | CGGAUGAGCAAAGAAAGUGGUU |
| hsa-miR-1256 | 210 | AGGCAUUGACUUCUCACUAGCU | 211 | CUAGUGAAGUCAAUGCCUUU |
| hsa-miR-1257 | 212 | AGUGAAUGAUGGGUUCUGACC | 213 | UCAGAACCCAUCAUUCACUUU |
| hsa-miR-1258 | 214 | AGUUAGGAUUAGGUCGUGGAA | 215 | CCACGACCUAAUCCUAACUUU |
| hsa-miR-125a | 216 | ACAGGUGAGGUUCUUGGGAGCC | 217 | UCCCUGAGACCCUUUAACCUGUGA |
| hsa-miR-125b-1 | 218 | UCCCUGAGACCCUAACUUGUGA | 219 | ACGGGUUAGGCUCUUGGGAGCU |
| hsa-miR-125b-2 | 220 | UCCCUGAGACCCUAACUUGUGA | 221 | UCACAAGUCAGGCUCUUGGGAC |
| hsa-miR-126 | 222 | UCGUACCGUGAGUAAUAAUGCG | 223 | CAUUAUUACUUUUGGUACGCG |
| hsa-miR-1260a | 224 | AUCCCACCUCUGCCACCA | 225 | GUGGCAGAGGUGGGAUUU |
| hsa-miR-1260b | 226 | AUCCCACCACUGCCACCAU | 227 | GGUGGCAGUGGUGGGAUUU |
| hsa-miR-1261 | 228 | AUGGAUAAGGCUUUGGCUU | 229 | GCCAAAGCCUUAUCCAUUU |
| hsa-miR-1262 | 230 | AUGGGUGAAUUUGUAGAAGGAU | 231 | CCUUCUACAAAUUCACCCAUUU |
| hsa-miR-1263 | 232 | AUGGUACCCUGGCAUACUGAGU | 233 | UCAGUAUGCCAGGGUACCAUUU |
| hsa-miR-1264 | 234 | CAAGUCUUAUUUGAGCACCUGUU | 235 | CAGGUGCUCAAAUAAGACUUGUU |

TABLE 1-continued miRNA Sequences

| miRNA | SEQ ID NO: | Sequence 1 | SEQ ID NO: | Sequence 2 |
|---|---|---|---|---|
| hsa-miR-1265 | 236 | CAGGAUGUGGUCAAGUGUUGUU | 237 | CAACACUUGACCACAUCCUGUU |
| hsa-miR-1266 | 238 | CCUCAGGGCUGUAGAACAGGGCU | 239 | CCCUGUUCUAUGCCCUGAGGGA |
| hsa-miR-1267 | 240 | CCUGUUGAAGUGUAAUCCCCA | 241 | GGGAUUACACUUCAACAGGUU |
| hsa-miR-1268a | 242 | CGGGCGUGGUGGUGGGGG | 243 | CCCACCACCACGCCCGUU |
| hsa-miR-1268b | 244 | CGGGCGUGGUGGUGGGGGUG | 245 | CCCCCACCACCACGCCCGUU |
| hsa-miR-1269a | 246 | CUGGACUGAGCCGUGCUACUGG | 247 | AGUAGCACGGCUCAGUCCAGUU |
| hsa-miR-1269b | 248 | CUGGACUGAGCCAUGCUACUGG | 249 | AGUAGCAUGGCUCAGUCCAGUU |
| hsa-miR-127 | 250 | UCGGAUCCGUCUGAGCUUGGCU | 251 | CUGAAGCUCAGAGGGCUCUGAU |
| hsa-miR-1270 | 252 | CUGGAGAUAUGGAAGAGCUGUGU | 253 | ACAGCUCUUCCAUAUCUCCAGUU |
| hsa-miR-1271 | 254 | AGUGCCUGCUAUGUGCCAGGCA | 255 | CUUGGCACCUAGCAAGCACUCA |
| hsa-miR-1272 | 256 | GAUGAUGAUGGCAGCAAAUUCUGAAA | 257 | UCAGAAUUUGCUGCCAUCAUCAUCUU |
| hsa-miR-1273a | 258 | GGGCGACAAAGCAAGACUCUUUCUU | 259 | GAAAGAGUCUUGCUUUGUCGCCCUU |
| hsa-miR-1273c | 260 | GGCGACAAAACGAGACCCUGUC | 261 | CAGGGUCUCGUUUUGUCGCCUU |
| hsa-miR-1273d | 262 | GAACCCAUGAGGUUGAGGCUGCAGU | 263 | UGCAGCCUCAACCUCAUGGGUUCUU |
| hsa-miR-1273e | 264 | UUGCUUGAACCCAGGAAGUGGA | 265 | CACUUCCUGGGUUCAAGCAAUU |
| hsa-miR-1273f | 266 | GGAGAUGGAGGUUGCAGUG | 267 | CUGCAACCUCCAUCUCCUU |
| hsa-miR-1273g | 268 | GGUGGUUUGAGGCUGCAGUAAGU | 269 | ACCACUGCACUCCAGCCUGAG |
| hsa-miR-1273h | 270 | CUGGGGAGGUCAAGGCUGCAGU | 271 | CUGCAGACUCGACCUCCCAGGC |
| hsa-miR-1275 | 272 | GUGGGGGAGAGGCUGUC | 273 | CAGCCUCUCCCCACUU |
| hsa-miR-1276 | 274 | UAAAGAGCCCUGUGGAGACA | 275 | UCUCCACAGGGCUCUUUAUU |
| hsa-miR-1277 | 276 | UACGUAGAUAUAUAUGUAUUUU | 277 | AAAUAUAUAUAUAUGUACGUAU |
| hsa-miR-1278 | 278 | UAGUACUGUGCAUAUCAUCUAU | 279 | AGAUGAUAUGCACAGUACUAUU |
| hsa-miR-1279 | 280 | UCAUAUUGCUUCUUUCU | 281 | AAAGAAGCAAUAUGAUU |
| hsa-miR-128-1 | 282 | UCACAGUGAACCGGUCUCUUU | 283 | CGGGGCCGUAGCACUGUCUGAGA |
| hsa-miR-128-2 | 284 | UCACAGUGAACCGGUCUCUUU | 285 | GGGGGCCGAUACACUGUACGAGA |
| hsa-miR-1281 | 286 | UCGCCUCCUCCUCUCCC | 287 | GAGAGGAGGAGGCGAUU |
| hsa-miR-1282 | 288 | UCGUUUGCCUUUUUCUGCUU | 289 | GCAGAAAAGGCAAACGAUU |
| hsa-miR-1283 | 290 | UCUACAAAGGAAAGCGCUUUCU | 291 | AAAGCGCUUUCCUUUGUAGAUU |
| hsa-miR-1284 | 292 | UCUAUACAGACCCUGGCUUUUC | 293 | AAAGCCAGGGUCUGUAUAGAUU |
| hsa-miR-1285 | 294 | UCUGGGCAACAAAGUGAGACCU | 295 | GAUCUCACUUUGUUGCCCAGG |
| hsa-miR-1286 | 296 | UGCAGGACCAAGAUGAGCCCU | 297 | GGCUCAUCUUGGUCCUGCAUU |
| hsa-miR-1287 | 298 | CUCUAGCCACAGAUGCAGUGAU | 299 | UGCUGGAUCAGUGGUUCGAGUC |
| hsa-miR-1288 | 300 | UGGACUGCCCUGAUCUGGAGA | 301 | GCAGAUCAGGACUGUAACUCACC |
| hsa-miR-1289 | 302 | UGGAGUCCAGGAAUCUGCAUUUU | 303 | AAUGCAGAUUCCUGGACUCCAUU |
| hsa-miR-129-1 | 304 | CUUUUUGCGGUCUGGGCUUGC | 305 | AAGCCCUUACCCCAAAAAGUAU |
| hsa-miR-129-2 | 306 | CUUUUUGCGGUCUGGGCUUGC | 307 | AAGCCCUUACCCCAAAAAGCAU |
| hsa-miR-1290 | 308 | UGGAUUUUUGGAUCAGGGA | 309 | CCUGAUCCAAAAAUCCAUU |

TABLE 1-continued miRNA Sequences

| miRNA | SEQ ID NO: | Sequence 1 | SEQ ID NO: | Sequence 2 |
|---|---|---|---|---|
| hsa-miR-1291 | 310 | UGGCCCUGACUGAAGACCAGCAGU | 311 | UGCUGGUCUUCAGUCAGGGCCAUU |
| hsa-miR-1292 | 312 | UGGGAACGGGUUCCGGCAGACGCUG | 313 | UCGCGCCCCGGCUCCCGUUC |
| hsa-miR-1293 | 314 | UGGGUGGUCUGGAGAUUUGUGC | 315 | ACAAAUCUCCAGACCACCCAUU |
| hsa-miR-1294 | 316 | UGUGAGGUUGGCAUUGUUGUCU | 317 | ACAACAAUGCCAACCUCACAUU |
| hsa-miR-1295a | 318 | UUAGGCCGCAGAUCUGGGUGA | 319 | ACCCAGAUCUGCGGCCUAAUU |
| hsa-miR-1295b | 320 | AAUAGGCCACGGAUCUGGGCAA | 321 | CACCCAGAUCUGCGGCCUAAU |
| hsa-miR-1296 | 322 | UUAGGGCCCUGGCUCCAUCUCC | 323 | GAGUGGGGCUUCGACCCUAACC |
| hsa-miR-1297 | 324 | UUCAAGUAAUUCAGGUG | 325 | CCUGAAUUACUUGAAUU |
| hsa-miR-1298 | 326 | CAUCUGGGCAACUGACUGAAC | 327 | UUCAUUCGGCUGUCCAGAUGUA |
| hsa-miR-1299 | 328 | UUCUGGAAUUCUGUGUGAGGGA | 329 | CCUCACACAGAAUUCCAGAAUU |
| hsa-miR-1301 | 330 | CGCUCUAGGCACCGCAGCA | 331 | UUGCAGCUGCCUGGGAGUGACUUC |
| hsa-miR-1302 | 332 | UUGGGACAUACUUUAUGCUAAA | 333 | UAGCAUAAGUAUGUCCCAAUU |
| hsa-miR-1303 | 334 | UUUAGAGACGGGGUCUUGCUCU | 335 | AGCAAGACCCCGUCUCUAAAUU |
| hsa-miR-1304 | 336 | UUUGAGGCUACAGUGAGAUGUG | 337 | UCUCACUGUAGCCUCGAACCCC |
| hsa-miR-1305 | 338 | UUUUCAACUCUAAUGGGAGAGA | 339 | UCUCCCAUUAGAGUUGAAAAUU |
| hsa-miR-1306 | 340 | CCACCUCCCCUGCAAACGUCCA | 341 | ACGUUGGCUCUGGUGGUG |
| hsa-miR-1307 | 342 | ACUCGGCGUGGCGUCGGUCGUG | 343 | UCGACCGGACCUCGACCGGCU |
| hsa-miR-130a | 344 | UUCACAUUGUGCUACUGUCUGC | 345 | CAGUGCAAUGUUAAAAGGGCAU |
| hsa-miR-130b | 346 | CAGUGCAAUGAUGAAAGGGCAU | 347 | ACUCUUUCCCUGUUGCACUAC |
| hsa-miR-132 | 348 | UAACAGUCUACAGCCAUGGUCG | 349 | ACCGUGGCUUUCGAUUGUUACU |
| hsa-miR-1321 | 350 | CAGGGAGGUGAAUGUGAU | 351 | CACAUUCACCUCCCUGUU |
| hsa-miR-1322 | 352 | GAUGAUGCUGCUGAUGCUG | 353 | GCAUCAGCAGCAUCAUCUU |
| hsa-miR-1323 | 354 | UCAAAACUGAGGGGCAUUUUCU | 355 | AAAAUGCCCCUCAGUUUUGAUU |
| hsa-miR-1324 | 356 | CCAGACAGAAUUCUAUGCACUUUC | 357 | AAGUGCAUAGAAUUCUGUCUGGUU |
| hsa-miR-133a | 358 | AGCUGGUAAAAUGGAACCAAAU | 359 | UUUGGUCCCCUUCAACCAGCUG |
| hsa-miR-133b | 360 | UUUGGUCCCCUUCAACCAGCUA | 361 | GCUGGUUGAAGGGGACCAAAUU |
| hsa-miR-134 | 362 | UGUGACUGGUUGACCAGAGGGG | 363 | CCUGUGGGCCACCUAGUCACCAA |
| hsa-miR-1343 | 364 | CUCCUGGGGCCCGCACUCUCGC | 365 | UGGGGAGCGGCCCCCGGGUGGG |
| hsa-miR-135a | 366 | UAUAGGGAUUGGAGCCGUGGCG | 367 | UAUGGCUUUUUAUUCCUAUGUGA |
| hsa-miR-135b | 368 | AUGUAGGGCUAAAAGCCAUGGG | 369 | UAUGGCUUUUCAUUCCUAUGUGA |
| hsa-miR-136 | 370 | CAUCAUCGUCUCAAAUGAGUCU | 371 | ACUCCAUUUGUUUUGAUGAUGGA |
| hsa-miR-137 | 372 | UUAUUGCUUAAGAAUACGCGUAG | 373 | ACGCGUAUUCUUAAGCAAUAAUU |
| hsa-miR-138-1 | 374 | AGCUGGUGUUGUGAAUCAGGCCG | 375 | GCUACUUCACAACACCAGGGCC |
| hsa-miR-138-2 | 376 | AGCUGGUGUUGUGAAUCAGGCCG | 377 | GCUAUUUCACGACACCAGGGUU |
| hsa-miR-139 | 378 | UCUACAGUGCACGUGUCUCCAGU | 379 | UGGAGACGCGGCCCUGUUGGAGU |
| hsa-miR-140 | 380 | CAGUGGUUUUACCCUAUGGUAG | 381 | UACCACAGGGUAGAACCACGG |
| hsa-miR-141 | 382 | UAACACUGUCUGGUAAAGAUGG | 383 | CAUCUUCCAGUACAGUGUUGGA |
| hsa-miR-142 | 384 | CAUAAAGUAGAAAGCACUACU | 385 | UGUAGUGUUUCCUACUUUAUGGA |

TABLE 1-continued miRNA Sequences

| miRNA | SEQ ID NO: | Sequence 1 | SEQ ID NO: | Sequence 2 |
|---|---|---|---|---|
| hsa-miR-143 | 386 | GGUGCAGUGCUGCAUCUCUGGU | 387 | UGAGAUGAAGCACUGUAGCUC |
| hsa-miR-144 | 388 | UACAGUAUAGAUGAUGUACU | 389 | GGAUAUCAUCAUAUACUGUAAG |
| hsa-miR-145 | 390 | GUCCAGUUUUCCCAGGAAUCCCU | 391 | GGAUUCCUGGAAAUACUGUUCU |
| hsa-miR-1468 | 392 | CUCCGUUUGCCUGUUUCGCUG | 393 | AGCAAAAUAAGCAAAUGGAAAA |
| hsa-miR-1469 | 394 | CUCGGCGCGGGGCGCGGGCUCC | 395 | AGCCCGCGCCCCGCGCCGAGUU |
| hsa-miR-146a | 396 | UGAGAACUGAAUUCCAUGGGUU | 397 | CCUCUGAAAUUCAGUUCUUCAG |
| hsa-miR-146b | 398 | UGCCCUGUGGACUCAGUUCUGG | 399 | UGAGAACUGAAUUCCAUAGGCU |
| hsa-miR-1470 | 400 | GCCCUCCGCCCGUGCACCCCG | 401 | GGGUGCACGGGCGGAGGGCUU |
| hsa-miR-1471 | 402 | GCCCGCGUGUGGAGCCAGGUGU | 403 | ACCUGGCUCCACACGCGGGCUU |
| hsa-miR-147a | 404 | GUGUGUGGAAAUGCUUCUGC | 405 | AGAAGCAUUUCCACACACUU |
| hsa-miR-147b | 406 | GUGUGCGGAAAUGCUUCUGCUA | 407 | GCAGAAGCAUUUCCGCACACUU |
| hsa-miR-148a | 408 | AAAGUUCUGAGACACUCCGACU | 409 | UCAGUGCACUACAGAACUUUGU |
| hsa-miR-148b | 410 | AAGUUCUGUUAUACACUCAGGC | 411 | UCAGUGCAUCACAGAACUUUGU |
| hsa-miR-149 | 412 | AGGGAGGGACGGGGGCUGUGC | 413 | UCUGGCUCCGUGUCUUCACUCCC |
| hsa-miR-150 | 414 | CUGGUACAGGCCUGGGGGACAG | 415 | UCUCCCAACCCUUGUACCAGUG |
| hsa-miR-151a | 416 | UCGAGGAGCUCACAGUCUAGU | 417 | CUAGACUGAAGCUCCUUGAGG |
| hsa-miR-151b | 418 | UCGAGGAGCUCACAGUCU | 419 | ACUGUGAGCUCCUCGAUU |
| hsa-miR-152 | 420 | AGGUUCUGUGAUACACUCCGACU | 421 | UCAGUGCAUGACAGAACUUGG |
| hsa-miR-153 | 422 | UCAUUUUUGUGAUGUUGCAGCU | 423 | UUGCAUAGUCACAAAAGUGAUC |
| hsa-miR-1537 | 424 | AGCUGUAAUUAGUCAGUUUUCU | 425 | AAAACCGUCUAGUUACAGUUGU |
| hsa-miR-1538 | 426 | CGGCCCGGGCUGCUGCUGUUCCU | 427 | GAACAGCAGCAGCCCGGGCCGUU |
| hsa-miR-1539 | 428 | UCCUGCGCGUCCCAGAUGCCC | 429 | GCAUCUGGGACGCGCAGGAUU |
| hsa-miR-154 | 430 | AAUCAUACACGGUUGACCUAUU | 431 | UAGGUUAUCCGUGUUGCCUUCG |
| hsa-miR-155 | 432 | CUCCUACAUAUUAGCAUUAACA | 433 | UUAAUGCUAAUCGUGAUAGGGGU |
| hsa-miR-1587 | 434 | UUGGGCUGGGCUGGGUUGGG | 435 | CAACCCAGCCCAGCCCAAUU |
| hsa-miR-15a | 436 | CAGGCCAUAUUGUGCUGCCUCA | 437 | UAGCAGCACAUAAUGGUUUGUG |
| hsa-miR-15b | 438 | CGAAUCAUUAUUUGCUGCUCUA | 439 | UAGCAGCACAUCAUGGUUUACA |
| hsa-miR-16-1 | 440 | UAGCAGCACGUAAAUAUUGGCG | 441 | CCAGUAUUAACUGUGCUGCUGA |
| hsa-miR-16-2 | 442 | UAGCAGCACGUAAAUAUUGGCG | 443 | CCAAUAUUACUGUGCUGCUUUA |
| hsa-miR-17 | 444 | ACUGCAGUGAAGGCACUUGUAG | 445 | CAAAGUGCUUACAGUGCAGGUAG |
| hsa-miR-181a-1 | 446 | AACAUUCAACGCUGUCGGUGAGU | 447 | ACCAUCGACCGUUGAUUGUACC |
| hsa-miR-181a-2 | 448 | AACAUUCAACGCUGUCGGUGAGU | 449 | ACCACUGACCGUUGACUGUACC |
| hsa-miR-181b-1 | 450 | AACAUUCAUUGCUGUCGGUGGGU | 451 | CUCACUGAACAAUGAAUGCAA |
| hsa-miR-181b-2 | 452 | AACAUUCAUUGCUGUCGGUGGGU | 453 | CUCACUGAUCAAUGAAUGCA |
| hsa-miR-181c | 454 | AACCAUCGACCGUUGAGUGGAC | 455 | AACAUUCAACCUGUCGGUGAGU |
| hsa-miR-181d | 456 | CCACCGGGGGAUGAAUGUCAC | 457 | AACAUUCAUUGUUGUCGGUGGGU |
| hsa-miR-182 | 458 | UUUGGCAAUGGUAGAACUCACACU | 459 | UGGUUCUAGACUUGCCAACUA |

TABLE 1-continued miRNA Sequences

| miRNA | SEQ ID NO: | Sequence 1 | SEQ ID NO: | Sequence 2 |
|---|---|---|---|---|
| hsa-miR-1825 | 460 | UCCAGUGCCCUCCUCUCC | 461 | AGAGGAGGGCACUGGAUU |
| hsa-miR-1827 | 462 | UGAGGCAGUAGAUUGAAU | 463 | UCAAUCUACUGCCUCAUU |
| hsa-miR-183 | 464 | UAUGGCACUGGUAGAAUUCACU | 465 | GUGAAUUACCGAAGGGCCAUAA |
| hsa-miR-184 | 466 | UGGACGGAGAACUGAUAAGGGU | 467 | CCUUAUCAGUUCUCCGUCCAUU |
| hsa-miR-185 | 468 | AGGGGCUGGCUUUCCUCUGGUC | 469 | UGGAGAGAAAGGCAGUUCCUGA |
| hsa-miR-186 | 470 | CAAAGAAUUCUCCUUUUGGGCU | 471 | GCCCAAAGGUGAAUUUUUGGG |
| hsa-miR-187 | 472 | UCGUGUCUUGUGUUGCAGCCGG | 473 | GGCUACAACACAGGACCCGGGC |
| hsa-miR-188 | 474 | CAUCCCUUGCAUGGUGGAGGG | 475 | CUCCCACAUGCAGGGUUUGCA |
| hsa-miR-18a | 476 | UAAGGUGCAUCUAGUGCAGAUAG | 477 | ACUGCCCUAAGUGCUCCUUCUGG |
| hsa-miR-18b | 478 | UAAGGUGCAUCUAGUGCAGUUAG | 479 | UGCCCUAAAUGCCCCUUCUGGC |
| hsa-miR-1908 | 480 | CGGCGGGGACGGCGAUUGGUC | 481 | CCGGCCGCCGGCUCCGCCCCG |
| hsa-miR-1909 | 482 | CGCAGGGGCCGGGUGCUCACCG | 483 | UGAGUGCCGGUGCCUGCCCUG |
| hsa-miR-190a | 484 | UGAUAUGUUUGAUAUAUUAGGU | 485 | CUAUAUAUCAAACAUAUUCCU |
| hsa-miR-190b | 486 | UGAUAUGUUUGAUAUUGGGUU | 487 | CCCAAUAUCAAACAUAUCAUU |
| hsa-miR-191 | 488 | GCUGCGCUUGGAUUUCGUCCCC | 489 | CAACGGAAUCCCAAAAGCAGCUG |
| hsa-miR-1910 | 490 | CCAGUCCUGUGCCUGCCGCCU | 491 | GAGGCAGAAGCAGGAUGACA |
| hsa-miR-1911 | 492 | CACCAGGCAUUGUGGUCUCC | 493 | UGAGUACCGCCAUGUCUGUUGGG |
| hsa-miR-1912 | 494 | UACCCAGAGCAUGCAGUGUGAA | 495 | CACACUGCAUGCUCUGGGUAUU |
| hsa-miR-1913 | 496 | UCUGCCCCCUCCGCUGCUGCCA | 497 | GCAGCAGCGGAGGGGCAGAUU |
| hsa-miR-1914 | 498 | CCCUGUGCCCGGCCCACUUCUG | 499 | GGAGGGGUCCCGCACUGGGAGG |
| hsa-miR-1915 | 500 | ACCUUGCCUUGCUGCCCGGGCC | 501 | CCCCAGGGCGACGCGGCGGG |
| hsa-miR-192 | 502 | CUGCCAAUUCCAUAGGUCACAG | 503 | CUGACCUAUGAAUUGACAGCC |
| hsa-miR-193a | 504 | UGGGUCUUUGCGGGCGAGAUGA | 505 | AACUGGCCUACAAAGUCCCAGU |
| hsa-miR-193b | 506 | CGGGGUUUUGAGGGCGAGAUGA | 507 | AACUGGCCCUCAAAGUCCCGCU |
| hsa-miR-194 | 508 | UGUAACAGCAACUCCAUGUGGA | 509 | CCAGUGGGGCUGCUGUUAUCUG |
| hsa-miR-195 | 510 | UAGCAGCACAGAAAUAUUGGC | 511 | CCAAUAUUGGCUGUGCUGCUCC |
| hsa-miR-196a | 512 | UAGGUAGUUUCAUGUUGUUGGG | 513 | CGGCAACAAGAAACUGCCUGAG |
| hsa-miR-196b | 514 | UCGACAGCACGACACUGCCUUC | 515 | UAGGUAGUUUCCUGUUGUUGGG |
| hsa-miR-197 | 516 | CGGGUAGAGAGGGCAGUGGGAGG | 517 | UUCACCACCUUCUCCACCCAGC |
| hsa-miR-1972 | 518 | UCAGGCCAGGCACAGUGGCUCA | 519 | AGCCACUGUGCCUGGCCUGAUU |
| hsa-miR-1973 | 520 | ACCGUGCAAAGGUAGCAUA | 521 | UGCUACCUUUGCACGGUUU |
| hsa-miR-1976 | 522 | CCUCCUGCCCUCCUUGCUGU | 523 | AGCAAGGAGGGCAGGAGGUU |
| hsa-miR-198 | 524 | GGUCCAGAGGGGAGAUAGGUUC | 525 | ACCUAUCUCCCCUCUGGACCUU |
| hsa-miR-199a | 526 | ACAGUAGUCUGCACAUUGGUUA | 527 | CCCAGUGUUCAGACUACCUGUUC |
| hsa-miR-199b | 528 | CCCAGUGUUUAGACUAUCUGUUC | 529 | ACAGUAGUCUGCACAUUGGUUA |
| hsa-miR-19a | 530 | UGUGCAAAUCUAUGCAAAACUGA | 531 | AGUUUUGCAUAGUUGCACUACA |
| hsa-miR-19b-1 | 532 | UGUGCAAAUCCAUGCAAAACUGA | 533 | AGUUUUGCAGGUUUGCAUCCAGC |
| hsa-miR-19b-2 | 534 | UGUGCAAAUCCAUGCAAAACUGA | 535 | AGUUUUGCAGGUUUGCAUUUCA |

TABLE 1-continued miRNA Sequences

| miRNA | SEQ ID NO: | Sequence 1 | SEQ ID NO: | Sequence 2 |
|---|---|---|---|---|
| hsa-miR-200a | 536 | UAACACUGUCUGGUAACGAUGU | 537 | CAUCUUACCGGACAGUGCUGGA |
| hsa-miR-200b | 538 | CAUCUUACUGGGCAGCAUUGGA | 539 | UAAUACUGCCUGGUAAUGAUGA |
| hsa-miR-200c | 540 | UAAUACUGCCGGGUAAUGAUGGA | 541 | CGUCUUACCCAGCAGUGUUUGG |
| hsa-miR-202 | 542 | UUCCUAUGCAUAUACUUCUUUG | 543 | AGAGGUAUAGGGCAUGGGAA |
| hsa-miR-203a | 544 | AGUGGUUCUUAACAGUUCAACAGUU | 545 | GUGAAAUGUUUAGGACCACUAG |
| hsa-miR-203b | 546 | UAGUGGUCCUAAACAUUUCACA | 547 | UUGAACUGUUAAGAACCACUGGA |
| hsa-miR-204 | 548 | GCUGGGAAGGCAAAGGGACGU | 549 | UUCCCUUUGUCAUCCUAUGCCU |
| hsa-miR-205 | 550 | UCCUUCAUUCCACCGGAGUCUG | 551 | GAUUUCAGUGGAGUGAAGUUC |
| hsa-miR-2052 | 552 | UGUUUUGAUAACAGUAAUGU | 553 | AUUACUGUUAUCAAAACAUU |
| hsa-miR-2053 | 554 | GUGUUAAUUAAACCUCUAUUUAC | 555 | AAAUAGAGGUUUAAUUAACACUU |
| hsa-miR-2054 | 556 | CUGUAAUAUAAAUUUAAUUUAUU | 557 | UAAAUUAAAUUUAUAUUACAGUU |
| hsa-miR-206 | 558 | UGGAAUGUAAGGAAGUGUGUGG | 559 | ACACACUUCCUUACAUUCCAUU |
| hsa-miR-208a | 560 | AUAAGACGAGCAAAAAGCUUGU | 561 | GAGCUUUUGGCCCGGGUUAUAC |
| hsa-miR-208b | 562 | AAGCUUUUUGCUCGAAUUAUGU | 563 | AUAAGACGAACAAAAGGUUUGU |
| hsa-miR-20a | 564 | UAAAGUGCUUAUAGUGCAGGUAG | 565 | ACUGCAUUAUGAGCACUUAAAG |
| hsa-miR-20b | 566 | CAAAGUGCUCAUAGUGCAGGUAG | 567 | ACUGUAGUAUGGGCACUUCCAG |
| hsa-miR-21 | 568 | UAGCUUAUCAGACUGAUGUUGA | 569 | CAACACCAGUCGAUGGGCUGU |
| hsa-miR-210 | 570 | AGCCCCUGCCCACCGCACACUG | 571 | CUGUGCGUGUGACAGCGGCUGA |
| hsa-miR-211 | 572 | GCAGGGACAGCAAAGGGGUGC | 573 | UUCCCUUUGUCAUCCUUCGCCU |
| hsa-miR-2110 | 574 | UUGGGGAAACGGCCGCUGAGUG | 575 | CUCAGCGGCCGUUUCCCCAAUU |
| hsa-miR-2113 | 576 | AUUUGUGCUUGGCUCUGUCAC | 577 | GACAGAGCCAAGCACAAAUUU |
| hsa-miR-2114 | 578 | UAGUCCCUUCCUUGAAGCGGUC | 579 | CGAGCCUCAAGCAAGGGACUU |
| hsa-miR-2115 | 580 | CAUCAGAAUUCAUGGAGGCUAG | 581 | AGCUUCCAUGACUCCUGAUGGA |
| hsa-miR-2116 | 582 | GGUUCUUAGCAUAGGAGGUCU | 583 | CCUCCCAUGCCAAGAACUCCC |
| hsa-miR-2117 | 584 | UGUUCUCUUUGCCAAGGACAG | 585 | GUCCUUGGCAAAGAGAACAUU |
| hsa-miR-212 | 586 | UAACAGUCUCCAGUCACGGCC | 587 | ACCUUGGCUCUAGACUGCUUACU |
| hsa-miR-214 | 588 | UGCCUGUCUACACUUGCUGUGC | 589 | ACAGCAGGCACAGACAGGCAGU |
| hsa-miR-215 | 590 | UCUGUCAUUUCUUUAGGCCAAUA | 591 | AUGACCUAUGAAUUGACAGAC |
| hsa-miR-216a | 592 | UAAUCUCAGCUGGCAACUGUGA | 593 | UCACAGUGGUCUCUGGGAUUAU |
| hsa-miR-216b | 594 | AAAUCUCUGCAGGCAAAUGUGA | 595 | ACACACUUACCCGUAGAGAUUCUA |
| hsa-miR-217 | 596 | UACUGCAUCAGGAACUGAUUGGA | 597 | CAAUCAGUUCCUGAUGCAGUAUU |
| hsa-miR-218-1 | 598 | UUGUGCUUGAUCUAACCAUGU | 599 | AUGGUUCCGUCAAGCACCAUGG |
| hsa-miR-218-2 | 600 | UUGUGCUUGAUCUAACCAUGU | 601 | CAUGGUUCUGUCAAGCACCGCG |
| hsa-miR-219a-1 | 602 | UGAUUGUCCAAACGCAAUUCU | 603 | AGAGUUGAGUCUGGACGUCCCG |
| hsa-miR-219a-2 | 604 | UGAUUGUCCAAACGCAAUUCU | 605 | AGAAUUGUGGCUGGACAUCUGU |
| hsa-miR-219b | 606 | AGAUGUCCAGCCACAAUUCUCG | 607 | AGAAUUGCGUUUGGACAAUCAGU |
| hsa-miR-22 | 608 | AGUUCUUCAGUGGCAAGCUUUA | 609 | AAGCUGCCAGUUGAAGAACUGU |

TABLE 1-continued miRNA Sequences

| miRNA | SEQ ID NO: | Sequence 1 | SEQ ID NO: | Sequence 2 |
|---|---|---|---|---|
| hsa-miR-221 | 610 | AGCUACAUUGUCUGCUGGGUUUC | 611 | ACCUGGCAUACAAUGUAGAUUU |
| hsa-miR-222 | 612 | AGCUACAUCUGGCUACUGGGU | 613 | CUCAGUAGCCAGUGUAGAUCCU |
| hsa-miR-223 | 614 | CGUGUAUUUGACAAGCUGAGUU | 615 | UGUCAGUUUGUCAAAUACCCCA |
| hsa-miR-224 | 616 | AAAAUGGUGCCCUAGUGACUACA | 617 | CAAGUCACUAGUGGUUCCGUU |
| hsa-miR-2276 | 618 | GCCCUCUGUCACCUUGCAGACG | 619 | UCUGCAAGUGUCAGAGGCGAGG |
| hsa-miR-2277 | 620 | AGCGCGGGCUGAGCGCUGCCAGUC | 621 | UGACAGCGCCCUGCCUGGCUC |
| hsa-miR-2278 | 622 | GAGAGCAGUGUGUGUUGCCUGG | 623 | AGGCAACACACACUGCUCUCUU |
| hsa-miR-2355 | 624 | AUCCCCAGAUACAAUGGACAA | 625 | AUUGUCCUUGCUGUUUGGAGAU |
| hsa-miR-2392 | 626 | UAGGAUGGGGUGAGAGGUG | 627 | CCUCUCACCCCAUCCUAUU |
| hsa-miR-23a | 628 | AUCACAUUGCCAGGGAUUUCC | 629 | GGGGUUCCUGGGGAUGGGAUUU |
| hsa-miR-23b | 630 | AUCACAUUGCCAGGGAUUACC | 631 | UGGGUUCCUGGCAUGCUGAUUU |
| hsa-miR-23c | 632 | AUCACAUUGCCAGUGAUUACCC | 633 | GUAAUCACUGGCAAUGUGAUUU |
| hsa-miR-24-1 | 634 | UGGCUCAGUUCAGCAGGAACAG | 635 | UGCCUACUGAGCUGAUAUCAGU |
| hsa-miR-24-2 | 636 | UGGCUCAGUUCAGCAGGAACAG | 637 | UGCCUACUGAGCUGAAACACAG |
| hsa-miR-2467 | 638 | AGCAGAGGCAGAGAGGCUCAGG | 639 | UGAGGCUCUGUUAGCCUUGGCUC |
| hsa-miR-25 | 640 | AGGCGGAGACUUGGGCAAUUG | 641 | CAUUGCACUUGUCUCGGUCUGA |
| hsa-miR-2681 | 642 | GUUUUACCACCUCCAGGAGACU | 643 | UAUCAUGGAGUUGGUAAAGCAC |
| hsa-miR-2682 | 644 | CGCCUCUUCAGCGCUGUCUUCC | 645 | CAGGCAGUGACUGUUCAGACGUC |
| hsa-miR-26a-1 | 646 | UUCAAGUAAUCCAGGAUAGGCU | 647 | CCUAUUCUUGGUUACUUGCACG |
| hsa-miR-26a-2 | 648 | UUCAAGUAAUCCAGGAUAGGCU | 649 | CCUAUUCUUGAUUACUUGUUUC |
| hsa-miR-26b | 650 | UUCAAGUAAUUCAGGAUAGGU | 651 | CCUGUUCUCCAUUACUUGGCUC |
| hsa-miR-27a | 652 | UUCACAGUGGCUAAGUUCCGC | 653 | AGGGCUUAGCUGCUUGUGAGCA |
| hsa-miR-27b | 654 | UUCACAGUGGCUAAGUUCUGC | 655 | AGAGCUUAGCUGAUUGGUGAAC |
| hsa-miR-28 | 656 | CACUAGAUUGUGAGCUCCUGGA | 657 | AAGGAGCUCACAGUCUAUUGAG |
| hsa-miR-2861 | 658 | GGGGCCUGGCGGUGGGCGG | 659 | GCCCACCGCCAGGCCCCUU |
| hsa-miR-2909 | 660 | GUUAGGGCCAACAUCUCUUGG | 661 | AAGAGAUGUUGGCCCUAACUU |
| hsa-miR-296 | 662 | GAGGGUUGGGUGGAGGCUCUCC | 663 | AGGGCCCCCCCUCAAUCCUGU |
| hsa-miR-297 | 664 | AUGUAUGUGUGCAUGUGCAUG | 665 | UGCACAUGCACACAUACAUUU |
| hsa-miR-298 | 666 | AGCAGAAGCAGGGAGGUUCUCCCA | 667 | GGAGAACCUCCCUGCUUCUGCUUU |
| hsa-miR-299 | 668 | UGGUUUACCGUCCCACAUACAU | 669 | UAUGUGGGAUGGUAAACCGCUU |
| hsa-miR-29a | 670 | ACUGAUUUCUUUUGGUGUUCAG | 671 | UAGCACCAUCUGAAAUCGGUUA |
| hsa-miR-29b-1 | 672 | UAGCACCAUUUGAAAUCAGUGUU | 673 | GCUGGUUUCAUAUGGUGGUUUAGA |
| hsa-miR-29b-2 | 674 | UAGCACCAUUUGAAAUCAGUGUU | 675 | CUGGUUUCACAUGGUGGCUUAG |
| hsa-miR-29c | 676 | UGACCGAUUUCUCCUGGUGUUC | 677 | UAGCACCAUUUGAAAUCGGUUA |
| hsa-miR-300 | 678 | UAUACAAGGGCAGACUCUCUCU | 679 | AGAGAGUCUGCCCUUGUAUAUU |
| hsa-miR-301a | 680 | GCUCUGACUUUAUUGCACUACU | 681 | CAGUGCAAUAGUAUUGUCAAAGC |
| hsa-miR-301b | 682 | CAGUGCAAUGAUAUUGUCAAAGC | 683 | GCUCUGACGAGGUUGCACUACU |
| hsa-miR-302a | 684 | UAAGUGCUUCCAUGUUUUGGUGA | 685 | ACUUAAACGUGGAUGUACUUGCU |

TABLE 1-continued miRNA Sequences

| miRNA | SEQ ID NO: | Sequence 1 | SEQ ID NO: | Sequence 2 |
|---|---|---|---|---|
| hsa-miR-302b | 686 | UAAGUGCUUCCAUGUUUUAGUAG | 687 | ACUUUAACAUGGAAGUGCUUUC |
| hsa-miR-302c | 688 | UUUAACAUGGGGGUACCUGCUG | 689 | UAAGUGCUUCCAUGUUUCAGUGG |
| hsa-miR-302d | 690 | ACUUUAACAUGGAGGCACUUGC | 691 | UAAGUGCUUCCAUGUUUGAGUGU |
| hsa-miR-302e | 692 | UAAGUGCUUCCAUGCUU | 693 | GCAUGGAAGCACUUAUU |
| hsa-miR-302f | 694 | UAAUUGCUUCCAUGUUU | 695 | ACAUGGAAGCAAUUAUU |
| hsa-miR-3064 | 696 | UUGCCACACUGCAACACCUUACA | 697 | UCUGGCUGUUGUGGUGUGCAA |
| hsa-miR-3065 | 698 | UCAGCACCAGGAUAUUGUUGGAG | 699 | UCAACAAAUCACUGAUGCUGGA |
| hsa-miR-3074 | 700 | GAUAUCAGCUCAGUAGGCACCG | 701 | GUUCCUGCUGAACUGAGCCAG |
| hsa-miR-30a | 702 | CUUUCAGUCGGAUGUUUGCAGC | 703 | UGUAAACAUCCUCGACUGGAAG |
| hsa-miR-30b | 704 | UGUAAACAUCCUACACUCAGCU | 705 | CUGGGAGGUGGAUGUUUACUUC |
| hsa-miR-30c-1 | 706 | UGUAAACAUCCUACACUCUCAGC | 707 | CUGGGAGAGGGUUGUUUACUCC |
| hsa-miR-30c-2 | 708 | UGUAAACAUCCUACACUCUCAGC | 709 | CUGGGAGAAGGCUGUUUACUCU |
| hsa-miR-30d | 710 | UGUAAACAUCCCCGACUGGAAG | 711 | CUUUCAGUCAGAUGUUUGCUGC |
| hsa-miR-30e | 712 | UGUAAACAUCCUUGACUGGAAG | 713 | CUUUCAGUCGGAUGUUUACAGC |
| hsa-miR-31 | 714 | UGCUAUGCCAACAUAUUGCCAU | 715 | AGGCAAGAUGCUGGCAUAGCU |
| hsa-miR-3115 | 716 | AUAUGGGUUUACUAGUUGGU | 717 | CAACUAGUAAACCCAUAUUU |
| hsa-miR-3116 | 718 | UGCCUGGAACAUAGUAGGGACU | 719 | UCCCUACUAUGUUCCAGGCAUU |
| hsa-miR-3117 | 720 | AUAGGACUCAUAUAGUGCCAG | 721 | AGACACUAUACGAGUCAUAU |
| hsa-miR-3118 | 722 | UGUGACUGCAUUAUGAAAAUUCU | 723 | AAUUUUCAUAAUGCAGUCACAUU |
| hsa-miR-3119 | 724 | UGGCUUUUAACUUUGAUGGC | 725 | CAUCAAAGUUAAAAGCCAUU |
| hsa-miR-3120 | 726 | CCUGUCUGUGCCUGCUGUACA | 727 | CACAGCAAGUGUAGACAGGCA |
| hsa-miR-3121 | 728 | UCCUUUGCCUAUUCUAUUUAAG | 729 | UAAAUAGAGUAGGCAAAGGACA |
| hsa-miR-3122 | 730 | GUUGGGACAAGAGGACGGUCUU | 731 | GACCGUCCUCUUGUCCCAACUU |
| hsa-miR-3123 | 732 | CAGAGAAUUGUUUAAUC | 733 | UUAAACAAUUCUCUGUU |
| hsa-miR-3124 | 734 | UUCGCGGGCGAAGGCAAAGUC | 735 | ACUUCCUCACUCCCGUGAAGU |
| hsa-miR-3125 | 736 | UAGAGGAAGCUGUGGAGAGA | 737 | UCUCCACAGCUUCCUCUAUU |
| hsa-miR-3126 | 738 | CAUCUGGCAUCCGUCACACAGA | 739 | UGAGGGACAGAUGCCAGAAGCA |
| hsa-miR-3127 | 740 | UCCCCUUCUGCAGGCCUGCUGG | 741 | AUCAGGGCUUGUGGAAUGGGAAG |
| hsa-miR-3128 | 742 | UCUGGCAAGUAAAAAACUCUCAU | 743 | GAGAGUUUUUACUUGCCAGAUU |
| hsa-miR-3129 | 744 | GCAGUAGUGUAGAGAUUGGUUU | 745 | AAACUAAUCUCUACACUGCUGC |
| hsa-miR-3130 | 746 | GCUGCACCGGAGACUGGGUAA | 747 | UACCCAGUCUCCGGUGCAGCC |
| hsa-miR-3131 | 748 | UCGAGGACUGGUGGAAGGGCCUU | 749 | GGCCCUUCCACCAGUCCUCGAUU |
| hsa-miR-3132 | 750 | UGGGUAGAGAAGGAGCUCAGAGGA | 751 | CUCUGAGCUCCUUCUCUACCCAUU |
| hsa-miR-3133 | 752 | UAAAGAACUCUUAAAACCCAAU | 753 | UGGGUUUAAGAGUUCUUUAUU |
| hsa-miR-3134 | 754 | UGAUGGAUAAAGACUACAUAUU | 755 | UAUGUAGUCUUUUAUCCAUCAUU |
| hsa-miR-3135a | 756 | UGCCUAGGCUGAGACUGCAGUG | 757 | CUGCAGUCUCAGCCUAGGCAUU |
| hsa-miR-3135b | 758 | GGCUGGAGCGAGUGCAGUGGUG | 759 | CCACUGCACUCGCUCCAGCCUU |

TABLE 1-continued miRNA Sequences

| miRNA | SEQ ID NO: | Sequence 1 | SEQ ID NO: | Sequence 2 |
|---|---|---|---|---|
| hsa-miR-3136 | 760 | CUGACUGAAUAGGUAGGGUCAUU | 761 | UGGCCCAACCUAUUCAGUUAGU |
| hsa-miR-3137 | 762 | UCUGUAGCCUGGGAGCAAUGGGGU | 763 | CCCAUUGCUCCCAGGCUACAGAUU |
| hsa-miR-3138 | 764 | UGUGGACAGUGAGGUAGAGGGAGU | 765 | UCCCUCUACCUCACUGUCCACAUU |
| hsa-miR-3139 | 766 | UAGGAGCUCAACAGAUGCCUGUU | 767 | CAGGCAUCUGUUGAGCUCCUAUU |
| hsa-miR-3140 | 768 | ACCUGAAUUACCAAAAGCUUU | 769 | AGCUUUUGGGAAUUCAGGUAGU |
| hsa-miR-3141 | 770 | GAGGGCGGGUGGAGGAGGA | 771 | CUCCUCCACCCGCCCUCUU |
| hsa-miR-3142 | 772 | AAGGCCUUUCUGAACCUUCAGA | 773 | UGAAGGUUCAGAAAGGCCUUUU |
| hsa-miR-3143 | 774 | AUAACAUUGUAAAGCGCUUCUUUCG | 775 | AAAGAAGCGCUUUACAAUGUUAUUU |
| hsa-miR-3144 | 776 | AUAUACCUGUUCGGUCUCUUUA | 777 | AGGGGACCAAAGAGAUAUAUAG |
| hsa-miR-3145 | 778 | AGAUAUUUUGAGUGUUUGGAAUUG | 779 | AACUCCAAACACUCAAAACUCA |
| hsa-miR-3146 | 780 | CAUGCUAGGAUAGAAAGAAUGG | 781 | AUUCUUUCUAUCCUAGCAUGUU |
| hsa-miR-3147 | 782 | GGUUGGGCAGUGAGGAGGGUGUGA | 783 | ACACCUCCUCACUGCCCAACCUU |
| hsa-miR-3148 | 784 | UGGAAAAAACUGGUGUGUGCUU | 785 | GCACACACCAGUUUUUUCCAUU |
| hsa-miR-3149 | 786 | UUUGUAUGGAUAUGUGUGUAU | 787 | ACACACAUAUCCAUACAAAUU |
| hsa-miR-3150a | 788 | CAACCUCGACGAUCUCCUCAGC | 789 | CUGGGGAGAUCCUCGAGGUUGG |
| hsa-miR-3150b | 790 | CAACCUCGAGGAUCUCCCCAGC | 791 | UGAGGAGAUCGUCGAGGUUGG |
| hsa-miR-3151 | 792 | GGUGGGGCAAUGGGAUCAGGU | 793 | CCUGAUCCCACAGCCCACCU |
| hsa-miR-3152 | 794 | AUUGCCUCUGUUCUAACACAAG | 795 | UGUGUUAGAAUAGGGGCAAUAA |
| hsa-miR-3153 | 796 | GGGGAAAGCGAGUAGGGACAUUU | 797 | AUGUCCCUACUCGCUUUCCCCUU |
| hsa-miR-3154 | 798 | CAGAAGGGGAGUUGGGAGCAGA | 799 | UGCUCCCAACUCCCCUUCUGUU |
| hsa-miR-3155a | 800 | CCAGGCUCUGCAGUGGGAACU | 801 | UUCCCACUGCAGAGCCUGGUU |
| hsa-miR-3155b | 802 | CCAGGCUCUGCAGUGGGA | 803 | CCACUGCAGAGCCUGGUU |
| hsa-miR-3156 | 804 | CUCCCACUUCCAGAUCUUUCU | 805 | AAAGAUCUGGAAGUGGGAGACA |
| hsa-miR-3157 | 806 | CUGCCCUAGUCUAGCUGAAGCU | 807 | UUCAGCCAGGCUAGUGCAGUCU |
| hsa-miR-3158 | 808 | AAGGGCUUCCUCUCUGCAGGAC | 809 | CCUGCAGAGAGGAAGCCCUUC |
| hsa-miR-3159 | 810 | UAGGAUUACAAGUGUCGGCCAC | 811 | GGCCGACACUUGUAAUCCUAUU |
| hsa-miR-3160 | 812 | AGAGCUGAGACUAGAAAGCCCA | 813 | GGCUUUCUAGUCUCAGCUCUCC |
| hsa-miR-3161 | 814 | CUGAUAAGAACAGAGGCCCAGAU | 815 | CUGGGCCUCUGUUCUUAUCAGUU |
| hsa-miR-3162 | 816 | UUAGGGAGUAGAAGGGUGGGGAG | 817 | UCCCUACCCCUCCACUCCCCA |
| hsa-miR-3163 | 818 | UAUAAAAUGAGGGCAGUAAGAC | 819 | CUUACUGCCCUCAUUUUAUAUU |
| hsa-miR-3164 | 820 | UGUGACUUUAAGGGAAAUGGCG | 821 | CCAUUUCCCUUAAAGUCACAUU |
| hsa-miR-3165 | 822 | AGGUGGAUGCAAUGUGACCUCA | 823 | AGGUCACAUUGCAUCCACCUUU |
| hsa-miR-3166 | 824 | CGCAGACAAUGCCUACUGGCCUA | 825 | GGCCAGUAGGCAUUGUCUGCGUU |
| hsa-miR-3167 | 826 | AGGAUUUCAGAAAUACUGGUGU | 827 | ACCAGUAUUUCUGAAAUCCUUU |
| hsa-miR-3168 | 828 | GAGUUCUACAGUCAGAC | 829 | CUGACUGUAGAACUCUU |
| hsa-miR-3169 | 830 | UAGGACUGUGCUUGGCACAUAG | 831 | AUGUGCCAAGCACAGUCCUAUU |
| hsa-miR-3170 | 832 | CUGGGGUUCUGAGACAGACAGU | 833 | UGUCUGUCUCAGAACCCCAGUU |
| hsa-miR-3171 | 834 | AGAUGUAUGGAAUCUGUAUAUAUC | 835 | UAUAUACAGAUUCCAUACAUCUUU |

TABLE 1-continued miRNA Sequences

| miRNA | SEQ ID NO: | Sequence 1 | SEQ ID NO: | Sequence 2 |
|---|---|---|---|---|
| hsa-miR-3173 | 836 | AAAGGAGGAAAUAGGCAGGCCA | 837 | UGCCCUGCCUGUUUUCUCCUUU |
| hsa-miR-3174 | 838 | UAGUGAGUUAGAGAUGCAGAGCC | 839 | CUCUGCAUCUCUAACUCACUAUU |
| hsa-miR-3175 | 840 | CGGGGAGAGAACGCAGUGACGU | 841 | GUCACUGCGUUCUCUCCCCGUU |
| hsa-miR-3176 | 842 | ACUGGCCUGGGACUACCGG | 843 | GGUAGUCCCAGGCCAGUUU |
| hsa-miR-3177 | 844 | UGUGUACACACGUGCCAGGCGCU | 845 | UGCACGGCACUGGGGACACGU |
| hsa-miR-3178 | 846 | GGGGCGCGGCCGGAUCG | 847 | AUCCGGCCGCGCCCCUU |
| hsa-miR-3179 | 848 | AGAAGGGGUGAAAUUUAAACGU | 849 | GUUUAAAUUUCACCCCUUCUUU |
| hsa-miR-3180 | 850 | CUUCCAGACGCUCCGCCCCACGUCG | 851 | UGGGGCGGAGCUUCCGGAGGCC |
| hsa-miR-3181 | 852 | AUCGGGCCCUCGGCGCCGG | 853 | GGCGCCGAGGGCCCGAUUU |
| hsa-miR-3182 | 854 | GCUUCUGUAGUGUAGUC | 855 | CUACACUACAGAAGCUU |
| hsa-miR-3183 | 856 | GCCUCUCUCGGAGUCGCUCGGA | 857 | CGAGCGACUCCGAGAGAGGCUU |
| hsa-miR-3184 | 858 | AAAGUCUCGCUCUCUGCCCCUCA | 859 | UGAGGGGCCUCAGACCGAGCUUUU |
| hsa-miR-3185 | 860 | AGAAGAAGGCGGUCGGUCUGCGG | 861 | GCAGACCGACCGCCUUCUUCUUU |
| hsa-miR-3186 | 862 | CAGGCGUCUGUCUACGUGGCUU | 863 | UCACGCGGAGAGAUGGCUUUG |
| hsa-miR-3187 | 864 | UUGGCCAUGGGGCUGCGCGG | 865 | CCUGGGCAGCGUGUGGCUGAAGG |
| hsa-miR-3188 | 866 | AGAGGCUUUGUGCGGAUACGGGG | 867 | CCGUAUCCGCACAAAGCCUCUUU |
| hsa-miR-3189 | 868 | CCCUUGGGUCUGAUGGGGUAG | 869 | UGCCCAUCUGUGCCCUGGGUAGGA |
| hsa-miR-3190 | 870 | UGUGGAAGGUAGACGGCCAGAGA | 871 | UCUGGCCAGCUACGUCCCCA |
| hsa-miR-3191 | 872 | CUCUCUGGCCGUCUACCUUCCA | 873 | UGGGGACGUAGCUGGCCAGACAG |
| hsa-miR-3192 | 874 | UCUGGGAGGUUGUAGCAGUGGAA | 875 | CUCUGAUCGCCCUCUCAGCUC |
| hsa-miR-3193 | 876 | UCCUGCGUAGGAUCUGAGGAGU | 877 | UCCUCAGAUCCUACGCAGGAUU |
| hsa-miR-3194 | 878 | AGCUCUGCUGCUCACUGGCAGU | 879 | GGCCAGCCACCAGGAGGGCUG |
| hsa-miR-3195 | 880 | CGCGCCGGGCCCGGGUU | 881 | CCCGGGCCCGGCGCGUU |
| hsa-miR-3196 | 882 | CGGGGCGGCAGGGGCCUC | 883 | GGCCCCUGCCGCCCCGUU |
| hsa-miR-3197 | 884 | GGAGGCGCAGGCUCGGAAAGGCG | 885 | CCUUUCCGAGCCUGCGCCUCCUU |
| hsa-miR-3198 | 886 | GUGGAGUCCUGGGGAAUGGAGA | 887 | UCCAUUCCCAGGACUCCACUU |
| hsa-miR-3199 | 888 | AGGGACUGCCUUAGGAGAAAGUU | 889 | CUUUCUCCUAAGGCAGUCCCUUU |
| hsa-miR-32 | 890 | CAAUUUAGUGUGUGUGAUAUUU | 891 | UAUUGCACAUUACUAAGUUGCA |
| hsa-miR-3200 | 892 | CACCUUGCGCUACUCAGGUCUG | 893 | AAUCUGAGAAGGCGCACAAGGU |
| hsa-miR-3201 | 894 | GGGAUAUGAAGAAAAAU | 895 | UUUUCUUCAUAUCCCUU |
| hsa-miR-3202 | 896 | UGGAAGGGAGAAGAGCUUUAAU | 897 | UAAAGCUCUUCUCCCUUCCAUU |
| hsa-miR-320a | 898 | AAAGCUGGGUUGAGAGGGCGA | 899 | GCCCUCUCAACCCAGCUUUUUU |
| hsa-miR-320b | 900 | AAAAGCUGGGUUGAGAGGGCAA | 901 | GCCCUCUCAACCCAGCUUUUUUU |
| hsa-miR-320c | 902 | AAAAGCUGGGUUGAGAGGGU | 903 | CCUCUCAACCCAGCUUUUUU |
| hsa-miR-320d | 904 | AAAAGCUGGGUUGAGAGGA | 905 | CUCUCAACCCAGCUUUUUU |
| hsa-miR-320e | 906 | AAAGCUGGGUUGAGAAGG | 907 | UUCUCAACCCAGCUUUUU |
| hsa-miR-323a | 908 | AGGUGGUCCGUGGCGCGUUCGC | 909 | CACAUUACACGGUCGACCUCU |

TABLE 1-continued miRNA Sequences

| miRNA | SEQ ID NO: | Sequence 1 | SEQ ID NO: | Sequence 2 |
|---|---|---|---|---|
| hsa-miR-323b | 910 | AGGUUGUCCGUGGUGAGUUCGCA | 911 | CCCAAUACACGGUCGACCUCUU |
| hsa-miR-324 | 912 | CGCAUCCCCUAGGGCAUUGGUGU | 913 | ACUGCCCCAGGUGCUGCUGG |
| hsa-miR-325 | 914 | CCUAGUAGGUGUCCAGUAAGUGU | 915 | ACUUACUGGACACCUACUAGGUU |
| hsa-miR-326 | 916 | CCUCUGGGCCCUUCCUCCAG | 917 | GGAGGAAGGGCCCAGAGGUU |
| hsa-miR-328 | 918 | CUGGCCCUCUCUGCCCUUCCGU | 919 | GGGGGGGCAGGAGGGGCUCAGGG |
| hsa-miR-329 | 920 | AACACACCUGGUUAACCUCUUU | 921 | GAGGUUUUCUGGGUUUCUGUUUC |
| hsa-miR-330 | 922 | GCAAAGCACACGGCCUGCAGAGA | 923 | UCUCUGGGCCUGUGUCUUAGGC |
| hsa-miR-331 | 924 | CUAGGUAUGGUCCCAGGGAUCC | 925 | GCCCCUGGGCCUAUCCUAGAA |
| hsa-miR-335 | 926 | UCAAGAGCAAUAACGAAAAAUGU | 927 | UUUUUCAUUAUUGCUCCUGACC |
| hsa-miR-337 | 928 | GAACGGCUUCAUACAGGAGUU | 929 | CUCCUAUAUGAUGCCUUUCUUC |
| hsa-miR-338 | 930 | UCCAGCAUCAGUGAUUUUGUUG | 931 | AACAAUAUCCUGGUGCUGAGUG |
| hsa-miR-339 | 932 | UGAGCGCCUCGACGACAGAGCCG | 933 | UCCCUGUCCUCCAGGAGCUCACG |
| hsa-miR-33a | 934 | GUGCAUUGUAGUUGCAUUGCA | 935 | CAAUGUUUCCACAGUGCAUCAC |
| hsa-miR-33b | 936 | GUGCAUUGCUGUUGCAUUGC | 937 | CAGUGCCUCGGCAGUGCAGCCC |
| hsa-miR-340 | 938 | UCCGUCUCAGUUACUUUAUAGC | 939 | UUAUAAAGCAAUGAGACUGAUU |
| hsa-miR-342 | 940 | UCUCACACAGAAAUCGCACCCGU | 941 | AGGGGUGCUAUCUGUGAUUGA |
| hsa-miR-345 | 942 | GCCCUGAACGAGGGGUCUGGAG | 943 | GCUGACUCCUAGUCCAGGGCUC |
| hsa-miR-346 | 944 | UGUCUGCCCGCAUGCCUGCCUCU | 945 | AGGCAGGCAUGCGGGCAGACAUU |
| hsa-miR-34a | 946 | UGGCAGUGUCUUAGCUGGUUGU | 947 | CAAUCAGCAAGUAUACUGCC CU |
| hsa-miR-34b | 948 | UAGGCAGUGUCAUUAGCUGAUUG | 949 | CAAUCACUAACUCCACUGCCAU |
| hsa-miR-34c | 950 | AAUCACUAACCACACGGCCAGG | 951 | AGGCAGUGUAGUUAGCUGAUUGC |
| hsa-miR-3529 | 952 | AACAACAAAAUCACUAGUCUUCCA | 953 | AGGUAGACUGGGAUUUGUUGUU |
| hsa-miR-3591 | 954 | AAACACCAUUGUCACACUCCAC | 955 | UUUAGUGUGAUAAUGGCGUUUGA |
| hsa-miR-3605 | 956 | CCUCCGUGUUACCUGUCCUCUAG | 957 | UGAGGAUGGAUAGCAAGGAAGCC |
| hsa-miR-3606 | 958 | UUAGUGAAGGCUAUUUUAAUU | 959 | AAAAUUUCUUUCACUACUUAG |
| hsa-miR-3607 | 960 | ACUGUAAACGCUUUCUGAUG | 961 | GCAUGUGAUGAAGCAAAUCAGU |
| hsa-miR-3609 | 962 | CAAAGUGAUGAGUAAUACUGGCUG | 963 | GCCAGUAUUACUCAUCACUUUGUU |
| hsa-miR-361 | 964 | UCCCCCAGGUGUGAUUCUGAUUU | 965 | UUAUCAGAAUCUCCAGGGGUAC |
| hsa-miR-3610 | 966 | GAAUCGGAAAGGAGGCGCCG | 967 | GCGCCUCCUUUCCGAUUCUU |
| hsa-miR-3611 | 968 | UUGUGAAGAAAGAAAUUCUUA | 969 | AGAAUUUCUUUCUUCACAAUU |
| hsa-miR-3612 | 970 | AGGAGGCAUCUUGAGAAAUGGA | 971 | CAUUUCUCAAGAUGCCUCCUUU |
| hsa-miR-3613 | 972 | UGUUGUACUUUUUUUUUUGUUC | 973 | ACAAAAAAAAAGCCCAACCCUUC |
| hsa-miR-3614 | 974 | CCACUUGGAUCUGAAGGCUGCCC | 975 | UAGCCUUCAGAUCUUGGUGUUU |
| hsa-miR-3615 | 976 | UCUCUCGGCUCCUCGCGGCUC | 977 | GCCGCGAGGAGCCGAGAGAUU |
| hsa-miR-3616 | 978 | AUGAAGUGCACUCAUGAUAUGU | 979 | CGAGGGCAUUUCAUGAUGCAGGC |
| hsa-miR-3617 | 980 | CAUCAGCACCCUAUGUCCUUUCU | 981 | AAAGACAUAGUUCAAGAUGGG |
| hsa-miR-3618 | 982 | UGUCUACAUUAAUGAAAAGAGC | 983 | UCUUUUCAUUAAUGUAGACAUU |
| hsa-miR-3619 | 984 | UCAGCAGGCAGGCUGGUGCAGC | 985 | GGGACCAUCCUGCCUGCUGUGG |

TABLE 1-continued miRNA Sequences

| miRNA | SEQ ID NO: | Sequence 1 | SEQ ID NO: | Sequence 2 |
|---|---|---|---|---|
| hsa-miR-362 | 986 | AACACACCUAUUCAAGGAUUCA | 987 | AAUCCUUGGAACCUAGGUGUGAGU |
| hsa-miR-3620 | 988 | UCACCCUGCAUCCCGCACCCAG | 989 | GUGGGCUGGGCUGGGCUGGGCC |
| hsa-miR-3621 | 990 | CGCGGGUCGGGGUCUGCAGG | 991 | UGCAGACCCCGACCCGCGUU |
| hsa-miR-3622a | 992 | UCACCUGACCUCCCAUGCCUGU | 993 | CAGGCACGGGAGCUCAGGUGAG |
| hsa-miR-3622b | 994 | UCACCUGAGCUCCCGUGCCUG | 995 | AGGCAUGGGAGGUCAGGUGA |
| hsa-miR-363 | 996 | AAUUGCACGGUAUCCAUCUGUA | 997 | CGGGUGGAUCACGAUGCAAUUU |
| hsa-miR-3646 | 998 | AAAAUGAAAUGAGCCCAGCCCA | 999 | GGCUGGGCUCAUUUCAUUUUUU |
| hsa-miR-3648 | 1000 | AGCCGCGGGGAUCGCCGAGGG | 1001 | CUCGGCGAUCCCCGCGGCUUU |
| hsa-miR-3649 | 1002 | AGGGACCUGAGUGUCUAAG | 1003 | UAGACACUCAGGUCCCUUU |
| hsa-miR-3650 | 1004 | AGGUGUGUCUGUAGAGUCC | 1005 | ACUCUACAGACACACCUUU |
| hsa-miR-3651 | 1006 | CAUAGCCCGGUCGCUGGUACAUGA | 1007 | AUGUACCAGCGACCGGGCUAUGUU |
| hsa-miR-3652 | 1008 | CGGCUGGAGGUGUGAGGA | 1009 | CUCACACCUCCAGCCGUU |
| hsa-miR-3653 | 1010 | CCUCCUGAUGAUUCUUCUUC | 1011 | CUAAGAAGUUGACUGAAG |
| hsa-miR-3654 | 1012 | GACUGGACAAGCUGAGGAA | 1013 | CCUCAGCUUGUCCAGUCUU |
| hsa-miR-3655 | 1014 | GCUUGUCGCUGCGGUGUUGCU | 1015 | CAACACCGCAGCGACAAGCUU |
| hsa-miR-3656 | 1016 | GGCGGGUGCGGGGGUGG | 1017 | ACCCCCGCACCCGCCUU |
| hsa-miR-3657 | 1018 | UGUGUCCCAUUAUUGGUGAUU | 1019 | UCACCAAUAAUGGGACACAUU |
| hsa-miR-3658 | 1020 | UUUAAGAAAACACCAUGGAGAU | 1021 | CUCCAUGGUGUUUUCUUAAAUU |
| hsa-miR-3659 | 1022 | UGAGUGUUGUCUACGAGGGCA | 1023 | CCCUCGUAGACAACACUCAUU |
| hsa-miR-365a | 1024 | UAAUGCCCCUAAAAAUCCUUAU | 1025 | AGGGACUUUUGGGGGCAGAUGUG |
| hsa-miR-365b | 1026 | UAAUGCCCCUAAAAAUCCUUAU | 1027 | AGGGACUUUCAGGGGCAGCUGU |
| hsa-miR-3660 | 1028 | ACUGACAGGAGAGCAUUUUGA | 1029 | AAAAUGCUCUCCUGUCAGUUU |
| hsa-miR-3661 | 1030 | UGACCUGGGACUCGGACAGCUG | 1031 | GCUGUCCGAGUCCCAGGUCAUU |
| hsa-miR-3662 | 1032 | GAAAAUGAUGAGUAGUGACUGAUG | 1033 | UCAGUCACUACUCAUCAUUUUCUU |
| hsa-miR-3663 | 1034 | UGAGCACCACACAGGCCGGGCGC | 1035 | GCUGGUCUGCGUGGUGCUCGG |
| hsa-miR-3664 | 1036 | UCUCAGGAGUAAAGACAGAGUU | 1037 | AACUCUGUCUUCACUCAUGAGU |
| hsa-miR-3665 | 1038 | AGCAGGUGCGGGGCGGCG | 1039 | CCGCCCCGCACCUGCUUU |
| hsa-miR-3666 | 1040 | CAGUGCAAGUGUAGAUGCCGA | 1041 | GGCAUCUACACUUGCACUGUU |
| hsa-miR-3667 | 1042 | ACCUUCCUCUCCAUGGGUCUUU | 1043 | AAAGACCCAUUGAGGAGAAGGU |
| hsa-miR-3668 | 1044 | AAUGUAGAGAUUGAUCAAAAU | 1045 | UUUGAUCAAUCUCUACAUUUU |
| hsa-miR-367 | 1046 | AAUUGCACUUUAGCAAUGGUGA | 1047 | ACUGUUGCUAAUAUGCAACUCU |
| hsa-miR-3670 | 1048 | AGAGCUCACAGCUGUCCUUCUCUA | 1049 | GAGAAGGACAGCUGUGAGCUCUUU |
| hsa-miR-3671 | 1050 | AUCAAAUAAGGACUAGUCUGCA | 1051 | CAGACUAGUCCUUAUUUGAUUU |
| hsa-miR-3672 | 1052 | AUGAGACUCAUGUAAAACAUCUU | 1053 | GAUGUUUUACAUGAGUCUCAUUU |
| hsa-miR-3674 | 1054 | AUUGUAGAACCUAAGAUUGGCC | 1055 | CCAAUCUUAGGUUCUACAAUUU |
| hsa-miR-3675 | 1056 | CAUCUCUAAGGAACUCCCCCAA | 1057 | UAUGGGGCUUCUGUAGAGAUUUC |
| hsa-miR-3677 | 1058 | CAGUGGCCAGAGCCCUGCAGUG | 1059 | CUCGUGGGCUCUGGCCACGGCC |

TABLE 1-continued miRNA Sequences

| miRNA | SEQ ID NO: | Sequence 1 | SEQ ID NO: | Sequence 2 |
|---|---|---|---|---|
| hsa-miR-3678 | 1060 | CUGCAGAGUUUGUACGGACCGG | 1061 | UCCGUACAAACUCUGCUGUG |
| hsa-miR-3679 | 1062 | CUUCCCCCAGUAAUCUUCAUC | 1063 | UGAGGAUAUGGCAGGGAAGGGGA |
| hsa-miR-3680 | 1064 | GACUCACUCACAGGAUUGUGCA | 1065 | UUUUGCAUGACCCUGGGAGUAGG |
| hsa-miR-3681 | 1066 | UAGUGGAUGAUGCACUCUGUGC | 1067 | ACACAGUGCUUCAUCCACUACU |
| hsa-miR-3682 | 1068 | CUACUUCUACCUGUGUUAUCAU | 1069 | UGAUGAUACAGGUGGAGGUAG |
| hsa-miR-3683 | 1070 | UGCGACAUUGGAAGUAGUAUCA | 1071 | AUACUACUUCCAAUGUCGCAUU |
| hsa-miR-3684 | 1072 | UUAGACCUAGUACACGUCCUU | 1073 | GGACGUGUACUAGGUCUAAUU |
| hsa-miR-3685 | 1074 | UUUCCUACCCUACCUGAAGACU | 1075 | UCUUCAGGUAGGGUAGGAAAUU |
| hsa-miR-3686 | 1076 | AUCUGUAAGAGAAAGUAAAUGA | 1077 | AUUUACUUUCUCUUACAGAUUU |
| hsa-miR-3687 | 1078 | CCCGGACAGGCGUUCGUGCGACGU | 1079 | GUCGCACGAACGCCUGUCCGGGUU |
| hsa-miR-3688 | 1080 | UAUGGAAAGACUUUGCCACUCU | 1081 | AGUGGCAAAGUCUUUCCAUAU |
| hsa-miR-3689a | 1082 | CUGGGAGGUGUGAUAUCGUGGU | 1083 | UGUGAUAUCAUGGUUCCUGGGA |
| hsa-miR-3689b | 1084 | CUGGGAGGUGUGAUAUUGUGGU | 1085 | UGUGAUAUCAUGGUUCCUGGGA |
| hsa-miR-3689c | 1086 | CUGGGAGGUGUGAUAUUGUGGU | 1087 | CACAAUAUCACACCUCCCAGUU |
| hsa-miR-3689d | 1088 | GGGAGGUGUGAUCUCACACUCG | 1089 | AGUGUGAGAUCACACCUCCCUU |
| hsa-miR-3689e | 1090 | UGUGAUAUCAUGGUUCCUGGGA | 1091 | CCAGGAACCAUGAUAUCACAUU |
| hsa-miR-3689f | 1092 | UGUGAUAUCGUGCUUCCUGGGA | 1093 | CCAGGAAGCACGAUAUCACAUU |
| hsa-miR-369 | 1094 | AAUAAUACAUGGUUGAUCUUU | 1095 | AGAUCGACCGUGUUAUAUUCGC |
| hsa-miR-3690 | 1096 | ACCUGGACCCAGCGUAGACAAAG | 1097 | UUGUCUACGCUGGGUCCAGGUUU |
| hsa-miR-3691 | 1098 | AGUGGAUGAUGGAGACUCGGUAC | 1099 | ACCAAGUCUGCGUCAUCCUCUC |
| hsa-miR-3692 | 1100 | GUUCCACACUGACACUGCAGAAGU | 1101 | CCUGCUGGUCAGGAGUGGAUACUG |
| hsa-miR-370 | 1102 | GCCUGCUGGGGUGGAACCUGGU | 1103 | CAGGUCACGUCUCUGCAGUUAC |
| hsa-miR-3713 | 1104 | GGUAUCCGUUUGGGGAUGGU | 1105 | CAUCCCCAAACGGAUACCUU |
| hsa-miR-3714 | 1106 | GAAGGCAGCAGUGCUCCCCUGU | 1107 | AGGGGAGCACUGCUGCCUUCUU |
| hsa-miR-371a | 1108 | ACUCAAACUGUGGGGGCACU | 1109 | AAGUGCCGCCAUCUUUUGAGUGU |
| hsa-miR-371b | 1110 | ACUCAAAAGAUGGCGGCACUUU | 1111 | AAGUGCCCCACAGUUUGAGUGC |
| hsa-miR-372 | 1112 | CCUCAAAUGUGGAGCACUAUUCU | 1113 | AAAGUGCUGCGACAUUUGAGCGU |
| hsa-miR-373 | 1114 | GAAGUGCUUCGAUUUUGGGGUGU | 1115 | ACUCAAAAUGGGGGCGCUUUCC |
| hsa-miR-374a | 1116 | UUAUAAUACAACCUGAUAAGUG | 1117 | CUUAUCAGAUUGUAUUGUAAUU |
| hsa-miR-374b | 1118 | CUUAGCAGGUUGUAUUAUCAUU | 1119 | AUAUAAUACAACCUGCUAAGUG |
| hsa-miR-374c | 1120 | CACUUAGCAGGUUGUAUUAUAU | 1121 | AUAAUACAACCUGCUAAGUGCU |
| hsa-miR-375 | 1122 | UUUGUUCGUUCGGCUCGCGUGA | 1123 | ACGCGAGCCGAACGAACAAAUU |
| hsa-miR-376a-1 | 1124 | AUCAUAGAGGAAAAUCCACGU | 1125 | GUAGAUUCUCCUUCUAUGAGUA |
| hsa-miR-376a-2 | 1126 | AUCAUAGAGGAAAAUCCACGU | 1127 | GGUAGAUUUCCUUCUAUGGU |
| hsa-miR-376b | 1128 | CGUGGAUAUUCCUUCUAUGUUU | 1129 | AUCAUAGAGGAAAAUCCAUGUU |
| hsa-miR-376c | 1130 | GGUGGAUAUUCCUUCUAUGUU | 1131 | AACAUAGAGGAAAUUCCACGU |
| hsa-miR-377 | 1132 | AGAGGUUGCCCUUGGUGAAUUC | 1133 | AUCACACAAAGGCAACUUUUGU |
| hsa-miR-378a | 1134 | CUCCUGACUCCAGGUCCUGUGU | 1135 | ACUGGACUUGGAGUCAGAAGGC |

TABLE 1-continued miRNA Sequences

| miRNA | SEQ ID NO: | Sequence 1 | SEQ ID NO: | Sequence 2 |
|---|---|---|---|---|
| hsa-miR-378b | 1136 | ACUGGACUUGGAGGCAGAA | 1137 | CUGCCUCCAAGUCCAGUUU |
| hsa-miR-378c | 1138 | ACUGGACUUGGAGUCAGAAGAGUGG | 1139 | ACUCUUCUGACUCCAAGUCCAGUUU |
| hsa-miR-378d | 1140 | ACUGGACUUGGAGUCAGAAA | 1141 | UCUGACUCCAAGUCCAGUUU |
| hsa-miR-378e | 1142 | ACUGGACUUGGAGUCAGGA | 1143 | CUGACUCCAAGUCCAGUUU |
| hsa-miR-378f | 1144 | ACUGGACUUGGAGCCAGAAG | 1145 | UCUGGCUCCAAGUCCAGUUU |
| hsa-miR-378g | 1146 | ACUGGGCUUGGAGUCAGAAG | 1147 | UCUGACUCCAAGCCCAGUUU |
| hsa-miR-378h | 1148 | ACUGGACUUGGUGUCAGAUGG | 1149 | AUCUGACACCAAGUCCAGUUU |
| hsa-miR-378i | 1150 | ACUGGACUAGGAGUCAGAAGG | 1151 | UUCUGACUCCUAGUCCAGUUU |
| hsa-miR-378j | 1152 | ACUGGAUUUGGAGCCAGAA | 1153 | CUGGCUCCAAAUCCAGUUU |
| hsa-miR-379 | 1154 | UGGUAGACUAUGGAACGUAGG | 1155 | UAUGUAACAUGGUCCACUAACU |
| hsa-miR-380 | 1156 | UGGUUGACCAUAGAACAUGCGC | 1157 | UAUGUAAUAUGGUCCACAUCUU |
| hsa-miR-381 | 1158 | AGCGAGGUUGCCCUUUGUAUAU | 1159 | UAUACAAGGGCAAGCUCUCUGU |
| hsa-miR-382 | 1160 | AAUCAUUCACGGACAACACUU | 1161 | GAAGUUGUUCGUGGUGGAUUCG |
| hsa-miR-383 | 1162 | ACAGCACUGCCUGGUCAGA | 1163 | AGAUCAGAAGGUGAUUGUGGCU |
| hsa-miR-384 | 1164 | AUUCCUAGAAAUUGUUCAUA | 1165 | UGAACAAUUUCUAGGAAUUU |
| hsa-miR-3907 | 1166 | AGGUGCUCCAGGCUGGCUCACA | 1167 | UGAGCCAGCCUGGAGCACCUUU |
| hsa-miR-3908 | 1168 | GAGCAAUGUAGGUAGACUGUUU | 1169 | ACAGUCUACCUACAUUGCUCUU |
| hsa-miR-3909 | 1170 | UGUCCUCUAGGGCCUGCAGUCU | 1171 | ACUGCAGGCCCUAGAGGACAUU |
| hsa-miR-3910 | 1172 | AAAGGCAUAAAACCAAGACA | 1173 | UCUUGGUUUUAUGCCUUUUU |
| hsa-miR-3911 | 1174 | UGUGUGGAUCCUGGAGGAGGCA | 1175 | CCUCCUCCAGGAUCCACACAUU |
| hsa-miR-3912 | 1176 | UAACGCAUAAUAUGGACAUGU | 1177 | AUGUCCAUAUUAUGGGUUAGU |
| hsa-miR-3913 | 1178 | UUUGGGACUGAUCUUGAUGUCU | 1179 | AGACAUCAAGAUCAGUCCCAAA |
| hsa-miR-3914 | 1180 | AAGGAACCAGAAAAUGAGAAGU | 1181 | UUCUCAUUUUCUGGUUCCUUUU |
| hsa-miR-3915 | 1182 | UUGAGGAAAAGAUGGUCUUAUU | 1183 | UAAGACCAUCUUUUCCUCAAUU |
| hsa-miR-3916 | 1184 | AAGAGGAAGAAAUGGCUGGUUCUCAG | 1185 | GAGAACCAGCCAUUUCUUCCUCUUUU |
| hsa-miR-3917 | 1186 | GCUCGGACUGAGCAGGUGGG | 1187 | CACCUGCUCAGUCCGAGCUU |
| hsa-miR-3918 | 1188 | ACAGGGCCGCAGAUGGAGACU | 1189 | UCUCCAUCUGCGGCCCUGUUU |
| hsa-miR-3919 | 1190 | GCAGAGAACAAAGGACUCAGU | 1191 | UGAGUCCUUUGUUCUCUGCUU |
| hsa-miR-3920 | 1192 | ACUGAUUAUCUUAACUCUCUGA | 1193 | AGAGAGUUAAGAUAAUCAGUUU |
| hsa-miR-3921 | 1194 | UCUCUGAGUACCAUAUGCCUUGU | 1195 | AAGGCAUAUGGUACUCAGAGAUU |
| hsa-miR-3922 | 1196 | UCUGGCCUUGACUUGACUCUUU | 1197 | UCAAGGCCAGAGGUCCCACAGCA |
| hsa-miR-3923 | 1198 | AACUAGUAAUGUUGGAUUAGGG | 1199 | CUAAUCCAACAUUACUAGUUUU |
| hsa-miR-3924 | 1200 | AUAUGUAUAUGUGACUGCUACU | 1201 | UAGCAGUCACAUAUACAUAUUU |
| hsa-miR-3925 | 1202 | AAGAGAACUGAAAGUGGAGCCU | 1203 | ACUCCAGUUUUAGUUCUCUUG |
| hsa-miR-3926 | 1204 | UGGCCAAAAAGCAGGCAGAGA | 1205 | UCUGCCUGCUUUUUGGCCAUU |
| hsa-miR-3927 | 1206 | CAGGUAGAUAUUUGAUAGGCAU | 1207 | GCCUAUCACAUAUCUGCCUGU |
| hsa-miR-3928 | 1208 | UGAAGCUCUAAGGUUCCGCCUGC | 1209 | GGAGGAACCUUGGAGCUUCGGC |

TABLE 1-continued miRNA Sequences

| miRNA | SEQ ID NO: | Sequence 1 | SEQ ID NO: | Sequence 2 |
|---|---|---|---|---|
| hsa-miR-3929 | 1210 | GAGGCUGAUGUGAGUAGACCACU | 1211 | UGGUCUACUCACAUCAGCCUCUU |
| hsa-miR-3934 | 1212 | UCAGGUGUGGAAACUGAGGCAG | 1213 | UGCUCAGGUUGCACAGCUGGGA |
| hsa-miR-3935 | 1214 | UGUAGAUACGAGCACCAGCCAC | 1215 | GGCUGGUGCUCGUAUCUACAUU |
| hsa-miR-3936 | 1216 | UAAGGGUGUAUGGCAGAUGCA | 1217 | CAUCUGCCAUACACCCCUUAUU |
| hsa-miR-3937 | 1218 | ACAGGCGGCUGUAGCAAUGGGGG | 1219 | CCCAUUGCUACAGCCGCCUGUUU |
| hsa-miR-3938 | 1220 | AAUUCCCUUGUAGAUAACCCGG | 1221 | GGGUUAUCUACAAGGGAAUUUU |
| hsa-miR-3939 | 1222 | UACGCGCAGACCACAGGAUGUC | 1223 | CAUCCUGUGGUCUGCGCGUAUU |
| hsa-miR-3940 | 1224 | GUGGGUUGGGCGGGCUCUG | 1225 | CAGCCCGGAUCCCAGCCCACUU |
| hsa-miR-3941 | 1226 | UUACACAACUGAGGAUCAUA | 1227 | UGAUCCCAGUUGUGUGUAAUU |
| hsa-miR-3942 | 1228 | AAGCAAUACUGUUACCUGAAAU | 1229 | UUUCAGAUAACAGUAUUACAU |
| hsa-miR-3943 | 1230 | UAGCCCCAGGCUUCACUUGGCG | 1231 | CCAAGUGAAGCCUGGGGCUAUU |
| hsa-miR-3944 | 1232 | UUCGGGCUGGCCUGCUGCUCCGG | 1233 | UGUGCAGCAGGCCAACCGAGA |
| hsa-miR-3945 | 1234 | AGGGCAUAGGAGAGGGUUGAUAU | 1235 | AUCAACCCUCUCCUAUGCCCUUU |
| hsa-miR-3960 | 1236 | GGCGGCGGCGGAGGCGGGGG | 1237 | CCCGCCUCCGCCGCCGCCUU |
| hsa-miR-3972 | 1238 | CUGCCAGCCCCGUUCCAGGGCA | 1239 | CCCUGGAACGGGGCUGGCAGUU |
| hsa-miR-3973 | 1240 | ACAAAGUACAGCAUUAGCCUUAG | 1241 | AAGGCUAAUGCUGUACUUUGUUU |
| hsa-miR-3974 | 1242 | AAAGGUCAUUGUAAGGUUAAUGC | 1243 | AUUAACCUUACAAUGACCUUUUU |
| hsa-miR-3975 | 1244 | UGAGGCUAAUGCACUACUUCAC | 1245 | GAAGUAGUGCAUUAGCCUCAUU |
| hsa-miR-3976 | 1246 | UAUAGAGAGCAGGAAGAUUAAUGU | 1247 | AUUAAUCUUCCUGCUCUCUAUAUU |
| hsa-miR-3977 | 1248 | GUGCUUCAUCGUAAUUAACCUUA | 1249 | AGGUUAAUUACGAUGAAGCACUU |
| hsa-miR-3978 | 1250 | GUGGAAAGCAUGCAUCCAGGGUGU | 1251 | ACCCUGGAUGCAUGCUUUCCACUU |
| hsa-miR-409 | 1252 | GAAUGUUGCUCGGUGAACCCCU | 1253 | AGGUUACCCGAGCAACUUUGCAU |
| hsa-miR-410 | 1254 | AGGUUGUCUGUGAUGAGUUCG | 1255 | AAUAUAACACAGAUGGCCUGU |
| hsa-miR-411 | 1256 | UAUGUAACACGGUCCACUAACC | 1257 | UAGUAGACCGUAUAGCGUACG |
| hsa-miR-412 | 1258 | UGGUCGACCAGUUGGAAAGUAAU | 1259 | ACUUCACCUGGUCCACUAGCCGU |
| hsa-miR-421 | 1260 | AUCAACAGACAUUAAUUGGGCGC | 1261 | GCCCAAUUAAUGUCUGUUGAUUU |
| hsa-miR-422a | 1262 | ACUGGACUUAGGGUCAGAAGGC | 1263 | CUUCUGACCCUAAGUCCAGUUU |
| hsa-miR-423 | 1264 | UGAGGGGCAGAGAGCGAGACUUU | 1265 | AGCUCGGUCUGAGGCCCCUCAGU |
| hsa-miR-424 | 1266 | CAGCAGCAAUUCAUGUUUUGAA | 1267 | CAAAACGUGAGGCGCUGCUAU |
| hsa-miR-425 | 1268 | AUCGGGAAUGUCGUGUCCGCCC | 1269 | AAUGACACGAUCACUCCCGUUGA |
| hsa-miR-4251 | 1270 | CCUGAGAAAGGGCCAA | 1271 | GGCCCUUUUCUCAGGUU |
| hsa-miR-4252 | 1272 | GGCCACUGAGUCAGCACCA | 1273 | GUGCUGACUCAGUGGCCUU |
| hsa-miR-4253 | 1274 | AGGGCAUGUCCAGGGGGU | 1275 | CCCCUGGACAUGCCCUUU |
| hsa-miR-4254 | 1276 | GCCUGGAGCUACUCCACCAUCUC | 1277 | GAUGGUGGAGUAGCUCCAGGCUU |
| hsa-miR-4255 | 1278 | CAGUGUUCAGAGAUGGA | 1279 | CAUCUCUGAACACUGUU |
| hsa-miR-4256 | 1280 | AUCUGACCUGAUGAAGGU | 1281 | CUUCAUCAGGUCAGAUUU |
| hsa-miR-4257 | 1282 | CCAGAGGUGGGGACUGAG | 1283 | CAGUCCCCACCUCUGGUU |
| hsa-miR-4258 | 1284 | CCCCGCCACCGCCUUGG | 1285 | AAGGCGGUGGCGGGGUU |

TABLE 1-continued miRNA Sequences

| miRNA | SEQ ID NO: | Sequence 1 | SEQ ID NO: | Sequence 2 |
|---|---|---|---|---|
| hsa-miR-4259 | 1286 | CAGUUGGGUCUAGGGGUCAGGA | 1287 | CUGACCCCUAGACCCAACUGUU |
| hsa-miR-4260 | 1288 | CUUGGGGCAUGGAGUCCCA | 1289 | GGACUCCAUGCCCCAAGUU |
| hsa-miR-4261 | 1290 | AGGAAACAGGGACCCA | 1291 | GGUCCCUGUUUCCUUU |
| hsa-miR-4262 | 1292 | GACAUUCAGACUACCUG | 1293 | GGUAGUCUGAAUGUCUU |
| hsa-miR-4263 | 1294 | AUUCUAAGUGCCUUGGCC | 1295 | CCAAGGCACUUAGAAUUU |
| hsa-miR-4264 | 1296 | ACUCAGUCAUGGUCAUU | 1297 | UGACCAUGACUGAGUUU |
| hsa-miR-4265 | 1298 | CUGUGGGCUCAGCUCUGGG | 1299 | CAGAGCUGAGCCCACAGUU |
| hsa-miR-4266 | 1300 | CUAGGAGGCCUUGGCC | 1301 | CCAAGGCCUCCUAGUU |
| hsa-miR-4267 | 1302 | UCCAGCUCGGUGGCAC | 1303 | GCCACCGAGCUGGAUU |
| hsa-miR-4268 | 1304 | GGCUCCUCCUCUCAGGAUGUG | 1305 | CAUCCUGAGAGGAGGAGCCUU |
| hsa-miR-4269 | 1306 | GCAGGCACAGACAGCCCUGGC | 1307 | CAGGGCUGUCUGUGCCUGCUU |
| hsa-miR-4270 | 1308 | UCAGGGAGUCAGGGGAGGGC | 1309 | CCUCCCCUGACUCCCUGAUU |
| hsa-miR-4271 | 1310 | GGGGGAAGAAAAGGUGGGG | 1311 | CCACCUUUUCUUCCCCCUU |
| hsa-miR-4272 | 1312 | CAUUCAACUAGUGAUUGU | 1313 | AAUCACUAGUUGAAUGUU |
| hsa-miR-4273 | 1314 | GUGUUCUCUGAUGGACAG | 1315 | GUCCAUCAGAGAACACUU |
| hsa-miR-4274 | 1316 | CAGCAGUCCCUCCCCCUG | 1317 | GGGGGAGGGACUGCUGUU |
| hsa-miR-4275 | 1318 | CCAAUUACCACUUCUUU | 1319 | AGAAGUGGUAAUUGGUU |
| hsa-miR-4276 | 1320 | CUCAGUGACUCAUGUGC | 1321 | ACAUGAGUCACUGAGUU |
| hsa-miR-4277 | 1322 | GCAGUUCUGAGCACAGUACAC | 1323 | GUACUGUGCUCAGAACUGCUU |
| hsa-miR-4278 | 1324 | CUAGGGGGUUUGCCCUUG | 1325 | AGGGCAAACCCCCUAGUU |
| hsa-miR-4279 | 1326 | CUCUCCUCCCGGCUUC | 1327 | AGCCGGGAGGAGAGUU |
| hsa-miR-4280 | 1328 | GAGUGUAGUUCUGAGCAGAGC | 1329 | UCUGCUCAGAACUACACUCUU |
| hsa-miR-4281 | 1330 | GGGUCCCGGGGAGGGGGG | 1331 | CCCCUCCCCGGGACCCUU |
| hsa-miR-4282 | 1332 | UAAAAUUUGCAUCCAGGA | 1333 | CUGGAUGCAAAUUUUAUU |
| hsa-miR-4283 | 1334 | UGGGGCUCAGCGAGUUU | 1335 | ACUCGCUGAGCCCCAUU |
| hsa-miR-4284 | 1336 | GGGCUCACAUCACCCCAU | 1337 | GGGGUGAUGUGAGCCCUU |
| hsa-miR-4285 | 1338 | GCGGCGAGUCCGACUCAU | 1339 | GAGUCGGACUCGCCGCUU |
| hsa-miR-4286 | 1340 | ACCCCACUCCUGGUACC | 1341 | UACCAGGAGUGGGGUUU |
| hsa-miR-4287 | 1342 | UCUCCCUUGAGGGCACUUU | 1343 | AGUGCCCUCAAGGGAGAUU |
| hsa-miR-4288 | 1344 | UUGUCUGCUGAGUUUCC | 1345 | AAACUCAGCAGACAAUU |
| hsa-miR-4289 | 1346 | GCAUUGUGCAGGGCUAUCA | 1347 | AUAGCCCUGCACAAUGCUU |
| hsa-miR-429 | 1348 | UAAUACUGUCUGGUAAAACCGU | 1349 | GGUUUUACCAGACAGUAUUAUU |
| hsa-miR-4290 | 1350 | UGCCCUCCUUUCUUCCCUC | 1351 | GGGAAGAAAGGAGGGCAUU |
| hsa-miR-4291 | 1352 | UUCAGCAGGAACAGCU | 1353 | CUGUUCCUGCUGAAUU |
| hsa-miR-4292 | 1354 | CCCCUGGGCCGGCCUUGG | 1355 | AAGGCCGGCCCAGGGGUU |
| hsa-miR-4293 | 1356 | CAGCCUGACAGGAACAG | 1357 | GUUCCUGUCAGGCUGUU |
| hsa-miR-4294 | 1358 | GGGAGUCUACAGCAGGG | 1359 | CUGCUGUAGACUCCCUU |

TABLE 1-continued miRNA Sequences

| miRNA | SEQ ID NO: | Sequence 1 | SEQ ID NO: | Sequence 2 |
|---|---|---|---|---|
| hsa-miR-4295 | 1360 | CAGUGCAAUGUUUUCCUU | 1361 | GGAAAACAUUGCACUGUU |
| hsa-miR-4296 | 1362 | AUGUGGGCUCAGGCUCA | 1363 | AGCCUGAGCCCACAUUU |
| hsa-miR-4297 | 1364 | UGCCUUCCUGUCUGUG | 1365 | CAGACAGGAAGGCAUU |
| hsa-miR-4298 | 1366 | CUGGGACAGGAGGAGGAGGCAG | 1367 | GCCUCCUCCUCCUGUCCCAGUU |
| hsa-miR-4299 | 1368 | GCUGGUGACAUGAGAGGC | 1369 | CUCUCAUGUCACCAGCUU |
| hsa-miR-4300 | 1370 | UGGGAGCUGGACUACUUC | 1371 | AGUAGUCCAGCUCCCAUU |
| hsa-miR-4301 | 1372 | UCCCACUACUUCACUUGUGA | 1373 | ACAAGUGAAGUAGUGGGAUU |
| hsa-miR-4302 | 1374 | CCAGUGUGGCUCAGCGAG | 1375 | CGCUGAGCCACACUGGUU |
| hsa-miR-4303 | 1376 | UUCUGAGCUGAGGACAG | 1377 | GUCCUCAGCUCAGAAUU |
| hsa-miR-4304 | 1378 | CCGGCAUGUCCAGGGCA | 1379 | CCCUGGACAUGCCGGUU |
| hsa-miR-4305 | 1380 | CCUAGACACCUCCAGUUC | 1381 | ACUGGAGGUGUCUAGGUU |
| hsa-miR-4306 | 1382 | UGGAGAGAAAGGCAGUA | 1383 | CUGCCUUUCUCUCCAUU |
| hsa-miR-4307 | 1384 | AAUGUUUUUUCCUGUUUCC | 1385 | AAACAGGAAAAAACAUUUU |
| hsa-miR-4308 | 1386 | UCCCUGGAGUUUCUUCUU | 1387 | GAAGAAACUCCAGGGAUU |
| hsa-miR-4309 | 1388 | CUGGAGUCUAGGAUUCCA | 1389 | GAAUCCUAGACUCCAGUU |
| hsa-miR-431 | 1390 | UGUCUUGCAGGCCGUCAUGCA | 1391 | CAGGUCGUCUUGCAGGGCUUCU |
| hsa-miR-4310 | 1392 | GCAGCAUUCAUGUCCC | 1393 | GACAUGAAUGCUGCUU |
| hsa-miR-4311 | 1394 | GAAAGAGAGCUGAGUGUG | 1395 | CACUCAGCUCUCUUUCUU |
| hsa-miR-4312 | 1396 | GGCCUUGUUCCUGUCCCA | 1397 | GGGACAGGAACAAGGCCUU |
| hsa-miR-4313 | 1398 | AGCCCCCUGGCCCCAAACCC | 1399 | GUUUGGGGCCAGGGGCUUU |
| hsa-miR-4314 | 1400 | CUCUGGGAAAUGGGACAG | 1401 | GUCCCAUUUCCCAGAGUU |
| hsa-miR-4315 | 1402 | CCGCUUUCUGAGCUGGAC | 1403 | CCAGCUCAGAAAGCGGUU |
| hsa-miR-4316 | 1404 | GGUGAGGCUAGCUGGUG | 1405 | CCAGCUAGCCUCACCUU |
| hsa-miR-4317 | 1406 | ACAUUGCCAGGGAGUUU | 1407 | ACUCCCUGGCAAUGUUU |
| hsa-miR-4318 | 1408 | CACUGUGGGUACAUGCU | 1409 | CAUGUACCCACAGUGUU |
| hsa-miR-4319 | 1410 | UCCCUGAGCAAAGCCAC | 1411 | GGCUUUGCUCAGGGAUU |
| hsa-miR-432 | 1412 | UCUUGGAGUAGGUCAUUGGGUGG | 1413 | CUGGAUGGCUCCUCCAUGUCU |
| hsa-miR-4320 | 1414 | GGGAUUCUGUAGCUUCCU | 1415 | GAAGCUACAGAAUCCCUU |
| hsa-miR-4321 | 1416 | UUAGCGGUGGACCGCCCUGCG | 1417 | CAGGGCGGUCCACCGCUAAUU |
| hsa-miR-4322 | 1418 | CUGUGGGCUCAGCGCUGUGGG | 1419 | CCACGCGCUGAGCCCACAGUU |
| hsa-miR-4323 | 1420 | CAGCCCCACAGCCUCAGA | 1421 | UGAGGCUGUGGGGCUGUU |
| hsa-miR-4324 | 1422 | CCCUGAGACCCUAACCUUAA | 1423 | AAGGUUAGGGUCUCAGGGUU |
| hsa-miR-4325 | 1424 | UUGCACUUGUCUCAGUGA | 1425 | ACUGAGACAAGUGCAAUU |
| hsa-miR-4326 | 1426 | UGUUCCUCUGUCUCCCAGAC | 1427 | CUGGGAGACAGAGGAACAUU |
| hsa-miR-4327 | 1428 | GGCUUGCAUGGGGACUGG | 1429 | AGUCCCCAUGCAAGCCUU |
| hsa-miR-4328 | 1430 | CCAGUUUCCCAGGAUU | 1431 | UCCUGGGAAACUGGUU |
| hsa-miR-4329 | 1432 | CCUGAGACCCUAGUUCCAC | 1433 | GGAACUAGGGUCUCAGGUU |
| hsa-miR-433 | 1434 | UACGGUGAGCCUGUCAUUAUUC | 1435 | AUCAUGAUGGGCUCCUCGGUGU |

TABLE 1-continued miRNA Sequences

| miRNA | SEQ ID NO: | Sequence 1 | SEQ ID NO: | Sequence 2 |
|---|---|---|---|---|
| hsa-miR-4330 | 1436 | CCUCAGAUCAGAGCCUUGC | 1437 | AAGGCUCUGAUCUGAGGUU |
| hsa-miR-4417 | 1438 | GGUGGGCUUCCCGGAGGG | 1439 | CUCCGGGAAGCCCACCUU |
| hsa-miR-4418 | 1440 | CACUGCAGGACUCAGCAG | 1441 | GCUGAGUCCUGCAGUGUU |
| hsa-miR-4419a | 1442 | UGAGGGAGGAGACUGCA | 1443 | CAGUCUCCUCCCUCAUU |
| hsa-miR-4419b | 1444 | GAGGCUGAAGGAAGAUGG | 1445 | AUCUUCCUUCAGCCUCUU |
| hsa-miR-4420 | 1446 | GUCACUGAUGUCUGUAGCUGAG | 1447 | CAGCUACAGACAUCAGUGACUU |
| hsa-miR-4421 | 1448 | ACCUGUCUGUGGAAAGGAGCUA | 1449 | GCUCCUUUCCACAGACAGGUUU |
| hsa-miR-4422 | 1450 | AAAAGCAUCAGGAAGUACCCA | 1451 | GGUACUUCCUGAUGCUUUUUU |
| hsa-miR-4423 | 1452 | AGUUGCCUUUUUGUUCCCAUGC | 1453 | AUAGGCACCAAAAAGCAACAA |
| hsa-miR-4424 | 1454 | AGAGUUAACUCAAAAUGGACUA | 1455 | GUCCAUUUUGAGUUAACUCUUU |
| hsa-miR-4425 | 1456 | UGUUGGAUUCAGCAGGACCAU | 1457 | GGUCCUGCUGAAUCCAACAUU |
| hsa-miR-4426 | 1458 | GAAGAUGGACGUACUUU | 1459 | AGUACGUCCAUCUUCUU |
| hsa-miR-4427 | 1460 | UCUGAAUAGAGUCUGAAGAGU | 1461 | UCUUCAGACUCUAUUCAGAUU |
| hsa-miR-4428 | 1462 | CAAGGAGACGGGAACAUGGAGC | 1463 | UCCAUGUUCCCGUCUCCUUGUU |
| hsa-miR-4429 | 1464 | AAAAGCUGGGCUGAGAGGCG | 1465 | CCUCUCAGCCCAGCUUUUUU |
| hsa-miR-4430 | 1466 | AGGCUGGAGUGAGCGGAG | 1467 | CCGCUCACUCCAGCCUUU |
| hsa-miR-4431 | 1468 | GCGACUCUGAAAACUAGAAGGU | 1469 | CUUCUAGUUUUCAGAGUCGCUU |
| hsa-miR-4432 | 1470 | AAAGACUCUGCAAGAUGCCU | 1471 | GCAUCUUGCAGAGUCUUUUU |
| hsa-miR-4433a | 1472 | ACAGGAGUGGGGGUGGGACAU | 1473 | CGUCCCACCCCCACUCCUGU |
| hsa-miR-4433b | 1474 | CAGGAGUGGGGGUGGGACGU | 1475 | AUGUCCCACCCCCACUCCUGU |
| hsa-miR-4434 | 1476 | AGGAGAAGUAAAGUAGAA | 1477 | CUACUUUACUUCUCCUUU |
| hsa-miR-4435 | 1478 | AUGGCCAGAGCUCACACAGAGG | 1479 | UCUGUGUGAGCUCUGGCCAUUU |
| hsa-miR-4436a | 1480 | GCAGGACAGGCAGAAGUGGAU | 1481 | CCACUUCUGCCUGUCCUGCUU |
| hsa-miR-4436b | 1482 | GUCCACUUCUGCCUGCCCUGCC | 1483 | CAGGGCAGGAAGAAGUGGACAA |
| hsa-miR-4437 | 1484 | UGGGCUCAGGGUACAAAGGUU | 1485 | CCUUUGUACCCUGAGCCCAUU |
| hsa-miR-4438 | 1486 | CACAGGCUUAGAAAAGACAGU | 1487 | UGUCUUUUCUAAGCCUGUGUU |
| hsa-miR-4439 | 1488 | GUGACUGAUACCUUGGAGGCAU | 1489 | GCCUCCAAGGUAUCAGUCACUU |
| hsa-miR-4440 | 1490 | UGUCGUGGGGCUUGCUGGCUUG | 1491 | AGCCAGCAAGCCCCACGACAUU |
| hsa-miR-4441 | 1492 | ACAGGGAGGAGAUUGUA | 1493 | CAAUCUCCUCCCUGUUU |
| hsa-miR-4442 | 1494 | GCCGGACAAGAGGGAGG | 1495 | UCCCUCUUGUCCGGCUU |
| hsa-miR-4443 | 1496 | UUGGAGGCGUGGGUUUU | 1497 | AACCCACGCCUCCAAUU |
| hsa-miR-4444 | 1498 | CUCGAGUUGGAAGAGGCG | 1499 | CCUCUUCCAACUCGAGUU |
| hsa-miR-4445 | 1500 | AGAUUGUUUCUUUUGCCGUGCA | 1501 | CACGGCAAAAGAAACAAUCCA |
| hsa-miR-4446 | 1502 | AUUUCCCUGCCAUUCCCUUGGC | 1503 | CAGGGCUGGCAGUGACAUGGGU |
| hsa-miR-4447 | 1504 | GGUGGGGGCUGUUGUUU | 1505 | ACAACAGCCCCCACCUU |
| hsa-miR-4448 | 1506 | GGCUCCUUGGUCUAGGGGUA | 1507 | CCCCUAGACCAAGGAGCCUU |
| hsa-miR-4449 | 1508 | CGUCCCGGGCUGCGCGAGGCA | 1509 | CCUCGCGCAGCCCGGGACGUU |

TABLE 1-continued miRNA Sequences

| miRNA | SEQ ID NO: | Sequence 1 | SEQ ID NO: | Sequence 2 |
| --- | --- | --- | --- | --- |
| hsa-miR-4450 | 1510 | UGGGGAUUUGGAGAAGUGGUGA | 1511 | ACCACUUCUCCAAAUCCCCAUU |
| hsa-miR-4451 | 1512 | UGGUAGAGCUGAGGACA | 1513 | UCCUCAGCUCUACCAUU |
| hsa-miR-4452 | 1514 | UUGAAUUCUUGGCCUUAAGUGAU | 1515 | CACUUAAGGCCAAGAAUUCAAUU |
| hsa-miR-4453 | 1516 | GAGCUUGGUCUGUAGCGGUU | 1517 | CCGCUACAGACCAAGCUCUU |
| hsa-miR-4454 | 1518 | GGAUCCGAGUCACGGCACCA | 1519 | GUGCCGUGACUCGGAUCCUU |
| hsa-miR-4455 | 1520 | AGGGUGUGUGUGUUUUU | 1521 | AAACACACACACCCUUU |
| hsa-miR-4456 | 1522 | CCUGGUGGCUUCCUUUU | 1523 | AAGGAAGCCACCAGGUU |
| hsa-miR-4457 | 1524 | UCACAAGGUAUUGACUGGCGUA | 1525 | CGCCAGUCAAUACCUUGUGAUU |
| hsa-miR-4458 | 1526 | AGAGGUAGGUGUGGAAGAA | 1527 | CUUCCACACCUACCUCUUU |
| hsa-miR-4459 | 1528 | CCAGGAGGCGGAGGAGGUGGAG | 1529 | CCACCUCCUCCGCCUCCUGGUU |
| hsa-miR-4460 | 1530 | AUAGUGGUUGUGAAUUUACCUU | 1531 | GGUAAAUUCACAACCACUAUUU |
| hsa-miR-4461 | 1532 | GAUUGAGACUAGUAGGGCUAGGC | 1533 | CUAGCCCUACUAGUCUCAAUCUU |
| hsa-miR-4462 | 1534 | UGACACGGAGGGUGGCUUGGGAA | 1535 | CCCAAGCCACCCUCCGUGUCAUU |
| hsa-miR-4463 | 1536 | GAGACUGGGGUGGGGCC | 1537 | CCCCACCCCAGUCUCUU |
| hsa-miR-4464 | 1538 | AAGGUUUGGAUAGAUGCAAUA | 1539 | UUGCAUCUAUCCAAACCUUUU |
| hsa-miR-4465 | 1540 | CUCAAGUAGUCUGACCAGGGGA | 1541 | CCCUGGUCAGACUACUUGAGUU |
| hsa-miR-4466 | 1542 | GGGUGCGGGCCGGCGGGG | 1543 | CCGCCGGCCCGCACCCUU |
| hsa-miR-4467 | 1544 | UGGCGGCGGUAGUUAUGGGCUU | 1545 | GCCCAUAACUACCGCCGCCAUU |
| hsa-miR-4468 | 1546 | AGAGCAGAAGGAUGAGAU | 1547 | CUCAUCCUUCUGCUCUUU |
| hsa-miR-4469 | 1548 | GCUCCCUCUAGGGUCGCUCGGA | 1549 | CGAGCGACCCUAGAGGGAGCUU |
| hsa-miR-4470 | 1550 | UGGCAAACGUGGAAGCCGAGA | 1551 | UCGGCUUCCACGUUUGCCAUU |
| hsa-miR-4471 | 1552 | UGGGAACUUAGUAGAGGUUUAA | 1553 | AAACCUCUACUAAGUUCCCAUU |
| hsa-miR-4472 | 1554 | GGUGGGGGGUGUUGUUUU | 1555 | AACAACACCCCCCACCUU |
| hsa-miR-4473 | 1556 | CUAGUGCUCUCCGUUACAAGUA | 1557 | CUUGUAACGGAGAGCACUAGUU |
| hsa-miR-4474 | 1558 | UUGUGGCUGGUCAUGAGGCUAA | 1559 | UUAGUCUCAUGAUCAGACACA |
| hsa-miR-4475 | 1560 | CAAGGGACCAAGCAUUCAUUAU | 1561 | AAUGAAUGCUUGGUCCCUUGUU |
| hsa-miR-4476 | 1562 | CAGGAAGGAUUUAGGGACAGGC | 1563 | CUGUCCCUAAAUCCUUCCUGUU |
| hsa-miR-4477a | 1564 | CUAUUAAGGACAUUUGUGAUUC | 1565 | AUCACAAAUGUCCUUAAUAGUU |
| hsa-miR-4477b | 1566 | AUUAAGGACAUUUGUGAUUGAU | 1567 | CAAUCACAAAUGUCCUUAAUUU |
| hsa-miR-4478 | 1568 | GAGGCUGAGCUGAGGAG | 1569 | CCUCAGCUCAGCCUCUU |
| hsa-miR-4479 | 1570 | CGCGCGGCCGUGCUCGGAGCAG | 1571 | GCUCCGAGCACGGCCGCGCGUU |
| hsa-miR-448 | 1572 | UUGCAUAUGUAGGAUGUCCCAU | 1573 | GGGACAUCCUACAUAUGCAAUU |
| hsa-miR-4480 | 1574 | AGCCAAGUGGAAGUUACUUUA | 1575 | AAGUAACUUCCACUUGGCUUU |
| hsa-miR-4481 | 1576 | GGAGUGGGCUGGUGGUU | 1577 | CCACCAGCCCACUCCUU |
| hsa-miR-4482 | 1578 | UUUCUAUUUCUCAGUGGGGCUC | 1579 | AACCCAGUGGGCUAUGGAAAUG |
| hsa-miR-4483 | 1580 | GGGGUGGUCUGUUGUUG | 1581 | ACAACAGACCACCCCUU |
| hsa-miR-4484 | 1582 | AAAAGGCGGGAGAAGCCCCA | 1583 | GGGCUUCUCCCGCCUUUUUU |
| hsa-miR-4485 | 1584 | UAACGGCCGCGGUACCCUAA | 1585 | ACCGCCUGCCCAGUGA |

TABLE 1-continued miRNA Sequences

| miRNA | SEQ ID NO: | Sequence 1 | SEQ ID NO: | Sequence 2 |
|---|---|---|---|---|
| hsa-miR-4486 | 1586 | GCUGGGCGAGGCUGGCA | 1587 | CCAGCCUCGCCCAGCUU |
| hsa-miR-4487 | 1588 | AGAGCUGGCUGAAGGGCAG | 1589 | GCCCUUCAGCCAGCUCUUU |
| hsa-miR-4488 | 1590 | AGGGGGCGGGCUCCGGCG | 1591 | CCGGAGCCCGCCCCCUUU |
| hsa-miR-4489 | 1592 | UGGGGCUAGUGAUGCAGGACG | 1593 | UCCUGCAUCACUAGCCCCAUU |
| hsa-miR-4490 | 1594 | UCUGGUAAGAGAUUUGGGCAUA | 1595 | UGCCCAAAUCUCUUACCAGAUU |
| hsa-miR-4491 | 1596 | AAUGUGGACUGGUGUGACCAAA | 1597 | UGGUCACACCAGUCCACAUUUU |
| hsa-miR-4492 | 1598 | GGGGCUGGGCGCGCGCC | 1599 | CGCGCGCCCAGCCCCUU |
| hsa-miR-4493 | 1600 | AGAAGGCCUUUCCAUCUCUGU | 1601 | AGAGAUGGAAAGGCCUUCUUU |
| hsa-miR-4494 | 1602 | CCAGACUGUGGCUGACCAGAGG | 1603 | UCUGGUCAGCCACAGUCUGGUU |
| hsa-miR-4495 | 1604 | AAUGUAAACAGGCUUUUUGCU | 1605 | CAAAAAGCCUGUUUACAUUUU |
| hsa-miR-4496 | 1606 | GAGGAAACUGAAGCUGAGAGGG | 1607 | CUCUCAGCUUCAGUUUCCUCUU |
| hsa-miR-4497 | 1608 | CUCCGGGACGGCUGGGC | 1609 | CCAGCCGUCCCGGAGUU |
| hsa-miR-4498 | 1610 | UGGGCUGGCAGGGCAAGUGCUG | 1611 | GCACUUGCCCUGCCAGCCCAUU |
| hsa-miR-4499 | 1612 | AAGACUGAGAGGAGGGA | 1613 | CCUCCUCUCAGUCUUUU |
| hsa-miR-449a | 1614 | UGGCAGUGUAUUGUUAGCUGGU | 1615 | CAGCUAACAAUACACUGCCAUU |
| hsa-miR-449b | 1616 | CAGCCACAACUACCCUGCCACU | 1617 | AGGCAGUGUAUUGUUAGCUGGC |
| hsa-miR-449c | 1618 | UAGGCAGUGUAUUGCUAGCGGCUGU | 1619 | UUGCUAGUUGCACUCCUCUCUGU |
| hsa-miR-4500 | 1620 | UGAGGUAGUAGUUUCUU | 1621 | GAAACUACUACCUCAUU |
| hsa-miR-4501 | 1622 | UAUGUGACCUCGGAUGAAUCA | 1623 | AUUCAUCCGAGGUCACAUAUU |
| hsa-miR-4502 | 1624 | GCUGAUGAUGAUGGUGCUGAAG | 1625 | UCAGCACCAUCAUCAUCAGCUU |
| hsa-miR-4503 | 1626 | UUUAAGCAGGAAAUAGAAUUUA | 1627 | AAUUCUAUUUCCUGCUUAAAUU |
| hsa-miR-4504 | 1628 | UGUGACAAUAGAGAUGAACAUG | 1629 | UGUUCAUCUCUAUUGUCACAUU |
| hsa-miR-4505 | 1630 | AGGCUGGGCUGGGACGGA | 1631 | CGUCCCAGCCCAGCCUUU |
| hsa-miR-4506 | 1632 | AAAUGGUGGUCUGAGGCAA | 1633 | GCCUCAGACCACCCAUUUUU |
| hsa-miR-4507 | 1634 | CUGGGUUGGGCUGGGCUGGG | 1635 | CAGCCCAGCCCAACCCAGUU |
| hsa-miR-4508 | 1636 | GCGGGGCUGGGCGCGCG | 1637 | CGCGCCCAGCCCCGCUU |
| hsa-miR-4509 | 1638 | ACUAAAGGAUAUAGAAGGUUUU | 1639 | AACCUUCUAUAUCCUUUAGUUU |
| hsa-miR-450a-1 | 1640 | UUUUGCGAUGUGUUCCUAAUAU | 1641 | AUUGGGAACAUUUUGCAUGUAU |
| hsa-miR-450a-2 | 1642 | UUUUGCGAUGUGUUCCUAAUAU | 1643 | AUUGGGGACAUUUUGCAUUCAU |
| hsa-miR-450b | 1644 | UUUUGCAAUAUGUUCCUGAAUA | 1645 | UUGGGAUCAUUUUGCAUCCAUA |
| hsa-miR-4510 | 1646 | UGAGGGAGUAGGAUGUAUGGUU | 1647 | CCAUACAUCCUACUCCCUCAUU |
| hsa-miR-4511 | 1648 | GAAGAACUGUUGCAUUUGCCCU | 1649 | GGCAAAUGCAACAGUUCUUCUU |
| hsa-miR-4512 | 1650 | CAGGGCCUCACUGUAUCGCCCA | 1651 | GGCGAUACAGUGAGGCCCUGUU |
| hsa-miR-4513 | 1652 | AGACUGACGGCUGGAGGCCCAU | 1653 | GGGCCUCCAGCCGUCAGUCUUU |
| hsa-miR-4514 | 1654 | ACAGGCAGGAUUGGGGAA | 1655 | CCCCAAUCCUGCCUGUUU |
| hsa-miR-4515 | 1656 | AGGACUGGACUCCCGGCAGCCC | 1657 | GCUGCCGGGAGUCCAGUCCUUU |
| hsa-miR-4516 | 1658 | GGGAGAAGGGUCGGGGC | 1659 | CCCGACCCUUCUCCCUU |

TABLE 1-continued miRNA Sequences

| miRNA | SEQ ID NO: | Sequence 1 | SEQ ID NO: | Sequence 2 |
| --- | --- | --- | --- | --- |
| hsa-miR-4517 | 1660 | AAAUAUGAUGAAACUCACAGCUGAG | 1661 | CAGCUGUGAGUUUCAUCAUAUUUUU |
| hsa-miR-4518 | 1662 | GCUCAGGGAUGAUAACUGUGCUGAGA | 1663 | UCAGCACAGUUAUCAUCCCUGAGCUU |
| hsa-miR-4519 | 1664 | CAGCAGUGCGCAGGGCUG | 1665 | GCCCUGCGCACUGCUGUU |
| hsa-miR-451a | 1666 | AAACCGUUACCAUUACUGAGUU | 1667 | CUCAGUAAUGGUAACGGUUUUU |
| hsa-miR-451b | 1668 | UAGCAAGAGAACCAUUACCAUU | 1669 | UGGUAAUGGUUCUCUUGCUAUU |
| hsa-miR-452 | 1670 | AACUGUUUGCAGAGGAAACUGA | 1671 | CUCAUCUGCAAAGAAGUAAGUG |
| hsa-miR-4520-1 | 1672 | CCUGCGUGUUUUCUGUCCAA | 1673 | UUGGACAGAAAACACGCAGGAA |
| hsa-miR-4520-2 | 1674 | CCUGCGUGUUUUCUGUCCAA | 1675 | UUUGGACAGAAAACACGCAGGU |
| hsa-miR-4521 | 1676 | GCUAAGGAAGUCCUGUGCUCAG | 1677 | GAGCACAGGACUUCCUUAGCUU |
| hsa-miR-4522 | 1678 | UGACUCUGCCUGUAGGCCGGU | 1679 | CGGCCUACAGGCAGAGUCAUU |
| hsa-miR-4523 | 1680 | GACCGAGAGGGCCUCGGCUGU | 1681 | AGCCGAGGCCCUCUCGGUCUU |
| hsa-miR-4524a | 1682 | AUAGCAGCAUGAACCUGUCUCA | 1683 | UGAGACAGGCUUAUGCUGCUAU |
| hsa-miR-4524b | 1684 | AUAGCAGCAUAAGCCUGUCUC | 1685 | GAGACAGGUUCAUGCUGCUA |
| hsa-miR-4525 | 1686 | GGGGGGAUGUGCAUGCUGGUU | 1687 | CCAGCAUGCACAUCCCCCUU |
| hsa-miR-4526 | 1688 | GCUGACAGCAGGGCUGGCCGCU | 1689 | CGGCCAGCCCUGCUGUCAGCUU |
| hsa-miR-4527 | 1690 | UGGUCUGCAAAGAGAUGACUGU | 1691 | AGUCAUCUCUUUGCAGACCAUU |
| hsa-miR-4528 | 1692 | UCAUUAUAUGUAUGAUCUGGAC | 1693 | CCAGAUCAUACAUAUAAUGAUU |
| hsa-miR-4529 | 1694 | AGGCCAUCAGCAGUCCAAUGAA | 1695 | AUUGGACUGCUGAUGGCCCGU |
| hsa-miR-4530 | 1696 | CCCAGCAGGACGGGAGCG | 1697 | CUCCCGUCCUGCUGGGUU |
| hsa-miR-4531 | 1698 | AUGGAGAAGGCUUCUGA | 1699 | AGAAGCCUUCUCCAUUU |
| hsa-miR-4532 | 1700 | CCCCGGGGAGCCCGGCG | 1701 | CCGGGCUCCCCGGGGUU |
| hsa-miR-4533 | 1702 | UGGAAGGAGGUUGCCGGACGCU | 1703 | CGUCCGGCAACCUCCUUCCAUU |
| hsa-miR-4534 | 1704 | GGAUGGAGGAGGGGUCU | 1705 | ACCCCUCCUCCAUCCUU |
| hsa-miR-4535 | 1706 | GUGGACCUGGCUGGGAC | 1707 | CCCAGCCAGGUCCACUU |
| hsa-miR-4536 | 1708 | UCGUGCAUAUAUCUACCACAU | 1709 | UGUGGUAGAUAUAUGCACGAU |
| hsa-miR-4537 | 1710 | UGAGCCGAGCUGAGCUUAGCUG | 1711 | GCUAAGCUCAGCUCGGCUCAUU |
| hsa-miR-4538 | 1712 | GAGCUUGGAUGAGCUGGGCUGA | 1713 | AGCCCAGCUCAUCCAAGCUCUU |
| hsa-miR-4539 | 1714 | GCUGAACUGGGCUGAGCUGGGC | 1715 | CCAGCUCAGCCCAGUUCAGCUU |
| hsa-miR-454 | 1716 | ACCCUAUCAAUAUUGUCUCUGC | 1717 | UAGUGCAAUAUUGCUUAUAGGGU |
| hsa-miR-4540 | 1718 | UUAGUCCUGCCUGUAGGUUUA | 1719 | AACCUACAGGCAGGACUAAUU |
| hsa-miR-455 | 1720 | GCAGUCCAUGGGCAUAUACAC | 1721 | UAUGUGCCUUUGGACUACAUCG |
| hsa-miR-4632 | 1722 | UGCCGCCCUCUCGCUGCUCUAG | 1723 | GAGGGCAGCGUGGGUGUGGCGGA |
| hsa-miR-4633 | 1724 | AUAUGCCUGGCUAGCUCCUC | 1725 | AGGAGCUAGCCAGGCAUAUGCA |
| hsa-miR-4634 | 1726 | CGGCGCGACCGGCCCGGGG | 1727 | CCGGGCCGGUCGCGCCGUU |
| hsa-miR-4635 | 1728 | UCUUGAAGUCAGAACCCGCAA | 1729 | GCGGGUUCUGACUUCAAGAUU |
| hsa-miR-4636 | 1730 | AACUCGUGUUCAAAGCCUUUAG | 1731 | AAAGGCUUUGAACACGAGUUUU |
| hsa-miR-4637 | 1732 | UACUAACUGCAGAUUCAAGUGA | 1733 | ACUUGAAUCUGCAGUUAGUAUU |
| hsa-miR-4638 | 1734 | CCUGGACACCGCUCAGCCGGCCG | 1735 | ACUCGGCUGCGGUGGACAAGU |

TABLE 1-continued miRNA Sequences

| miRNA | SEQ ID NO: | Sequence 1 | SEQ ID NO: | Sequence 2 |
|---|---|---|---|---|
| hsa-miR-4639 | 1736 | UCACUCUCACCUUGCUUUGC | 1737 | UUGCUAAGUAGGCUGAGAUUGA |
| hsa-miR-4640 | 1738 | UGGGCCAGGGAGCAGCUGGUGGG | 1739 | CACCCCCUGUUUCCUGGCCCAC |
| hsa-miR-4641 | 1740 | UGCCCAUGCCAUACUUUUGCCUCA | 1741 | AGGCAAAAGUAUGGCAUGGGCAUU |
| hsa-miR-4642 | 1742 | AUGGCAUCGUCCCCUGGUGGCU | 1743 | CCACCAGGGGACGAUGCCAUUU |
| hsa-miR-4643 | 1744 | GACACAUGACCAUAAAUGCUAA | 1745 | AGCAUUUAUGGUCAUGUGUCUU |
| hsa-miR-4644 | 1746 | UGGAGAGAGAAAAGAGACAGAAG | 1747 | UCUGUCUCUUUUCUCUCUCCAUU |
| hsa-miR-4645 | 1748 | ACCAGGCAAGAAAUAUUGU | 1749 | AGACAGUAGUUCUUGCCUGGUU |
| hsa-miR-4646 | 1750 | AUUGUCCCUCUCCCUUCCCAG | 1751 | ACUGGGAAGAGGAGCUGAGGGA |
| hsa-miR-4647 | 1752 | GAAGAUGGUGCUGUGCUGAGGAA | 1753 | CCUCAGCACAGCACCAUCUUCUU |
| hsa-miR-4648 | 1754 | UGUGGGACUGCAAAUGGGAG | 1755 | CCCAUUUGCAGUCCCACAUU |
| hsa-miR-4649 | 1756 | UGGGCGAGGGGUGGGCUCUCAGAG | 1757 | UCUGAGGCCUGCCUCUCCCCA |
| hsa-miR-4650 | 1758 | AGGUAGAAUGAGGCCUGACAU | 1759 | UCAGGCCUCUUUCUACCUU |
| hsa-miR-4651 | 1760 | CGGGGUGGGUGAGGUCGGGC | 1761 | CCGACCUCACCCACCCCGUU |
| hsa-miR-4652 | 1762 | AGGGGACUGGUUAAUAGAACUA | 1763 | GUUCUGUUAACCCAUCCCCUCA |
| hsa-miR-4653 | 1764 | UCUCUGAGCAAGGCUUAACACC | 1765 | UGGAGUUAAGGGUUGCUUGGAGA |
| hsa-miR-4654 | 1766 | UGUGGGAUCUGGAGGCAUCUGG | 1767 | AGAUGCCUCCAGAUCCCACAUU |
| hsa-miR-4655 | 1768 | ACCCUCGUCAGGUCCCCGGGG | 1769 | CACCGGGGAUGGCAGAGGGUCG |
| hsa-miR-4656 | 1770 | UGGGCUGAGGGCAGGAGGCCUGU | 1771 | AGGCCUCCUGCCCUCAGCCCAUU |
| hsa-miR-4657 | 1772 | AAUGUGGAAGUGGUCUGAGGCAU | 1773 | GCCUCAGACCACUUCCACAUUUU |
| hsa-miR-4658 | 1774 | GUGAGUGUGGAUCCUGGAGGAAU | 1775 | UCCUCCAGGAUCCACACUCACUU |
| hsa-miR-4659a | 1776 | UUUCUUCUUAGACAUGGCAACG | 1777 | CUGCCAUGUCUAAGAAGAAAAC |
| hsa-miR-4659b | 1778 | UUUCUUCUUAGACAUGGCAGCU | 1779 | UUGCCAUGUCUAAGAAGAA |
| hsa-miR-466 | 1780 | AUACACAUACACGCAACACAUU | 1781 | GUGUGUUGCGUGUAUGUGUAUUU |
| hsa-miR-4660 | 1782 | UGCAGCUCUGGUGGAAAAUGGAG | 1783 | CCAUUUUCCACCAGAGCUGCAUU |
| hsa-miR-4661 | 1784 | AACUAGCUCUGUGGAUCCUGAC | 1785 | CAGGAUCCACAGAGCUAGUCCA |
| hsa-miR-4662a | 1786 | UUAGCCAAUUGUCCAUCUUUAG | 1787 | AAAGAUAGACAAUUGGCUAAAU |
| hsa-miR-4662b | 1788 | AAAGAUGGACAAUUGGCUAAAU | 1789 | UUAGCCAAUUGUCCAUCUUUUU |
| hsa-miR-4663 | 1790 | AGCUGAGCUCCAUGGACGUGCAGU | 1791 | UGCACGUCCAUGGAGCUCAGCUUU |
| hsa-miR-4664 | 1792 | CUUCCGGUCUGUGAGCCCCGUC | 1793 | UGGGGUGCCCACUCCGCAAGUU |
| hsa-miR-4665 | 1794 | CUCGGCCGCGGCGCGUAGCCCCCGCC | 1795 | CUGGGGGACGCGUGAGCGCGAGC |
| hsa-miR-4666a | 1796 | AUACAUGUCAGAUUGUAUGCC | 1797 | CAUACAAUCUGACAUGUAUUU |
| hsa-miR-4666b | 1798 | UUGCAUGUCAGAUUGUAAUUCCC | 1799 | GAAUUACAAUCUGACAUGCAAUU |
| hsa-miR-4667 | 1800 | ACUGGGGAGCAGAAGGAGAACC | 1801 | UCCCUCCUUCUGUCCCCACAG |
| hsa-miR-4668 | 1802 | AGGGAAAAAAAAAGGAUUUGUC | 1803 | GAAAAUCCUUUUUGUUUUUCCAG |
| hsa-miR-4669 | 1804 | UGUGUCCGGGAAGUGGAGGAGG | 1805 | UCCUCCACUUCCCGGACACAUU |
| hsa-miR-4670 | 1806 | AAGCGACCAUGAUGUAACUUCA | 1807 | UGAAGUUACAUCAUGGUCGCUU |
| hsa-miR-4671 | 1808 | ACCGAAGACUGUGCGCUAAUCU | 1809 | UUAGUGCAUAGUCUUUGGUCU |

TABLE 1-continued miRNA Sequences

| miRNA | SEQ ID NO: | Sequence 1 | SEQ ID NO: | Sequence 2 |
|---|---|---|---|---|
| hsa-miR-4672 | 1810 | UUACACAGCUGGACAGAGGCA | 1811 | CCUCUGUCCAGCUGUGUAAUU |
| hsa-miR-4673 | 1812 | UCCAGGCAGGAGCCGGACUGGA | 1813 | CAGUCCGGCUCCUGCCUGGAUU |
| hsa-miR-4674 | 1814 | CUGGGCUCGGGACGCGCGGCU | 1815 | CCGCGCGUCCCGAGCCCAGUU |
| hsa-miR-4675 | 1816 | GGGGCUGUGAUUGACCAGCAGG | 1817 | UGCUGGUCAAUCACAGCCCCUU |
| hsa-miR-4676 | 1818 | GAGCCAGUGGUGAGACAGUGA | 1819 | CACUGUUUCACCACUGGCUCUU |
| hsa-miR-4677 | 1820 | UUGUUCUUUGGUCUUUCAGCCA | 1821 | UCUGUGAGACCAAAGAACUACU |
| hsa-miR-4678 | 1822 | AAGGUAUUGUUCAGACUUAUGA | 1823 | AUAAGUCUGAACAAUACCUUUU |
| hsa-miR-4679 | 1824 | UCUGUGAUAGAGAUUCUUUGCU | 1825 | CAAAGAAUCUCUAUCACAGAUU |
| hsa-miR-4680 | 1826 | UCUGAAUUGUAAGAGUUGUUA | 1827 | AGAACUCUUGCAGUCUUAGAUGU |
| hsa-miR-4681 | 1828 | AACGGGAAUGCAGGCUGUAUCU | 1829 | AUACAGCCUGCAUUCCCGUUUU |
| hsa-miR-4682 | 1830 | UCUGAGUUCCUGGAGCCUGGUCU | 1831 | ACCAGGCUCCAGGAACUCAGAUU |
| hsa-miR-4683 | 1832 | UGGAGAUCCAGUGCUCGCCCGAU | 1833 | CGGGCGAGCACUGGAUCUCCAUU |
| hsa-miR-4684 | 1834 | CUCUCUACUGACUUGCAACAUA | 1835 | UGUUGCAAGUCGGUGGAGACGU |
| hsa-miR-4685 | 1836 | CCCAGGGCUUGGAGUGGGGCAAGGUU | 1837 | UCUCCCUUCCUGCCCUGGCUAG |
| hsa-miR-4686 | 1838 | UAUCUGCUGGGCUUUCUGGUGUU | 1839 | CACCAGAAAGCCCAGCAGAUAUU |
| hsa-miR-4687 | 1840 | UGGCUGUUGGAGGGGCAGGC | 1841 | CAGCCCUCCUCCCGCACCCAAA |
| hsa-miR-4688 | 1842 | UAGGGGCAGCAGAGGACCUGGG | 1843 | CAGGUCCUCUGCUGCCCCUAUU |
| hsa-miR-4689 | 1844 | UUGAGGAGACAUGGUGGGGGCC | 1845 | CCCCCACCAUGUCUCCCAAUU |
| hsa-miR-4690 | 1846 | GCAGCCCAGCUGAGGCCUCUG | 1847 | GAGCAGGCGAGGCUGGGCUGAA |
| hsa-miR-4691 | 1848 | GUCCUCCAGGCCAUGAGCUGCGG | 1849 | CCAGCCACGACUGAGAGUGCAU |
| hsa-miR-4692 | 1850 | UCAGGCAGUGUGGGUAUCAGAU | 1851 | CUGAUACCCACACUGCCUGAUU |
| hsa-miR-4693 | 1852 | AUACUGUGAAUUUCACUGUCACA | 1853 | UGAGAGUGGAAUUCACAGUAUUU |
| hsa-miR-4694 | 1854 | AGGUGUUAUCCUAUCCAUUUGC | 1855 | CAAAUGGACAGGAUAACACCU |
| hsa-miR-4695 | 1856 | CAGGAGGCAGUGGGCGAGCAGG | 1857 | UGAUCUCACCGCUGCCUCCUUC |
| hsa-miR-4696 | 1858 | UGCAAGACGGAUACUGUCAUCU | 1859 | AUGACAGUAUCCGUCUUGCAUU |
| hsa-miR-4697 | 1860 | AGGGGGCGCAGUCACUGACGUG | 1861 | UGUCAGUGACUCCUGCCCCUUGGU |
| hsa-miR-4698 | 1862 | UCAAAAUGUAGAGGAAGACCCCA | 1863 | GGGUCUUCCUCUACAUUUUGAUU |
| hsa-miR-4699 | 1864 | AAUUUACUCUGCAAUCUUCUCCC | 1865 | AGAAGAUUGCAGAGUAAGUUCC |
| hsa-miR-4700 | 1866 | CACAGGACUGACUCCUCACCCCAGUG | 1867 | UCUGGGGAUGAGGACAGUGUGU |
| hsa-miR-4701 | 1868 | UUGGCCACCACACCUACCCCUU | 1869 | AUGGGUGAUGGGUGUGGUGU |
| hsa-miR-4703 | 1870 | UGUAGUUGUAUUGUAUUGCCAC | 1871 | UAGCAAUACAGUACAAAUAUAGU |
| hsa-miR-4704 | 1872 | UCAGUCACAUAUCUAGUGUCUA | 1873 | GACACUAGGCAUGUGAGUGAUU |
| hsa-miR-4705 | 1874 | UCAAUCACUUGGUAAUUGCUGU | 1875 | AGCAAUUACCAAGUGAUUGAUU |
| hsa-miR-4706 | 1876 | AGCGGGGAGGAAGUGGGCGCUGCUU | 1877 | GCAGCGCCCACUUCCUCCCCGCUUU |
| hsa-miR-4707 | 1878 | AGCCCGCCCCAGCCGAGGUUCU | 1879 | GCCCCGGCGCGGGCGGGUUCGG |
| hsa-miR-4708 | 1880 | AGAGAUGCCGCCUUGCUCCUU | 1881 | AGCAAGGCGGCAUCUCUGAU |
| hsa-miR-4709 | 1882 | ACAACAGUGACUUGCUCUCCAA | 1883 | UUGAAGAGGAGGUGCUCUGUAGC |
| hsa-miR-4710 | 1884 | GGGUGAGGGCAGGUGGUU | 1885 | CCACCUGCCCUCACCCUU |

TABLE 1-continued miRNA Sequences

| miRNA | SEQ ID NO: | Sequence 1 | SEQ ID NO: | Sequence 2 |
|---|---|---|---|---|
| hsa-miR-4711 | 1886 | CGUGUCUUCUGGCUUGAU | 1887 | UGCAUCAGGCCAGAAGACAUGAG |
| hsa-miR-4712 | 1888 | AAUGAGAGACCUGUACUGUAU | 1889 | UCCAGUACAGGUCUCUCAUUUC |
| hsa-miR-4713 | 1890 | UUCUCCCACUACCAGGCUCCCA | 1891 | UGGGAUCCAGACAGUGGGAGAA |
| hsa-miR-4714 | 1892 | AACUCUGACCCCUUAGGUUGAU | 1893 | CCAACCUAGGUGGUCAGAGUUG |
| hsa-miR-4715 | 1894 | GUGCCACCUUAACUGCAGCCAAU | 1895 | AAGUUGGCUGCAGUUAAGGUGG |
| hsa-miR-4716 | 1896 | AAGGGGAAGGAAACAUGGAGA | 1897 | UCCAUGUUUCCUUCCCCCUUCU |
| hsa-miR-4717 | 1898 | ACACAUGGGUGGCUGUGGCCU | 1899 | UAGGCCACAGCCACCCAUGUGU |
| hsa-miR-4718 | 1900 | AGCUGUACCUGAAACCAAGCA | 1901 | CUUGGUUUCAGGUACAGCUUU |
| hsa-miR-4719 | 1902 | UCACAAAUCUAUAAUAUGCAGG | 1903 | UGCAUAUUAUAGAUUUGUGAUU |
| hsa-miR-4720 | 1904 | UGCUUAAGUUGUACCAAGUAU | 1905 | CCUGGCAUAUUUGGUAUAACUU |
| hsa-miR-4721 | 1906 | UGAGGGCUCCAGGUGACGGUGG | 1907 | ACCGUCACCUGGAGCCCUCAUU |
| hsa-miR-4722 | 1908 | GGCAGGAGGGCUGUGCCAGGUUG | 1909 | ACCUGCCAGCACCUCCCUGCAG |
| hsa-miR-4723 | 1910 | UGGGGGAGCCAUGAGAUAAGAGCA | 1911 | CCCUCUCUGGCUCCUCCCCAAA |
| hsa-miR-4724 | 1912 | AACUGAACCAGGAGUGAGCUUCG | 1913 | GUACCUUCUGGUUCAGCUAGU |
| hsa-miR-4725 | 1914 | AGACCCUGCAGCCUUCCCACC | 1915 | UGGGGAAGGCGUCAGUGUCGGG |
| hsa-miR-4726 | 1916 | ACCCAGGUUCCCUCUGGCCGCA | 1917 | AGGGCCAGAGGAGCCUGGAGUGG |
| hsa-miR-4727 | 1918 | AUAGUGGGAAGCUGGCAGAUUC | 1919 | AUCUGCCAGCUUCCACAGUGG |
| hsa-miR-4728 | 1920 | CAUGCUGACCUCCUCCUGCCCCAG | 1921 | UGGGAGGGGAGAGGCAGCAAGCA |
| hsa-miR-4729 | 1922 | UCAUUUAUCUGUUGGGAAGCUA | 1923 | GCUUCCCAACAGAUAAAUGAUU |
| hsa-miR-4730 | 1924 | CUGGCGGAGCCCAUUCCAUGCCA | 1925 | GCAUGGAAUGGGCUCCGCCAGUU |
| hsa-miR-4731 | 1926 | UGCUGGGGGCCACAUGAGUGUG | 1927 | CACACAAGUGGCCCCCAACACU |
| hsa-miR-4732 | 1928 | UGUAGAGCAGGGAGCAGGAAGCU | 1929 | GCCCUGACCUGUCCUGUUCUG |
| hsa-miR-4733 | 1930 | AAUCCCAAUGCUAGACCCGGUG | 1931 | CCACCAGGUCUAGCAUUGGGAU |
| hsa-miR-4734 | 1932 | GCUGCGGGCUGCGGUCAGGGCG | 1933 | CCCUGACCGCAGCCCGCAGCUU |
| hsa-miR-4735 | 1934 | CCUAAUUUGAACACCUUCGGUA | 1935 | AAAGGUGCUCAAAUUAGACAU |
| hsa-miR-4736 | 1936 | AGGCAGGUUAUCUGGGCUG | 1937 | GCCCAGAUAACCUGCCUUU |
| hsa-miR-4737 | 1938 | AUGCGAGGAUGCUGACAGUG | 1939 | CUGUCAGCAUCCUCGCAUUU |
| hsa-miR-4738 | 1940 | UGAAACUGGAGCGCCUGGAGGA | 1941 | ACCAGCGCGUUUUCAGUUUCAU |
| hsa-miR-4739 | 1942 | AAGGGAGGAGGAGCGGAGGGGCCCU | 1943 | GGCCCCUCCGCUCCUCCUCCCUUUU |
| hsa-miR-4740 | 1944 | GCCCGAGAGGAUCCGUCCCUGC | 1945 | AGGACUGAUCCUCUCGGGCAGG |
| hsa-miR-4741 | 1946 | CGGGCUGUCCGGAGGGUCGGCU | 1947 | CCGACCCCUCCGGACAGCCCGUU |
| hsa-miR-4742 | 1948 | UCAGGCAAAGGGAUAUUUACAGA | 1949 | UCUGUAUUCUCCUUUGCCUGCAG |
| hsa-miR-4743 | 1950 | UUUCUGUCUUUUCUGGUCCAG | 1951 | UGGCCGGAUGGGACAGGAGGCAU |
| hsa-miR-4744 | 1952 | UCUAAAGACUAGACUUCGCUAUG | 1953 | UAGCGAAGUCUAGUCUUUAGAUU |
| hsa-miR-4745 | 1954 | UGAGUGGGGCUCCCGGGACGGCG | 1955 | UGGCCCGGCGACGUCUCACGGUC |
| hsa-miR-4746 | 1956 | AGCGGUGCUCCUGCGGGCCGA | 1957 | CCGGUCCCAGGAGAACCUGCAGA |
| hsa-miR-4747 | 1958 | AAGGCCCGGGCUUUCCUCCCAG | 1959 | AGGGAAGGAGGCUUGGUCUUAG |

TABLE 1-continued miRNA Sequences

| miRNA | SEQ ID NO: | Sequence 1 | SEQ ID NO: | Sequence 2 |
| --- | --- | --- | --- | --- |
| hsa-miR-4748 | 1960 | GAGGUUUGGGGAGGAUUUGCU | 1961 | CAAAUCCUCCCCAAACCUCUU |
| hsa-miR-4749 | 1962 | UGCGGGACAGGCCAGGGCAUC | 1963 | CGCCCCUCCUGCCCCCACAG |
| hsa-miR-4750 | 1964 | CCUGACCCACCCCUCCCGCAG | 1965 | CUCGGGCGGAGGUGGUUGAGUG |
| hsa-miR-4751 | 1966 | AGAGGACCCGUAGCUGCUAGAAGG | 1967 | UUCUAGCAGCUACGGGUCCUCUUU |
| hsa-miR-4752 | 1968 | UUGUGGAUCUCAAGGAUGUGCU | 1969 | CACAUCCUUGAGAUCCACAAUU |
| hsa-miR-4753 | 1970 | CAAGGCCAAAGGAAGAGAACAG | 1971 | UUCUCUUUCUUUAGCCUUGUGU |
| hsa-miR-4754 | 1972 | AUGCGGACCUGGGUUAGCGGAGU | 1973 | UCCGCUAACCCAGGUCCGCAUUU |
| hsa-miR-4755 | 1974 | UUUCCCUUCAGAGCCUGGCUUU | 1975 | AGCCAGGCUCUGAAGGGAAAGU |
| hsa-miR-4756 | 1976 | CCAGAGAUGGUUGCCUUCCUAU | 1977 | CAGGGAGGCGCUCACUCUCUGCU |
| hsa-miR-4757 | 1978 | CAUGACGUCACAGAGGCUUCGC | 1979 | AGGCCUCUGUGACGUCACGGUGU |
| hsa-miR-4758 | 1980 | GUGAGUGGGAGCCGGUGGGGCUG | 1981 | UGCCCCACCUGCUGACCACCCUC |
| hsa-miR-4759 | 1982 | UAGGACUAGAUGUUGGAAUUA | 1983 | AUUCCAACAUCUAGUCCUAUU |
| hsa-miR-4760 | 1984 | AAAUUCAUGUUCAAUCUAAACC | 1985 | UUUAGAUUGAACAUGAAGUUAG |
| hsa-miR-4761 | 1986 | ACAAGGUGUGCAUGCCUGACC | 1987 | GAGGGCAUGCGCACUUUGUCC |
| hsa-miR-4762 | 1988 | CCAAAUCUUGAUCAGAAGCCU | 1989 | CUUCUGAUCAAGAUUUGUGGUG |
| hsa-miR-4763 | 1990 | AGGCAGGGGCUGGUGCUGGGCGGG | 1991 | CGCCUGCCCAGCCCUCCUGCU |
| hsa-miR-4764 | 1992 | UUAACUCCUUUCACACCCAUGG | 1993 | UGGAUGUGGAAGGAGUUAUCU |
| hsa-miR-4765 | 1994 | UGAGUGAUUGAUAGCUAUGUUC | 1995 | ACAUAGCUAUCAAUCACUCAUU |
| hsa-miR-4766 | 1996 | UCUGAAAGAGCAGUUGGUGUU | 1997 | AUAGCAAUUGCUCUUUUGGAA |
| hsa-miR-4767 | 1998 | CGCGGGCGCUCCUGGCCGCCGCC | 1999 | CGGCGGCCAGGAGCGCCCGCGUU |
| hsa-miR-4768 | 2000 | CCAGGAGAUCCAGAGAGAAU | 2001 | AUUCUCUCUGGAUCCCAUGGAU |
| hsa-miR-4769 | 2002 | UCUGCCAUCCUCCCUCCCCUAC | 2003 | GGUGGGAUGGAGAGAAGGUAUGAG |
| hsa-miR-4770 | 2004 | UGAGAUGACACUGUAGCU | 2005 | CUACAGUGUCAUCUCAUU |
| hsa-miR-4771 | 2006 | AGCAGACUUGACCUACAAUUA | 2007 | AUUGUAGGUCAAGUCUGCUUU |
| hsa-miR-4772 | 2008 | CCUGCAACUUUGCCUGAUCAGA | 2009 | UGAUCAGGCAAAAUUGCAGACU |
| hsa-miR-4773 | 2010 | CAGAACAGGAGCAUAGAAAGGC | 2011 | CUUUCUAUGCUCCUGUUCUGUU |
| hsa-miR-4774 | 2012 | AUUGCCUAACAUGUGCCAGAA | 2013 | UCUGGUAUGUAGUAGGUAAUAA |
| hsa-miR-4775 | 2014 | UUAAUUUUUUGUUUCGGUCACU | 2015 | UGACCGAAACAAAAAAUUAAUU |
| hsa-miR-4776 | 2016 | GUGGACCAGGAUGGCAAGGGCU | 2017 | CUUGCCAUCCUGGUCCACUGCAU |
| hsa-miR-4777 | 2018 | UUCUAGAUGAGAGAUAUAUAUA | 2019 | AUACCUCAUCUAGAAUGCUGUA |
| hsa-miR-4778 | 2020 | UCUUCUUCCUUUGCAGAGUUGA | 2021 | AAUUCUGUAAAGGAAGAAGAGG |
| hsa-miR-4779 | 2022 | UAGGAGGGAAUAGUAAAAGCAG | 2023 | GCUUUUACUAUUCCCUCCUAUU |
| hsa-miR-4780 | 2024 | ACCCUUGAGCCUGAUCCCUAGC | 2025 | UAGGGAUCAGGCUCAAGGGUUU |
| hsa-miR-4781 | 2026 | UAGCGGGGAUUCCAAUAUUGG | 2027 | AAUGUUGGAAUCCUCGCUAGAG |
| hsa-miR-4782 | 2028 | UGAUUGUCUUCAUAUCUAGAAC | 2029 | UUCUGGAUAUGAAGACAAUCAA |
| hsa-miR-4783 | 2030 | CCCCGGUGUUUGGGGCGCGUCUGC | 2031 | GGCGCGCCCAGCUCCCGGGCU |
| hsa-miR-4784 | 2032 | UGAGGAGAUGCUGGGACUGA | 2033 | AGUCCCAGCAUCUCCUCAUU |
| hsa-miR-4785 | 2034 | AGAGUCGGCGACGCCGCCAGC | 2035 | UGGCGGCGUCGCCGACUCUUU |

TABLE 1-continued miRNA Sequences

| miRNA | SEQ ID NO: | Sequence 1 | SEQ ID NO: | Sequence 2 |
|---|---|---|---|---|
| hsa-miR-4786 | 2036 | UGAAGCCAGCUCUGGUCUGGGC | 2037 | UGAGACCAGGACUGGAUGCACC |
| hsa-miR-4787 | 2038 | GAUGCGCCGCCCACUGCCCCGCGC | 2039 | GCGGGGGUGGCGGCGGCAUCCC |
| hsa-miR-4788 | 2040 | UUACGGACCAGCUAAGGGAGGC | 2041 | CUCCCUUAGCUGGUCCGUAAUU |
| hsa-miR-4789 | 2042 | GUAUACACCUGAUAUGUGUAUG | 2043 | CACACAUAGCAGGUGUAUAUA |
| hsa-miR-4790 | 2044 | AUCGCUUUACCAUUCAUGUU | 2045 | UGAAUGGUAAAGCGAUGUCACA |
| hsa-miR-4791 | 2046 | UGGAUAUGAUGACUGAAA | 2047 | UCAGUCAUCAUAUCCAUU |
| hsa-miR-4792 | 2048 | CGGUGAGCGCUCGCUGGC | 2049 | CAGCGAGCGCUCACCGUU |
| hsa-miR-4793 | 2050 | ACAUCCUGCUCCACAGGGCAGAGG | 2051 | UCUGCACUGUGAGUUGGCUGGCU |
| hsa-miR-4794 | 2052 | UCUGGCUAUCUCACGAGACUGU | 2053 | AGUCUCGUGAGAUAGCCAGAUU |
| hsa-miR-4795 | 2054 | AGAAGUGGCUAAUAAUAUUGA | 2055 | AUAUUAUUAGCCACUUCUGGAU |
| hsa-miR-4796 | 2056 | UAAAGUGGCAGAGUAUAGACAC | 2057 | UGUCUAUACUCUGUCACUUUAC |
| hsa-miR-4797 | 2058 | GACAGAGUGCCACUUACUGAA | 2059 | UCUCAGUAAGUGGCACUCUGU |
| hsa-miR-4798 | 2060 | UUCGGUAUACUUUGUGAAUUGG | 2061 | AACUCACGAAGUAUACCGAAGU |
| hsa-miR-4799 | 2062 | AUCUAAAUGCAGCAUGCCAGUC | 2063 | ACUGGCAUGCUGCAUUUAUAUA |
| hsa-miR-4800 | 2064 | CAUCCGUCCGUCUGUCCAC | 2065 | AGUGGACCGAGGAAGGAAGGA |
| hsa-miR-4801 | 2066 | UACACAAGAAAACCAAGGCUCA | 2067 | AGCCUUGGUUUUCUUGUGUAUU |
| hsa-miR-4802 | 2068 | UAUGGAGGUUCUAGACCAUGUU | 2069 | UACAUGGAUGGAAACCUUCAAGC |
| hsa-miR-4803 | 2070 | UAACAUAAUAGUGUGGAUUGA | 2071 | AAUCCACACUAUUAUGUUAUU |
| hsa-miR-4804 | 2072 | UGCUUAACCUUGCCCUCGAAA | 2073 | UUGGACGGUAAGGUUAAGCAA |
| hsa-miR-483 | 2074 | UCACUCCUCUCCUCCCGUCUU | 2075 | AAGACGGGAGGAAAGAAGGGAG |
| hsa-miR-484 | 2076 | UCAGGCUCAGUCCCCUCCCGAU | 2077 | CGGGAGGGGACUGAGCCUGAUU |
| hsa-miR-485 | 2078 | AGAGGCUGGCCGUGAUGAAUUC | 2079 | GUCAUACACGGCUCUCCUCUCU |
| hsa-miR-486 | 2080 | CGGGGCAGCUCAGUACAGGAU | 2081 | UCCUGUACUGAGCUGCCCCGAG |
| hsa-miR-487a | 2082 | GUGGUUAUCCCUGCUGUGUUCG | 2083 | AAUCAUACAGGGACAUCCAGUU |
| hsa-miR-487b | 2084 | GUGGUUAUCCCUGUCCUGUUCG | 2085 | AAUCGUACAGGGUCAUCCACUU |
| hsa-miR-488 | 2086 | UUGAAAGGCUAUUUCUUGGUC | 2087 | CCCAGAUAAUGGCACUCUCAA |
| hsa-miR-489 | 2088 | GUGACAUCACAUAUACGGCAGC | 2089 | GGUCGUAUGUGUGACGCCAUUU |
| hsa-miR-490 | 2090 | CCAUGGAUCUCCAGGUGGGU | 2091 | CAACCUGGAGGACUCCAUGCUG |
| hsa-miR-491 | 2092 | AGUGGGGAACCCUUCCAUGAGG | 2093 | CUUAUGCAAGAUUCCCUUCUAC |
| hsa-miR-492 | 2094 | AGGACCUGCGGGACAAGAUUCUU | 2095 | GAAUCUUGUCCCGCAGGUCCUUU |
| hsa-miR-493 | 2096 | UGAAGGUCUACUGUGUGCCAGG | 2097 | UUGUACAUGGUAGGCUUUCAUU |
| hsa-miR-494 | 2098 | AGGUUGUCCGUGUUGUCUUCUCU | 2099 | UGAAACAUACACGGGAAACCUC |
| hsa-miR-495 | 2100 | GAAGUUGCCCAUGUUAUUUUCG | 2101 | AAACAAACAUGGUGCACUUCUU |
| hsa-miR-496 | 2102 | UGAGUAUUACAUGGCCAAUCUC | 2103 | GAUUGGCCAUGUAAUACUCAUU |
| hsa-miR-497 | 2104 | CAGCAGCACACUGUGGUUUGU | 2105 | CAAACCACACUGUGGUGUUAGA |
| hsa-miR-498 | 2106 | UUUCAAGCCAGGGGGCGUUUUUC | 2107 | AAAACGCCCCUGGCUUGAAAUU |
| hsa-miR-4999 | 2108 | UGCUGUAUUGUCAGGUAGUGA | 2109 | UCACUACCUGACAAUACAGU |

TABLE 1-continued miRNA Sequences

| miRNA | SEQ ID NO: | Sequence 1 | SEQ ID NO: | Sequence 2 |
|---|---|---|---|---|
| hsa-miR-499a | 2110 | UUAAGACUUGCAGUGAUGUUU | 2111 | AACAUCACAGCAAGUCUGUGCU |
| hsa-miR-499b | 2112 | ACAGACUUGCUGUGAUGUUCA | 2113 | AACAUCACUGCAAGUCUUAACA |
| hsa-miR-5000 | 2114 | UCAGGACACUUCUGAACUUGGA | 2115 | CAGUUCAGAAGUGUUCCUGAGU |
| hsa-miR-5001 | 2116 | AGGGCUGGACUCAGCGGCGGAGCU | 2117 | UUCUGCCUCUGUCCAGGUCCUU |
| hsa-miR-5002 | 2118 | UGACUGCCUCACUGACCACUU | 2119 | AAUUUGGUUUCUGAGGCACUUAGU |
| hsa-miR-5003 | 2120 | UCACAACAACCUUGCAGGGUAGA | 2121 | UACUUUUCUAGGUUGUUGGGG |
| hsa-miR-5004 | 2122 | CUUGGAUUUUCCUGGGCCUCAG | 2123 | UGAGGACAGGGCAAAUUCACGA |
| hsa-miR-5006 | 2124 | UUGCCAGGGCAGGAGGUGGAA | 2125 | UUUCCCUUUCCAUCCUGGCAG |
| hsa-miR-5007 | 2126 | UAGAGUCUGGCUGAUAUGGUUU | 2127 | AUCAUAUGAACCAAACUCUAAU |
| hsa-miR-5008 | 2128 | UGAGGCCCUUGGGGCACAGUGG | 2129 | CCUGUGCUCCCAGGGCCUCGC |
| hsa-miR-5009 | 2130 | UCCUAAAUCUGAAAGUCCAAAA | 2131 | UUGGACUUUUCAGAUUUGGGGAU |
| hsa-miR-500a | 2132 | AUGCACCUGGGCAAGGAUUCUG | 2133 | UAAUCCUUGCUACCUGGGUGAGA |
| hsa-miR-500b | 2134 | AAUCCUUGCUACCUGGGU | 2135 | GCACCCAGGCAAGGAUUCUG |
| hsa-miR-501 | 2136 | AAUGCACCCGGGCAAGGAUUCU | 2137 | AAUCCUUUGUCCCUGGGUGAGA |
| hsa-miR-5010 | 2138 | AGGGGGAUGGCAGAGCAAAAUU | 2139 | UUUUGUGUCUCCCAUUCCCCAG |
| hsa-miR-5011 | 2140 | UAUAUAUACAGCCAUGCACUC | 2141 | GUGCAUGGCUGUAUAUAUAACA |
| hsa-miR-502 | 2142 | AAUGCACCUGGGCAAGGAUUCA | 2143 | AUCCUUGCUAUCUGGGUGCUA |
| hsa-miR-503 | 2144 | UAGCAGCGGGAACAGUUCUGCAG | 2145 | GGGGUAUUGUUUCCGCUGCCAGG |
| hsa-miR-504 | 2146 | GGGAGUGCAGGGCAGGGUUUC | 2147 | AGACCCUGGUCUGCACUCUAUC |
| hsa-miR-5047 | 2148 | UUGCAGCUGCGGUUGUAAGGU | 2149 | CUUACAACCGCAGCUGCAAUU |
| hsa-miR-505 | 2150 | CGUCAACACUUGCUGGUUUCCU | 2151 | GGGAGCCAGGAAGUAUUGAUGU |
| hsa-miR-506 | 2152 | UAAGGCACCCUUCUGAGUAGA | 2153 | UAUUCAGGAAGGUGUUACUUAA |
| hsa-miR-507 | 2154 | UUUUGCACCUUUUGGAGUGAA | 2155 | CACUCCAAAAGGUGCAAAAUU |
| hsa-miR-508 | 2156 | UGAUUGUAGCCUUUUGGAGUAGA | 2157 | UACUCCAGAGGGCGUCACUCAUG |
| hsa-miR-5087 | 2158 | GGGUUUGUAGCUUUGCUGGCAUG | 2159 | UGCCAGCAAAGCUACAAACCCUU |
| hsa-miR-5088 | 2160 | UCCCUUCUUCCUGGGCCCUCA | 2161 | CAGGGCUCAGGGAUUGGAUGGAGG |
| hsa-miR-5089 | 2162 | GUGGGAUUUCUGAGUAGCAUC | 2163 | AUGCUACUCGGAAAUCCCACUGA |
| hsa-miR-509-1 | 2164 | UGAUUGGUACGUCUGUGGGUAG | 2165 | UACUGCAGACAGUGGCAAUCA |
| hsa-miR-509-3 | 2166 | UGAUUGGUACGUCUGUGGGUAG | 2167 | UACUGCAGACGUGGCAAUCAUG |
| hsa-miR-5090 | 2168 | CCGGGGCAGAUUGGUGUAGGGUG | 2169 | CCCUACACCAAUCUGCCCCGGUU |
| hsa-miR-5091 | 2170 | ACGGAGACGACAAGACUGUGCUG | 2171 | GCACAGUCUUGUCGUCUCCGUUU |
| hsa-miR-5092 | 2172 | AAUCCACGCUGAGCUUGGCAUC | 2173 | UGCCAAGCUCAGCGUGGAUUUU |
| hsa-miR-5093 | 2174 | AGGAAAUGAGGCUGGCUAGGAGC | 2175 | UCCUAGCCAGCCUCAUUUCCUUU |
| hsa-miR-5094 | 2176 | AAUCAGUGAAUGCCUUGAACCU | 2177 | GUUCAAGGCAUUCACUGAUUUU |
| hsa-miR-5095 | 2178 | UUACAGGCGUGAACCACCGCG | 2179 | CGGUGGUUCACGCCUGUAAUU |
| hsa-miR-5096 | 2180 | GUUUCACCAUGUUGGUCAGGC | 2181 | CUGACCAACAUGGUGAAACUU |
| hsa-miR-510 | 2182 | UACUCAGGAGAGUGGCAAUCAC | 2183 | AUUGAAACCUCUAAGAGUGGA |
| hsa-miR-5100 | 2184 | UUCAGAUCCCAGCGGUGCCUCU | 2185 | AGGCACCGCUGGGAUCUGAAUU |

TABLE 1-continued miRNA Sequences

| miRNA | SEQ ID NO: | Sequence 1 | SEQ ID NO: | Sequence 2 |
|---|---|---|---|---|
| hsa-miR-511 | 2186 | GUGUCUUUUGCUCUGCAGUCA | 2187 | AAUGUGUAGCAAAAGACAGA |
| hsa-miR-512 | 2188 | AAGUGCUGUCAUAGCUGAGGUC | 2189 | CACUCAGCCUUGAGGGCACUUUC |
| hsa-miR-513a | 2190 | UAAAUUUCACCUUUCUGAGAAGG | 2191 | UUCACAGGGAGGUGUCAU |
| hsa-miR-513b | 2192 | AAAUGUCACCUUUUUGAGAGGA | 2193 | UUCACAAGGAGGUGUCAUUUAU |
| hsa-miR-513c | 2194 | UUCUCAAGGAGGUGUCGUUUAU | 2195 | UAAAUUUCACCUUUCUGAGAAGA |
| hsa-miR-514a | 2196 | AUUGACACUUCUGUGAGUAGA | 2197 | UACUCUGGAGAGUGACAAUCAUG |
| hsa-miR-514b | 2198 | AUUGACACCUCUGUGAGUGGA | 2199 | UUCUCAAGAGGGAGGCAAUCAU |
| hsa-miR-515 | 2200 | GAGUGCCUUCUUUUGGAGCGUU | 2201 | UUCUCCAAAAGAAAGCACUUUCUG |
| hsa-miR-516a | 2202 | UUCUCGAGGAAAGAAGCACUUUC | 2203 | UGCUUCCUUUCAGAGGGU |
| hsa-miR-516b | 2204 | AUCUGGAGGUAAGAAGCACUUU | 2205 | UGCUUCCUUUCAGAGGGU |
| hsa-miR-517a | 2206 | AUCGUGCAUCCCUUUUAGAGUGU | 2207 | CCUCUAGAUGGAAGCACUGUCU |
| hsa-miR-517b | 2208 | AUCGUGCAUCCCUUUAGAGUGU | 2209 | CCUCUAGAUGGAAGCACUGUCU |
| hsa-miR-517c | 2210 | AUCGUGCAUCCUUUUAGAGUGU | 2211 | CCUCUAGAUGGAAGCACUGUCU |
| hsa-miR-5186 | 2212 | AGAGAUUGGUAGAAAUCAGGU | 2213 | CUGAUUUCUACCAAUCUCUUU |
| hsa-miR-5187 | 2214 | ACUGAAUCCUCUUUUCCUCAG | 2215 | UGGGAUGAGGGAUUGAAGUGGA |
| hsa-miR-5188 | 2216 | AAUCGGACCCAUUUAAACCGGAG | 2217 | CCGGUUUAAAUGGGUCCGAUUUU |
| hsa-miR-5189 | 2218 | UCUGGGCACAGGCGGAUGGACAGG | 2219 | UGCCAACCGUCAGAGCCCAGA |
| hsa-miR-518a | 2220 | GAAAGCGCUUCCCUUUGCUGGA | 2221 | CUGCAAAGGGAAGCCCUUUC |
| hsa-miR-518b | 2222 | CAAAGCGCUCCCCUUUAGAGGU | 2223 | CUCUAAAGGGGAGCGCUUUGUU |
| hsa-miR-518c | 2224 | CAAAGCGCUUCUCUUUAGAGUGU | 2225 | UCUCUGGAGGGAAGCACUUUCUG |
| hsa-miR-518d | 2226 | CUCUAGAGGGAAGCACUUUCUG | 2227 | CAAAGCGCUUCCCUUUGGAGC |
| hsa-miR-518e | 2228 | CUCUAGAGGGAAGCGCUUUCUG | 2229 | AAAGCGCUUCCCUUCAGAGUG |
| hsa-miR-518f | 2230 | CUCUAGAGGGAAGCACUUUCUC | 2231 | GAAAGCGCUUCUCUUUAGAGG |
| hsa-miR-5190 | 2232 | CCAGUGACUGAGCUGGAGCCA | 2233 | GCUCCAGCUCAGUCACUGGUU |
| hsa-miR-5191 | 2234 | AGGAUAGGAAGAAUGAAGUGCU | 2235 | CACUUCAUUCUUCCUAUCCUUU |
| hsa-miR-5192 | 2236 | AGGAGAGUGGAUUCCAGGUGGU | 2237 | CACCUGGAAUCCACUCUCCUUU |
| hsa-miR-5193 | 2238 | UCCUCCUCUACCUCAUCCCAGU | 2239 | UGGGAUGAGGUAGAGGAGGAUU |
| hsa-miR-5194 | 2240 | UGAGGGUUUGGAAUGGGAUGG | 2241 | AUCCCAUUCCAAACCCCUCAUU |
| hsa-miR-5195 | 2242 | AACCCUAAGGCAACUGGAUGG | 2243 | AUCCAGUUCUCUGAGGGGCU |
| hsa-miR-5196 | 2244 | AGGGAAGGGGACGAGGGUUGGG | 2245 | UCAUCCCGUCUCCCUCCCAG |
| hsa-miR-5197 | 2246 | AAGAAGAGACUGAGUCAUCGAAU | 2247 | CAAUGGCACAAACUCAUUCUUGA |
| hsa-miR-519a | 2248 | CUCUAGAGGGAAGCGCUUUCUG | 2249 | AAAGUGCAUCCUUUUAGAGUGU |
| hsa-miR-519b | 2250 | AAAGUGCAUCCUUUUAGAGGUU | 2251 | CUCUAGAGGGAAGCGCUUUCUG |
| hsa-miR-519c | 2252 | AAAGUGCAUCUUUUUAGAGGAU | 2253 | CUCUAGAGGGAAGCGCUUUCUG |
| hsa-miR-519d | 2254 | CAAAGUGCCUCCCUUUAGAGUG | 2255 | CCUCCAAAGGGAAGCGCUUUCUGUU |
| hsa-miR-519e | 2256 | UUCUCCAAAAGGGAGCACUUUC | 2257 | AAGUGCCUCCUUUUAGAGUGUU |
| hsa-miR-520a | 2258 | AAAGUGCUUCCCUUUGGACUGU | 2259 | CUCCAGAGGGAAGUACUUUCU |

TABLE 1-continued miRNA Sequences

| miRNA | SEQ ID NO: | Sequence 1 | SEQ ID NO: | Sequence 2 |
|---|---|---|---|---|
| hsa-miR-520b | 2260 | AAAGUGCUUCCUUUUAGAGGG | 2261 | CUCUAAAAGGAAGCACUUUUU |
| hsa-miR-520c | 2262 | CUCUAGAGGGAAGCACUUUCUG | 2263 | AAAGUGCUUCCUUUUAGAGGGU |
| hsa-miR-520d | 2264 | CUACAAAGGGAAGCCCUUUC | 2265 | AAAGUGCUUCUCUUUGGUGGGU |
| hsa-miR-520e | 2266 | AAAGUGCUUCCUUUUUGAGGG | 2267 | CUCAAAAGGAAGCACUUUUU |
| hsa-miR-520f | 2268 | CCUCUAAAGGGAAGCGCUUUCU | 2269 | AAGUGCUUCCUUUUAGAGGGUU |
| hsa-miR-520g | 2270 | UCUAGAGGAAGCACUUUCUGUUU | 2271 | ACAAAGUGCUUCCCUUUAGAGUGU |
| hsa-miR-520h | 2272 | ACAAAGUGCUUCCCUUUAGAGU | 2273 | UCUAAGGGAAGCACUUUGUUU |
| hsa-miR-521 | 2274 | AACGCACUUCCCUUUAGAGUGU | 2275 | ACUCUAAAGGGAAGUGCGUUUU |
| hsa-miR-522 | 2276 | CUCUAGAGGGAAGCGCUUUCUG | 2277 | AAAAUGGUUCCCUUUAGAGUGU |
| hsa-miR-523 | 2278 | CUCUAGAGGGAAGCGCUUUCUG | 2279 | GAACGCGCUUCCCUAUAGAGGGU |
| hsa-miR-524 | 2280 | GAAGGCGCUUCCCUUUGGAGU | 2281 | CUACAAAGGGAAGCACUUUCUC |
| hsa-miR-525 | 2282 | CUCCAGAGGGAUGCACUUUCU | 2283 | GAAGGCGCUUCCCUUUAGAGCG |
| hsa-miR-526a | 2284 | CUCUAGAGGGAAGCACUUUCUG | 2285 | GAAAGUGCUUCCCUCUAGAGUU |
| hsa-miR-526b | 2286 | GAAAGUGCUUCCUUUUAGAGGC | 2287 | CUCUUGAGGGAAGCACUUUCUGU |
| hsa-miR-527 | 2288 | CUGCAAAGGGAAGCCCUUUC | 2289 | AAGGGCUUCCCUUUGCAGUU |
| hsa-miR-532 | 2290 | CCUCCCACACCCAAGGCUUGCA | 2291 | CAUGCCUUGAGUGUAGGACCGU |
| hsa-miR-539 | 2292 | GGAGAAAUUAUCCUUGGUGUGU | 2293 | AUCAUACAAGGACAAUUUCUUU |
| hsa-miR-541 | 2294 | UGGUGGGCACAGAAUCUGGACU | 2295 | AAAGGAUUCUGCUGUCGGUCCCACU |
| hsa-miR-542 | 2296 | UGUGACAGAUUGAUAACUGAAA | 2297 | UCGGGGAUCAUCAUGUCACGAGA |
| hsa-miR-543 | 2298 | AAACAUUCGCGGUGCACUUCUU | 2299 | GAAGUGCACCGCGAAUGUUUU |
| hsa-miR-544a | 2300 | AUUCUGCAUUUUUAGCAAGUUC | 2301 | ACUUGCUAAAAAUGCAGAAUUU |
| hsa-miR-544b | 2302 | ACCUGAGGUUGUGCAUUUCUAA | 2303 | AGAAAUGCACAACCUCAGGUUU |
| hsa-miR-545 | 2304 | UCAGUAAAUGUUUAUUAGAUGA | 2305 | UCAGCAAACAUUUAUUGUGUGC |
| hsa-miR-548a | 2306 | CAAAACUGGCAAUUACUUUUGC | 2307 | AAAAGUAUUGCGAGUUUUACC |
| hsa-miR-548aa | 2308 | AAAAACCACAAUUACUUUUGCACCA | 2309 | GUGCAAAAGUAAUUGUGGUUUUUUU |
| hsa-miR-548ab | 2310 | AAAAGUAAUUGUGGAUUUUGCU | 2311 | CAAAAUCCACAAUUACUUUUUU |
| hsa-miR-548ac | 2312 | CAAAAACCGGCAAUUACUUUUG | 2313 | AAAGUAAUUGCCGGUUUUUGUU |
| hsa-miR-548ad | 2314 | AAAAGUAAUUGUGGUUUUUG | 2315 | GAAAACGACAAUGACUUUUGCA |
| hsa-miR-548ae | 2316 | CAAAAACUGCAAUUACUUUCA | 2317 | AAAAGUAAUUGUGGUUUUUG |
| hsa-miR-548ag | 2318 | AAAGGUAAUUGUGGUUUCUGC | 2319 | AGAAACCACAAUUACCUUUUU |
| hsa-miR-548ah | 2320 | CAAAAACUGCAGUUACUUUUGC | 2321 | AAAAGUGAUUGCAGUGUUUG |
| hsa-miR-548ai | 2322 | AAAGGUAAUUGCAGUUUUUCCC | 2323 | GAAAACUGCAAUUACCUUUUU |
| hsa-miR-548aj | 2324 | UGCAAAAGUAAUUGCAGUUUUUG | 2325 | UAAAAACUGCAAUUACUUUUA |
| hsa-miR-548ak | 2326 | AAAAGUAACUGCGGUUUUUGA | 2327 | AAAACCGCAGUUACUUUUUU |
| hsa-miR-548al | 2328 | AACGGCAAUGACUUUUGUACCA | 2329 | GUACAAAAGUCAUUGCCGUUUU |
| hsa-miR-548am | 2330 | AAAAGUAAUUGCGGUUUUUGCC | 2331 | CAAAAACUGCAGUUACUUUUGU |
| hsa-miR-548an | 2332 | AAAAGGCAUUGUGGUUUUUG | 2333 | AAAACCACAAUGCCUUUUUU |
| hsa-miR-548ao | 2334 | AGAAGUAACUACGGUUUUUGCA | 2335 | AAAGACCGUGACUACUUUUGCA |

TABLE 1-continued miRNA Sequences

| miRNA | SEQ ID NO: | Sequence 1 | SEQ ID NO: | Sequence 2 |
|---|---|---|---|---|
| hsa-miR-548ap | 2336 | AAAAGUAAUUGCGGUCUUU | 2337 | AAAAACCACAAUUACUUUU |
| hsa-miR-548aq | 2338 | GAAAGUAAUUGCUGUUUUUGCC | 2339 | CAAAAACUGCAAUUACUUUUGC |
| hsa-miR-548ar | 2340 | AAAAGUAAUUGCAGUUUUUGC | 2341 | UAAAACUGCAGUUAUUUUUGC |
| hsa-miR-548as | 2342 | UAAACCCACAAUUAUGUUUGU | 2343 | AAAAGUAAUUGCGGGUUUUGCC |
| hsa-miR-548at | 2344 | AAAAGUUAUUGCGGUUUUGGCU | 2345 | CAAAACCGCAGUAACUUUUGU |
| hsa-miR-548au | 2346 | UGGCAGUUACUUUUGCACCAG | 2347 | AAAAGUAAUUGCGGUUUUUGC |
| hsa-miR-548av | 2348 | AAAACUGCAGUUACUUUUGC | 2349 | AAAAGUACUUGCGGAUUU |
| hsa-miR-548aw | 2350 | GUGCAAAAGUCAUCACGGUU | 2351 | CCGUGAUGACUUUUGCACUU |
| hsa-miR-548ax | 2352 | AGAAGUAAUUGCGGUUUUGCCA | 2353 | GCAAAACCGCAAUUACUUCUUU |
| hsa-miR-548ay | 2354 | CAAAACCGCGAUUACUCUUGCA | 2355 | AAAAGUAAUUGUGGUUUUUGC |
| hsa-miR-548az | 2356 | AAAAACUGCAAUCACUUUUGC | 2357 | CAAAAGUGAUUGUGGUUUUUGC |
| hsa-miR-548b | 2358 | AAAAGUAAUUGUGGUUUUGGCC | 2359 | CAAGAACCUCAGUUGCUUUUGU |
| hsa-miR-548ba | 2360 | AAAGGUAACUGUGAUUUUUGCU | 2361 | CAAAAAUCACAGUUACCUUUUU |
| hsa-miR-548bb | 2362 | AAAAGUAACUAUGGUUUUUGCC | 2363 | CAAAAACCAUAGUUACUUUUGC |
| hsa-miR-548c | 2364 | AAAAGUAAUUGCGGUUUUUGCC | 2365 | CAAAAUCUCAAUUACUUUUGC |
| hsa-miR-548d | 2366 | CAAAAACCACAGUUUCUUUUGC | 2367 | AAAAGUAAUUGUGGUUUUUGCC |
| hsa-miR-548e | 2368 | AAAAACUGAGACUACUUUUGCA | 2369 | CAAAAGCAAUCGCGGUUUUUGC |
| hsa-miR-548f | 2370 | AAAAACUGUAAUUACUUUU | 2371 | UGCAAAAGUAAUCACAGUUUUU |
| hsa-miR-548g | 2372 | UGCAAAAGUAAUUGCAGUUUUUG | 2373 | AAAACUGUAAUUACUUUUGUAC |
| hsa-miR-548h | 2374 | CAAAAACCGCAAUUACUUUUGCA | 2375 | AAAAGUAAUCGCGGUUUUUGUC |
| hsa-miR-548i | 2376 | AAAAGUAAUUGCGGAUUUUGCC | 2377 | CAAAAUCCGCAAUUACUUUUUU |
| hsa-miR-548j | 2378 | CAAAAACUGCAUUACUUUUGC | 2379 | AAAAGUAAUUGCGGUCUUUGGU |
| hsa-miR-548k | 2380 | AAAAGUACUUGCGGAUUUUGCU | 2381 | CAAAAUCCGCAAGUACUUUUUU |
| hsa-miR-548l | 2382 | AAAAGUAUUUGCGGGUUUUGUC | 2383 | CAAAACCCGCAAAUACUUUUUU |
| hsa-miR-548m | 2384 | CAAAGGUAUUUGUGGUUUUUG | 2385 | AAAACCACAAAUACCUUUGUU |
| hsa-miR-548n | 2386 | CAAAAGUAAUUGUGGAUUUUGU | 2387 | AAAAUCCACAAUUACUUUUGUU |
| hsa-miR-548o | 2388 | CCAAAACUGCAGUUACUUUUGC | 2389 | AAAAGUAAUUGCGGUUUUUGCC |
| hsa-miR-548p | 2390 | UAGCAAAAACUGCAGUUACUUU | 2391 | AGUAACUGCAGUUUUUGCUAUU |
| hsa-miR-548q | 2392 | GCUGGUGCAAAAGUAAUGGCGG | 2393 | GCCAUUACUUUUGCACCAGCUU |
| hsa-miR-548s | 2394 | AUGGCCAAAACUGCAGUUAUUUU | 2395 | AAUAACUGCAGUUUUUGGCCAUU |
| hsa-miR-548t | 2396 | AAAACCACAAUUACUUUUGCACCA | 2397 | CAAAAGUGAUCGUGGUUUUUG |
| hsa-miR-548u | 2398 | CAAAGACUGCAAUUACUUUUGCG | 2399 | CAAAAGUAAUUGCAGUCUUUGUU |
| hsa-miR-548v | 2400 | AGCUACAGUUACUUUUGCACCA | 2401 | GUGCAAAAGUAACUGUAGCUUU |
| hsa-miR-548w | 2402 | AAAAGUAACUGCGGUUUUUGCCU | 2403 | GCAAAACCGCAGUUACUUUUUU |
| hsa-miR-548x | 2404 | UGCAAAAGUAAUUGCAGUUUUUG | 2405 | UAAAAACUGCAAUUACUUUC |
| hsa-miR-548y | 2406 | AAAAGUAAUCACGUUUUUGCC | 2407 | CAAAAACAGUGAUUACUUUUUU |
| hsa-miR-548z | 2408 | CAAAACCGCAAUUACUUUUGCA | 2409 | CAAAAGUAAUUGCGGUUUUUGUU |

TABLE 1-continued miRNA Sequences

| miRNA | SEQ ID NO: | Sequence 1 | SEQ ID NO: | Sequence 2 |
|---|---|---|---|---|
| hsa-miR-549a | 2410 | UGACAACUAUGGAUGAGCUCU | 2411 | AGCUCAUCCAUAGUUGUCAUU |
| hsa-miR-550a-1 | 2412 | UGUCUUACUCCCUCAGGCACAU | 2413 | AGUGCCUGAGGGAGUAAGAGCCC |
| hsa-miR-550a-3 | 2414 | UGUCUUACUCCCUCAGGCACAU | 2415 | AGUGCCUGAGGGAGUAAGAG |
| hsa-miR-550b | 2416 | UCUUACUCCCUCAGGCACUG | 2417 | AUGUGCCUGAGGGAGUAAGACA |
| hsa-miR-551a | 2418 | GCGACCCACUCUUGGUUUCCA | 2419 | GAAACCAAGAGUGGGUCGCUU |
| hsa-miR-551b | 2420 | GAAAUCAAGCGUGGGUGAGACC | 2421 | GCGACCCAUACUUGGUUUCAG |
| hsa-miR-552 | 2422 | GUUUAACCUUUUGCCUGUUGG | 2423 | AACAGGUGACUGGUUAGACAA |
| hsa-miR-553 | 2424 | AAAACGGUGAGAUUUUGUUUU | 2425 | AACAAAAUCUCACCGUUUUUU |
| hsa-miR-554 | 2426 | GCUAGUCCUGACUCAGCCAGU | 2427 | UGGCUGAGUCAGGACUAGCUU |
| hsa-miR-555 | 2428 | AGGGUAAGCUGAACCUCUGAU | 2429 | CAGAGGUUCAGCUUACCCUUU |
| hsa-miR-556 | 2430 | GAUGAGCUCAUUGUAAUAUGAG | 2431 | AUAUUACCAUUAGCUCAUCUUU |
| hsa-miR-557 | 2432 | GUUUGCACGGGUGGGCCUUGUCU | 2433 | ACAAGGCCCACCCGUGCAAACUU |
| hsa-miR-5571 | 2434 | GUCCUAGGAGGCUCCUCUG | 2435 | CAAUUCUCAAAGGAGCCUCCC |
| hsa-miR-5572 | 2436 | GUUGGGGUGCAGGGGUCUGCU | 2437 | CAGACCCCUGCACCCCAACUU |
| hsa-miR-5579 | 2438 | UAUGGUACUCCUUAAGCUAAC | 2439 | UUAGCUUAAGGAGUACCAGAUC |
| hsa-miR-558 | 2440 | UGAGCUGCUGUACCAAAAU | 2441 | UUUGGUACAGCAGCUCAUU |
| hsa-miR-5580 | 2442 | CACAUAUGAAGUGAGCCAGCAC | 2443 | UGCUGGCUCAUUUCAUAUGUGU |
| hsa-miR-5581 | 2444 | AGCCUUCCAGGAGAAAUGGAGA | 2445 | UUCCAUGCCUCCUAGAAGUUCC |
| hsa-miR-5582 | 2446 | UAAAACUUUAAGUGUGCCUAGG | 2447 | UAGGCACACUUAAAGUUAUAGC |
| hsa-miR-5583 | 2448 | GAAUAUGGGUAUAUUAGUUUGG | 2449 | AAACUAAAUAUACCCAUAUUCUG |
| hsa-miR-5584 | 2450 | CAGGGAAAUGGGAAGAACUAGA | 2451 | UAGUUCUUCCCUUUGCCCAAUU |
| hsa-miR-5585 | 2452 | CUGAAUAGCUGGGACUACAGGU | 2453 | UGAAGUACCAGCUACUCGAGAG |
| hsa-miR-5586 | 2454 | UAUCCAGCUUGUUACUAUAUGC | 2455 | CAGAGUGACAAGCUGGUUAAAG |
| hsa-miR-5587 | 2456 | AUGGUCACCUCCGGGACU | 2457 | GCCCCGGGCAGUGAUCAUC |
| hsa-miR-5588 | 2458 | ACUGGCAUUAGUGGGACUUUU | 2459 | AAGUCCCACUAAUGCCAGC |
| hsa-miR-5589 | 2460 | GGCUGGGUGCUCUUGUGCAGU | 2461 | UGCACAUGGCAACCUAGCUCCCA |
| hsa-miR-559 | 2462 | UAAAGUAAAUAUGCACCAAAA | 2463 | UUGGUGCAUAUUUACUUUAUU |
| hsa-miR-5590 | 2464 | AAUAAAGUUCAUGUAUGGCAA | 2465 | UUGCCAUACAUGACUUUAUU |
| hsa-miR-5591 | 2466 | UGGGAGCUAAGCUAUGGGUAU | 2467 | AUACCCAUAGCUUAGCUCCCA |
| hsa-miR-561 | 2468 | CAAAGUUUAAGAUCCUUGAAGU | 2469 | AUCAAGGAUCUUAAACUUUGCC |
| hsa-miR-562 | 2470 | AAAGUAGCUGUACCAUUUGC | 2471 | AAAUGGUACAGCUACUUUUU |
| hsa-miR-563 | 2472 | AGGUUGACAUACGUUUCCC | 2473 | GAAACGUAUGUCAACCUUU |
| hsa-miR-564 | 2474 | AGGCACGGUGUCAGCAGGC | 2475 | CUGCUGACACCGUGCCUUU |
| hsa-miR-566 | 2476 | GGGCGCCUGUGAUCCCAAC | 2477 | UGGGAUCACAGGCGCCCUU |
| hsa-miR-567 | 2478 | AGUAUGUUCUUCCAGGACAGAAC | 2479 | UCUGUCCUGGAAGAACAUACUUU |
| hsa-miR-568 | 2480 | AUGUAUAAAUGUAUACACAC | 2481 | GUGUAUACAUUUAUACAUUU |
| hsa-miR-5680 | 2482 | GAGAAAUGCUGGACUAAUCUGC | 2483 | AGAUUAGUCCAGCAUUUCUCUU |
| hsa-miR-5681a | 2484 | AGAAAGGGUGGCAAUACCUCUU | 2485 | GAGGUAUUGCCACCCUUUCUUU |

TABLE 1-continued miRNA Sequences

| miRNA | SEQ ID NO: | Sequence 1 | SEQ ID NO: | Sequence 2 |
|---|---|---|---|---|
| hsa-miR-5681b | 2486 | AGGUAUUGCCACCCUUUCUAGU | 2487 | UAGAAAGGGUGGCAAUACCUUU |
| hsa-miR-5682 | 2488 | GUAGCACCUUGCAGGAUAAGGU | 2489 | CUUAUCCUGCAAGGUGCUACUU |
| hsa-miR-5683 | 2490 | UACAGAUGCAGAUUCUCUGACUUC | 2491 | AGUCAGAGAAUCUGCAUCUGUAUU |
| hsa-miR-5684 | 2492 | AACUCUAGCCUGAGCAACAG | 2493 | GUUGCUCAGGCUAGAGUUUU |
| hsa-miR-5685 | 2494 | ACAGCCCAGCAGUUAUCACGGG | 2495 | CGUGAUAACUGCUGGGCUGUUU |
| hsa-miR-5687 | 2496 | UUAGAACGUUUUAGGGUCAAAU | 2497 | UUGACCCUAAAACGUUCUAAUU |
| hsa-miR-5688 | 2498 | UAACAAACACCUGUAAAACAGC | 2499 | UGUUUUACAGGUGUUUGUUAUU |
| hsa-miR-5689 | 2500 | AGCAUACACCUGUAGUCCUAGA | 2501 | UAGGACUACAGGUGUAUGCUUU |
| hsa-miR-569 | 2502 | AGUUAAUGAAUCCUGGAAAGU | 2503 | UUUCCAGGAUUCAUUAACUUU |
| hsa-miR-5690 | 2504 | UCAGCUACUACCUCUAUUAGG | 2505 | UAAUAGAGGUAGUAGCUGAUU |
| hsa-miR-5691 | 2506 | UUGCUCUGAGCUCCGAGAAAGC | 2507 | UUUCUCGGAGCUCAGAGCAAUU |
| hsa-miR-5692a | 2508 | CAAAUAAUACCACAGUGGGUGU | 2509 | ACCCACUGUGGUAUUAUUUGUU |
| hsa-miR-5692b | 2510 | AAUAAUAUCACAGUAGGUGU | 2511 | ACCUACUGUGAUAUUAUUUU |
| hsa-miR-5692c | 2512 | AAUAAUAUCACAGUAGGUGUAC | 2513 | ACACCUACUGUGAUAUUAUUUU |
| hsa-miR-5693 | 2514 | GCAGUGGCUCUGAAAUGAACUC | 2515 | GUUCAUUUCAGAGCCACUGCUU |
| hsa-miR-5694 | 2516 | CAGAUCAUGGGACUGUCUCAG | 2517 | GAGACAGUCCCAUGAUCUGUU |
| hsa-miR-5695 | 2518 | ACUCCAAGAAGAAUCUAGACAG | 2519 | GUCUAGAUUCUUCUUGGAGUUU |
| hsa-miR-5696 | 2520 | CUCAUUUAAGUAGUCUGAUGCC | 2521 | CAUCAGACUACUUAAAUGAGUU |
| hsa-miR-5697 | 2522 | UCAAGUAGUUUCAUGAUAAAGG | 2523 | UUUAUCAUGAAACUACUUGAUU |
| hsa-miR-5698 | 2524 | UGGGGGAGUGCAGUGAUUGUGG | 2525 | ACAAUCACUGCACUCCCCCAUU |
| hsa-miR-5699 | 2526 | UCCUGUCUUUCCUUGUUGGAGC | 2527 | UGCCCAACAAGGAAGGACAAG |
| hsa-miR-570 | 2528 | CGAAAACAGCAAUUACCUUUGC | 2529 | AAAGGUAAUUGCAGUUUUCCC |
| hsa-miR-5700 | 2530 | UAAUGCAUUAAAUUAUUGAAGG | 2531 | UUCAAUAAUUUAAUGCAUUAUU |
| hsa-miR-5701 | 2532 | UUAUUGUCACGUUCUGAUU | 2533 | UCAGAACGUGACAAUAAUU |
| hsa-miR-5702 | 2534 | UGAGUCAGCAACAUAUCCCAUG | 2535 | UGGGAUAUGUUGCUGACUCAUU |
| hsa-miR-5703 | 2536 | AGGAGAAGUCGGGAAGGU | 2537 | CUUCCCGACUUCUCCUUU |
| hsa-miR-5704 | 2538 | UUAGGCCAUCAUCCCAUUAUGC | 2539 | AUAAUGGGAUGAUGGCCUAAUU |
| hsa-miR-5705 | 2540 | UGUUUCGGGGCUCAUGGCCUGUG | 2541 | CAGGCCAUGAGCCCCGAAACAUU |
| hsa-miR-5706 | 2542 | UUCUGGAUAACAUGCUGAAGCU | 2543 | CUUCAGCAUGUUAUCCAGAAUU |
| hsa-miR-5707 | 2544 | ACGUUUGAAUGCUGUACAAGGC | 2545 | CUUGUACAGCAUUCAAACGUUU |
| hsa-miR-5708 | 2546 | AUGAGCGACUGUGCCUGACC | 2547 | UCAGGCACAGUCGCUCAUUU |
| hsa-miR-571 | 2548 | UGAGUUGGCCAUCUGAGUGAG | 2549 | CACUCAGAUGGCCAACUCAUU |
| hsa-miR-572 | 2550 | GUCCGCUCGGCGGUGGCCCA | 2551 | GGCCACCGCCGAGCGGACUU |
| hsa-miR-573 | 2552 | CUGAAGUGAUGUGUAACUGAUCAG | 2553 | GAUCAGUUACACAUCACUUCAGUU |
| hsa-miR-5739 | 2554 | GCGGAGAGAGAAUGGGGAGC | 2555 | UCCCCAUUCUCUCUCCGCUU |
| hsa-miR-574 | 2556 | UGAGUGUGUGUGUGUGAGUGUGU | 2557 | CACGCUCAUGCACACACCCACA |
| hsa-miR-575 | 2558 | GAGCCAGUUGGACAGGAGC | 2559 | UCCUGUCCAACUGGCUCUU |

TABLE 1-continued miRNA Sequences

| miRNA | SEQ ID NO: | Sequence 1 | SEQ ID NO: | Sequence 2 |
|---|---|---|---|---|
| hsa-miR-576 | 2560 | AAGAUGUGGAAAAAUUGGAAUC | 2561 | AUUCUAAUUUCUCCACGUCUUU |
| hsa-miR-577 | 2562 | UAGAUAAAAUAUUGGUACCUG | 2563 | GGUACCAAUAUUUUAUCUAUU |
| hsa-miR-578 | 2564 | CUUCUUGUGCUCUAGGAUUGU | 2565 | AAUCCUAGAGCACAAGAAGUU |
| hsa-miR-5787 | 2566 | GGGCUGGGGCGCGGGGAGGU | 2567 | CUCCCCGCGCCCAGCCCUU |
| hsa-miR-579 | 2568 | UUCAUUUGGUAUAAACCGCGAUU | 2569 | UCGCGGUUUGUGCCAGAUGACG |
| hsa-miR-580 | 2570 | UAAUGAUUCAUCAGACUCAGAU | 2571 | UUGAGAAUGAUGAAUCAUUAGG |
| hsa-miR-581 | 2572 | UCUUGUGUUCUCUAGAUCAGU | 2573 | UGAUCUAGAGAACACAAGAUU |
| hsa-miR-582 | 2574 | UUACAGUUGUUCAACCAGUUACU | 2575 | UAACUGGUUGAACAACUGAACC |
| hsa-miR-583 | 2576 | CAAAGAGGAAGGUCCCAUUAC | 2577 | AAUGGGACCUUCCUCUUUGUU |
| hsa-miR-584 | 2578 | UUAUGGUUUGCCUGGGACUGAG | 2579 | UCAGUUCCAGGCCAACCAGGCU |
| hsa-miR-585 | 2580 | UGGGCGUAUCUGUAUGCUA | 2581 | CUAGCACACAGAUACGCCCAGA |
| hsa-miR-586 | 2582 | UAUGCAUUGUAUUUUUAGGUCC | 2583 | ACCUAAAAAUACAAUGCAUAUU |
| hsa-miR-587 | 2584 | UUUCCAUAGGUGAUGAGUCAC | 2585 | GACUCAUCACCUAUGGAAAUU |
| hsa-miR-588 | 2586 | UUGGCCACAAUGGGUUAGAAC | 2587 | UCUAACCCAUUGUGGCCAAUU |
| hsa-miR-589 | 2588 | UCAGAACAAAUGCCGGUUCCCAGA | 2589 | UGAGAACCACGUCUGCUCUGAG |
| hsa-miR-590 | 2590 | GAGCUUAUUCAUAAAAGUGCAG | 2591 | UAAUUUUAUGUAUAAGCUAGU |
| hsa-miR-591 | 2592 | AGACCAUGGGUUCUCAUUGU | 2593 | AAUGAGAACCCAUGGUCUUU |
| hsa-miR-592 | 2594 | UUGUGUCAAUAUGCGAUGAUGU | 2595 | AUCAUCGCAUAUUGACACAAUU |
| hsa-miR-593 | 2596 | UGUCUCUGCUGGGGUUUCU | 2597 | AGGCACCAGCCAGGCAUUGCUCAGC |
| hsa-miR-595 | 2598 | GAAGUGUGCCGUGGUGUGUCU | 2599 | ACACACCACGGCACACUUCUU |
| hsa-miR-596 | 2600 | AAGCCUGCCCGGCUCCUCGGG | 2601 | CGAGGAGCCGGGCAGGCUUUU |
| hsa-miR-597 | 2602 | UGGUUCUCUUGUGGCUCAAGCGU | 2603 | UGUGUCACUCGAUGACCACUGU |
| hsa-miR-598 | 2604 | UACGUCAUCGUUGUCAUCGUCA | 2605 | GCGGUGAUCCCGAUGGUGUGAGC |
| hsa-miR-599 | 2606 | GUUUGUGUCAGUUUAUCAAAC | 2607 | UUGAUAAACUGACACAACUU |
| hsa-miR-600 | 2608 | ACUUACAGACAAGAGCCUUGCUC | 2609 | GCAAGGCUCUUGUCUGUAAGUUU |
| hsa-miR-601 | 2610 | UGGUCUAGGAUUGUUGGAGGAG | 2611 | CCUCCAACAAUCCUAGACCAUU |
| hsa-miR-602 | 2612 | GACACGGGCGACAGCUGCGGCCC | 2613 | GCCGCAGCUGUCGCCCGUGUCUU |
| hsa-miR-603 | 2614 | CACACACUGCAAUUACUUUUGC | 2615 | AAAAGUAAUUGCAGUGUGUGUU |
| hsa-miR-604 | 2616 | AGGCUGCGGAAUUCAGGAC | 2617 | CCUGAAUUCCGCAGCCUUU |
| hsa-miR-605 | 2618 | AGAAGGCACUAUGAGAUUUAGA | 2619 | UAAAUCCCAUGGUGCCUUCUCCU |
| hsa-miR-606 | 2620 | AAACUACUGAAAAUCAAAGAU | 2621 | CUUUGAUUUUCAGUAGUUUU |
| hsa-miR-6068 | 2622 | CCUGCGAGUCUCCGGCGGUGG | 2623 | ACCGCCGGAGACUCGCAGGUU |
| hsa-miR-6069 | 2624 | GGGCUAGGGCCUGCUGCCCCC | 2625 | GGGCAGCAGGCCCUAGCCCUU |
| hsa-miR-607 | 2626 | GUUCAAAUCCAGAUCUAUAAC | 2627 | UAUAGAUCUGGAUUUGAACUU |
| hsa-miR-6070 | 2628 | CCGGUUCCAGUCCCUGGAG | 2629 | CCAGGGACUGGAACCGGUU |
| hsa-miR-6071 | 2630 | UUCUGCUGCCGGCCAAGGC | 2631 | CUUGGCCGGCAGCAGAAUU |
| hsa-miR-6072 | 2632 | UCCUCAUCACACUGCACCUUAG | 2633 | AAGGUGCAGUGUGAUGAGGAUU |
| hsa-miR-6073 | 2634 | GGUAGUGAGUUAUCAGCUAC | 2635 | AGCUGAUAACUCACUACCUU |

TABLE 1-continued miRNA Sequences

| miRNA | SEQ ID NO: | Sequence 1 | SEQ ID NO: | Sequence 2 |
|---|---|---|---|---|
| hsa-miR-6074 | 2636 | GAUAUUCAGAGGCUAGGUGG | 2637 | ACCUAGCCUCUGAAUAUCUU |
| hsa-miR-6075 | 2638 | ACGGCCCAGGCGGCAUUGGUG | 2639 | CCAAUGCCGCCUGGGCCGUUU |
| hsa-miR-6076 | 2640 | AGCAUGACAGAGGAGAGGUGG | 2641 | ACCUCUCCUCUGUCAUGCUUU |
| hsa-miR-6077 | 2642 | GGGAAGAGCUGUACGGCCUUC | 2643 | AGGCCGUACAGCUCUUCCCUU |
| hsa-miR-6078 | 2644 | CCGCCUGAGCUAGCUGUGG | 2645 | ACAGCUAGCUCAGGCGGUU |
| hsa-miR-6079 | 2646 | UUGGAAGCUUGGACCAACUAGCUG | 2647 | GCUAGUUGGUCCAAGCUUCCAAUU |
| hsa-miR-608 | 2648 | AGGGGUGGUGUUGGGACAGCUCCGU | 2649 | GGAGCUGUCCCAACACCACCCCUUU |
| hsa-miR-6080 | 2650 | UCUAGUGCGGGCGUUCCCG | 2651 | GGAACGCCCGCACUAGAUU |
| hsa-miR-6081 | 2652 | AGGAGCAGUGCCGGCCAAGGCGCC | 2653 | CGCCUUGGCCGGCACUGCUCCUUU |
| hsa-miR-6082 | 2654 | GAAUACGUCUGGUUGAUCC | 2655 | AUCAACCAGACGUAUUCUU |
| hsa-miR-6083 | 2656 | CUUAUAUCAGAGGCUGUGGG | 2657 | CACAGCCUCUGAUAUAAGUU |
| hsa-miR-6084 | 2658 | UUCCGCCAGUCGGUGGCCGG | 2659 | GGCCACCGACUGGCGGAAUU |
| hsa-miR-6085 | 2660 | AAGGGGCUGGGGGAGCACA | 2661 | UGCUCCCCAGCCCCUUUU |
| hsa-miR-6086 | 2662 | GGAGGUUGGGAAGGGCAGAG | 2663 | CUGCCCUUCCCAACCUCCUU |
| hsa-miR-6087 | 2664 | UGAGGCGGGGGGGCGAGC | 2665 | UCGCCCCCCGCCUCAUU |
| hsa-miR-6088 | 2666 | AGAGAUGAAGCGGGGGGGCG | 2667 | CCCCCCGCUUCAUCUCUUU |
| hsa-miR-6089 | 2668 | GGAGGCCGGGGUGGGCGGGGCGG | 2669 | GCCCCGCCCCACCCCGGCCUCCUU |
| hsa-miR-609 | 2670 | AGGGUGUUUCUCUCAUCUCU | 2671 | AGAUGAGAGAAACACCCUUU |
| hsa-miR-6090 | 2672 | GGGGAGCGAGGGGCGGGGC | 2673 | CCCGCCCCUCGCUCCCCUU |
| hsa-miR-610 | 2674 | UGAGCUAAAUGUGUGCUGGGA | 2675 | CCAGCACACAUUUAGCUCAUU |
| hsa-miR-611 | 2676 | GCGAGGACCCCUCGGGGUCUGAC | 2677 | CAGACCCGAGGGGUCCUCGCUU |
| hsa-miR-612 | 2678 | GCUGGGCAGGGCUUCUGAGCUCCUU | 2679 | GGAGCUCAGAAGCCCUGCCCAGCUU |
| hsa-miR-6124 | 2680 | GGGAAAAGGAAGGGGGAGGA | 2681 | CUCCCCCUUCCUUUUCCUU |
| hsa-miR-6125 | 2682 | GCGGAAGGCGGAGCGGCGGA | 2683 | CGCCGCUCCGCCUUCCGCUU |
| hsa-miR-6126 | 2684 | GUGAAGGCCCGGCGGAGA | 2685 | UCCGCCGGGCCUUCACUU |
| hsa-miR-6127 | 2686 | UGAGGGAGUGGGUGGGAGG | 2687 | UCCCACCCACUCCCUCAUU |
| hsa-miR-6128 | 2688 | ACUGGAAUUGGAGUCAAAA | 2689 | UUGACUCCAAUUCCAGUUU |
| hsa-miR-6129 | 2690 | UGAGGGAGUUGGGUGUAUA | 2691 | UACACCCAACUCCCUCAUU |
| hsa-miR-613 | 2692 | AGGAAUGUUCCUUCUUUGCC | 2693 | CAAAGAAGGAACAUUCCUUU |
| hsa-miR-6130 | 2694 | UGAGGGAGUGGAUUGUAUG | 2695 | UACAAUCCACUCCCUCAUU |
| hsa-miR-6131 | 2696 | GGCUGGUCAGAUGGGAGUG | 2697 | CUCCCAUCUGACCAGCCUU |
| hsa-miR-6132 | 2698 | AGCAGGGCUGGGGAUUGCA | 2699 | CAAUCCCAGCCCUGCUUU |
| hsa-miR-6133 | 2700 | UGAGGGAGGAGGUUGGGUA | 2701 | CCCAACCUCCUCCCUCAUU |
| hsa-miR-6134 | 2702 | UGAGGUGGUAGGAUGUAGA | 2703 | UACAUCCUACCACCUCAUU |
| hsa-miR-614 | 2704 | GAACGCCUGUUCUUGCCAGGUGG | 2705 | ACCUGGCAAGAACAGGCGUUCUU |
| hsa-miR-615 | 2706 | GGGGGUCCCCGGUGCUCGGAUC | 2707 | UCCGAGCUGGGUCUCCCUCUU |
| hsa-miR-616 | 2708 | ACUCAAAACCCUUCAGUGACUU | 2709 | AGUCAUUGGAGGGUUUGAGCAG |

TABLE 1-continued miRNA Sequences

| miRNA | SEQ ID NO: | Sequence 1 | SEQ ID NO: | Sequence 2 |
|---|---|---|---|---|
| hsa-miR-6165 | 2710 | CAGCAGGAGGUGAGGGGAG | 2711 | CCCCUCACCUCCUGCUGUU |
| hsa-miR-617 | 2712 | AGACUUCCCAUUUGAAGGUGGC | 2713 | CACCUUCAAAUGGGAAGUCUUU |
| hsa-miR-618 | 2714 | AAACUCUACUUGUCCUUCUGAGU | 2715 | UCAGAAGGACAAGUAGAGUUUUU |
| hsa-miR-619 | 2716 | GCUGGGAUUACAGGCAUGAGCC | 2717 | GACCUGGACAUGUUUGUGCCCAGU |
| hsa-miR-620 | 2718 | AUGGAGAUAGAUAUAGAAAU | 2719 | UUCUAUAUCUAUCUCCAUUU |
| hsa-miR-621 | 2720 | GGCUAGCAACAGCGCUUACCU | 2721 | GUAAGCGCUGUUGCUAGCCUU |
| hsa-miR-622 | 2722 | ACAGUCUGCUGAGGUUGGAGC | 2723 | UCCAACCUCAGCAGACUGUUU |
| hsa-miR-623 | 2724 | AUCCCUUGCAGGGGCUGUUGGGU | 2725 | CCAACAGCCCCUGCAAGGGAUUU |
| hsa-miR-624 | 2726 | UAGUACCAGUACCUUGUGUUCA | 2727 | CACAAGGUAUUGGUAUUACCU |
| hsa-miR-625 | 2728 | AGGGGGAAAGUUCUAUAGUCC | 2729 | GACUAUAGAACUUUCCCCCUCA |
| hsa-miR-626 | 2730 | AGCUGUCUGAAAAUGUCUU | 2731 | GACAUUUUCAGACAGCUUU |
| hsa-miR-627 | 2732 | UCUUUUCUUUGAGACUCACU | 2733 | GUGAGUCUCUAAGAAAAGAGGA |
| hsa-miR-628 | 2734 | UCUAGUAAGAGUGGCAGUCGA | 2735 | AUGCUGACAUAUUUACUAGAGG |
| hsa-miR-629 | 2736 | UGGGUUUACGUUGGGAGAACU | 2737 | GUUCUCCCAACGUAAGCCCAGC |
| hsa-miR-630 | 2738 | AGUAUUCUGUACCAGGGAAGGU | 2739 | CUUCCCUGGUACAGAAUACUUU |
| hsa-miR-631 | 2740 | AGACCUGGCCCAGACCUCAGC | 2741 | UGAGGUCUGGGCCAGGUCUUU |
| hsa-miR-632 | 2742 | GUGUCUGCUUCCUGUGGGA | 2743 | CCACAGGAAGCAGACACUU |
| hsa-miR-633 | 2744 | CUAAUAGUAUCUACCACAAUAAA | 2745 | UAUUGUGGUAGAUACUAUUAGUU |
| hsa-miR-634 | 2746 | AACCAGCACCCCAACUUUGGAC | 2747 | CCAAAGUUGGGGUGCUGGUUUU |
| hsa-miR-635 | 2748 | ACUUGGGCACUGAAACAAUGUCC | 2749 | ACAUUGUUUCAGUGCCCAAGUUU |
| hsa-miR-636 | 2750 | UGUGCUUGCUCGUCCCGCCCGCA | 2751 | CGGGCGGGACGAGCAAGCACAUU |
| hsa-miR-637 | 2752 | ACUGGGGGCUUUCGGGCUCUGCGU | 2753 | GCAGAGCCCGAAAGCCCCCAGUUU |
| hsa-miR-638 | 2754 | AGGGAUCGCGGGCGGGUGGCGGCCU | 2755 | GCCGCCACCCGCCCGCGAUCCCUUU |
| hsa-miR-639 | 2756 | AUCGCUGCGGUUGCGAGCGCUGU | 2757 | AGCGCUCGCAACCGCAGCGAUUU |
| hsa-miR-640 | 2758 | AUGAUCCAGGAACCUGCCUCU | 2759 | AGGCAGGUUCCUGGAUCAUUU |
| hsa-miR-641 | 2760 | AAAGACAUAGGAUAGAGUCACCUC | 2761 | GGUGACUCUAUCCUAUGUCUUUUU |
| hsa-miR-642a | 2762 | GUCCCUCUCCAAAUGUGUCUUG | 2763 | AGACACAUUUGGAGAGGGAACC |
| hsa-miR-642b | 2764 | GGUUCCCUCUCCAAAUGUGUCU | 2765 | AGACACAUUUGGAGAGGGACCC |
| hsa-miR-643 | 2766 | ACUUGUAUGCUAGCUCAGGUAG | 2767 | ACCUGAGCUAGCAUACAAGUUU |
| hsa-miR-644a | 2768 | AGUGUGGCUUUCUUAGAGC | 2769 | UCUAAGAAAGCCACACUUU |
| hsa-miR-645 | 2770 | UCUAGGCUGGUACUGCUGA | 2771 | AGCAGUACCAGCCUAGAUU |
| hsa-miR-646 | 2772 | AAGCAGCUGCCUCUGAGGC | 2773 | CUCAGAGGCAGCUGCUUUU |
| hsa-miR-647 | 2774 | GUGGCUGCACUCACUUCCUUC | 2775 | AGGAAGUGAGUGCAGCCACUU |
| hsa-miR-648 | 2776 | AAGUGUGCAGGGCACUGGU | 2777 | CAGUGCCCUGCACACUUUU |
| hsa-miR-649 | 2778 | AAACCUGUGUUGUUCAAGAGUC | 2779 | CUCUUGAACAACACAGGUUUUU |
| hsa-miR-6499 | 2780 | AGCAGUGUUUGUUUUGCCCACA | 2781 | UCGGGCGCAAGAGCACUGCAGU |
| hsa-miR-650 | 2782 | AGGAGGCAGCGCUCUCAGGAC | 2783 | CCUGAGAGCGCUGCCUCCUUU |
| hsa-miR-6500 | 2784 | ACACUUGUUGGGAUGACCUGC | 2785 | AGGAGCUAUCCACUCCAGGUGUCC |

TABLE 1-continued miRNA Sequences

| miRNA | SEQ ID NO: | Sequence 1 | SEQ ID NO: | Sequence 2 |
|---|---|---|---|---|
| hsa-miR-6501 | 2786 | CCAGAGCAGCCUGCGGUAACAGU | 2787 | AGUUGCCAGGGCUGCCUUUGGU |
| hsa-miR-6502 | 2788 | AGCUCUAGAAAGAUUGUUGACC | 2789 | UAGACCAUCUUUCUAGAGUAU |
| hsa-miR-6503 | 2790 | GGGACUAGGAUGCAGACCUCC | 2791 | AGGUCUGCAUUCAAAUCCCCAGA |
| hsa-miR-6504 | 2792 | CAUUACAGCACAGCCAUUCU | 2793 | UCUGGCUGUGCUGUAAUGCAG |
| hsa-miR-6505 | 2794 | UGACUUCUACCUCUUCCAAAG | 2795 | UUGGAAUAGGGGAUAUCUCAGC |
| hsa-miR-6506 | 2796 | ACUGGGAUGUCACUGAAUAUGGU | 2797 | UCGUAUCAGAGAUUCCAGACAC |
| hsa-miR-6507 | 2798 | CAAAGUCCUUCCUAUUUUUCCC | 2799 | GAAGAAUAGGAGGGACUUUGU |
| hsa-miR-6508 | 2800 | UCUAGAAAUGCAUGACCCACC | 2801 | UGGGCCAUGCAUUUCUAGAACU |
| hsa-miR-6509 | 2802 | AUUAGGUAGUGGCAGUGGAAC | 2803 | UUCCACUGCCACUACCUAAUUU |
| hsa-miR-651 | 2804 | UUUAGGAUAAGCUUGACUUUUG | 2805 | AAAGGAAAGUGUAUCCUAAAAG |
| hsa-miR-6510 | 2806 | CAGCAGGGGAGAGAGAGGAGUC | 2807 | CACCGACUCUGUCUCCUGCAG |
| hsa-miR-6511a | 2808 | CAGGCAGAAGUGGGGCUGACAGG | 2809 | CCUCACCAUCCCUUCUGCCUGC |
| hsa-miR-6511b | 2810 | CUGCAGGCAGAAGUGGGGCUGACA | 2811 | CCUCACCACCCCUUCUGCCUGCA |
| hsa-miR-6512 | 2812 | UACCAUUAGAAGAGCUGGAAGA | 2813 | UUCCAGCCCUUCUAAUGGUAGG |
| hsa-miR-6513 | 2814 | UUUGGGAUUGACGCCACAUGUCU | 2815 | UCAAGUGUCAUCUGUCCCUAG |
| hsa-miR-6514 | 2816 | CUGCCUGUUCUUCCACUCCAG | 2817 | UAUGGAGUGGACUUUCAGCUGGC |
| hsa-miR-6515 | 2818 | UCUCUUCAUCUACCCCCCAG | 2819 | UUGGAGGGUGUGGAAGCAUC |
| hsa-miR-6516 | 2820 | UUUGCAGUAACAGGUGUGAGCA | 2821 | AUCAUGUAUGAUACUGCAAACA |
| hsa-miR-652 | 2822 | AAUGGCGCCACUAGGGUUGUG | 2823 | CAACCCUAGGAGAGGGUGCCAUUCA |
| hsa-miR-653 | 2824 | GUGUUGAAACAAUCUCUACUG | 2825 | UUCACUGGAGUUUGUUUCAAUA |
| hsa-miR-654 | 2826 | UGGUGGGCCGCAGAACAUGUGC | 2827 | UAUGUCUGCUGACCAUCACCUU |
| hsa-miR-655 | 2828 | AGAGGUUAUCCGUGUUAUGUUC | 2829 | AUAAUACAUGGUUAACCUCUUU |
| hsa-miR-656 | 2830 | AGGUUGCCUGUGAGGUGUUCA | 2831 | AAUAUUAUACAGUCAACCUCU |
| hsa-miR-657 | 2832 | GGCAGGUUCUCACCCUCUCUAGG | 2833 | UAGAGAGGGUGAGAACCUGCCUU |
| hsa-miR-658 | 2834 | GGCGGAGGGAAGUAGGUCCGUUGGU | 2835 | CAACGGACCUACUUCCCUCCGCCUU |
| hsa-miR-659 | 2836 | AGGACCUUCCCUGAACCAAGGA | 2837 | CUUGGUUCAGGGAGGGUCCCCA |
| hsa-miR-660 | 2838 | ACCUCCUGUGUGCAUGGAUUA | 2839 | UACCCAUUGCAUAUCGGAGUUG |
| hsa-miR-661 | 2840 | UGCCUGGGUCUCUGGCCUGCGCGU | 2841 | GCGCAGGCCAGAGACCCAGGCAUU |
| hsa-miR-662 | 2842 | UCCCACGUUGUGGCCCAGCAG | 2843 | GCUGGGCCACAACGUGGGAUU |
| hsa-miR-663a | 2844 | AGGCGGGGCGCCGCGGGACCGC | 2845 | GGUCCCGCGGCGCCCGCCUUU |
| hsa-miR-663b | 2846 | GGUGGCCCGGCCGUGCCUGAGG | 2847 | UCAGGCACGGCCGGGCCACCUU |
| hsa-miR-664a | 2848 | ACUGGCUAGGGAAAAUGAUUGGAU | 2849 | UAUUCAUUUAUCCCCAGCCUACA |
| hsa-miR-664b | 2850 | UUCAUUUGCCUCCCAGCCUACA | 2851 | UGGGCUAAGGGAGAUGAUUGGGUA |
| hsa-miR-665 | 2852 | ACCAGGAGGCUGAGGCCCCU | 2853 | GGGCCUCAGCCUCCUGGUUU |
| hsa-miR-668 | 2854 | UGUCACUCGGCUCGGCCCACUAC | 2855 | UGCGCCUCGGGUGAGCAUG |
| hsa-miR-670 | 2856 | UUUCCUCAUAUUCAUUCAGGA | 2857 | GUCCCUGAGUGUAUGUGGUG |
| hsa-miR-671 | 2858 | UCCGGUUCUCAGGGCUCCACC | 2859 | AGGAAGCCCUGGAGGGGCUGGAG |

TABLE 1-continued miRNA Sequences

| miRNA | SEQ ID NO: | Sequence 1 | SEQ ID NO: | Sequence 2 |
|---|---|---|---|---|
| hsa-miR-6715a | 2860 | CCAAACCAGUCGUGCCUGUGG | 2861 | ACAGGCACGACUGGUUUGGUU |
| hsa-miR-6715b | 2862 | CUCAAACCGGCUGUGCCUGUGG | 2863 | ACAGGCACGACUGGUUUGGCA |
| hsa-miR-6716 | 2864 | UGGGAAUGGGGUAAGGGCC | 2865 | UCCGAACUCUCCAUUCCUCUGC |
| hsa-miR-6717 | 2866 | AGGCGAUGUGGGAUGUAGAGA | 2867 | UCUACAUCCCCACAUCGCCUUU |
| hsa-miR-6718 | 2868 | UAGUGGUCAGAGGGCUUAUGA | 2869 | AUAAGCCCUCUGACCACUAUU |
| hsa-miR-6719 | 2870 | UCUGACAUCAGUGAUUCUCCUG | 2871 | GGAGAAUCACUGAUGUCAGAUU |
| hsa-miR-6720 | 2872 | UUCCAGCCCUGGUAGGCGCCGCG | 2873 | CGCGCCUGCAGGAACUGGUAGA |
| hsa-miR-6721 | 2874 | UGGGCAGGGGCUUAUUGUAGGAG | 2875 | CCUACAAUAAGCCCCUGCCCAUU |
| hsa-miR-6722 | 2876 | UGCAGGGGUCGGGUGGGCCAGG | 2877 | AGGCGCACCCGACCACAUGC |
| hsa-miR-6723 | 2878 | AUAGUCCGAGUAACGUCGGGGC | 2879 | CCCGACGUUACUCGGACUAUUU |
| hsa-miR-6724 | 2880 | CUGGGCCCGCGGCGGGCGUGGGG | 2881 | CCACGCCCGCCGCGGGCCCAGUU |
| hsa-miR-6726 | 2882 | CGGGAGCUGGGGUCUGCAGGU | 2883 | CUCGCCCUGUCUCCCGCUAG |
| hsa-miR-6727 | 2884 | UCCUGCCACCUCCUCCGCAG | 2885 | CUCGGGGCAGGCGGCUGGGAGCG |
| hsa-miR-6728 | 2886 | UCUCUGCUCUGCUCUCCCAG | 2887 | UUGGGAUGGUAGGACCAGAGGGG |
| hsa-miR-6729 | 2888 | UCAUCCCCUCGCCCUCUCAG | 2889 | UGGGCGAGGGCGGCUGAGCGGC |
| hsa-miR-6730 | 2890 | AGAAAGGUGGAGGGGUUGUCAGA | 2891 | CCUGACACCCCAUCUGCCCUCA |
| hsa-miR-6731 | 2892 | UGGGAGAGCAGGGUAUUGUGGA | 2893 | UCUAUUCCCACUCUCCCCAG |
| hsa-miR-6732 | 2894 | UAGGGGUGGCAGGCUGGCC | 2895 | UAACCUGUCCUCUCCCUCCCAG |
| hsa-miR-6733 | 2896 | UCAGUGUCUGGAUUUCCUAG | 2897 | UGGGAAAGACAAACUCAGAGUU |
| hsa-miR-6734 | 2898 | CCCUUCCCUCACUCUUCUCUCAG | 2899 | UUGAGGGGAGAAUGAGGUGGAGA |
| hsa-miR-6735 | 2900 | AGGCCUGUGGCUCCUCCCUCAG | 2901 | CAGGGCAGAGGGCACAGGAAUCUGA |
| hsa-miR-6736 | 2902 | UCAGCUCCUCUCUACCCACAG | 2903 | CUGGGUGAGGGCAUCUGUGGU |
| hsa-miR-6737 | 2904 | UUGGGGUGGUCGGCCCUGGAG | 2905 | UCUGUGCUUCACCCCUACCCAG |
| hsa-miR-6738 | 2906 | CUUCUGCCUGCAUUCUACUCCCAG | 2907 | CGAGGGGUAGAAGAGCACAGGGG |
| hsa-miR-6739 | 2908 | AUUGUUCUGUCUUUCUCCCAG | 2909 | UGGGAAAGAGAAAGAACAAGUA |
| hsa-miR-6740 | 2910 | UGUCUUCUCUCCUCCCAAACAG | 2911 | AGUUUGGGAUGGAGAGAGGAGA |
| hsa-miR-6741 | 2912 | UCGGCUCUCUCCCUCACCCUAG | 2913 | GUGGGUGCUGGUGGGAGCCGUG |
| hsa-miR-6742 | 2914 | AGUGGGUGGGACCCAGCUGUU | 2915 | ACCUGGGUUGUCCCCUCUAG |
| hsa-miR-6743 | 2916 | AAGGGCAGGGACGGGUGGCCC | 2917 | AGCCGCUCUUCUCCCUGCCCACA |
| hsa-miR-6744 | 2918 | GGGCCUCUCUUGUCAUCCUGCAG | 2919 | UGGAUGACAGUGGAGGCCU |
| hsa-miR-6745 | 2920 | UGGGUGGAAGAAGGUCUGGUU | 2921 | CCAGACCUUCUUCCACCCAUU |
| hsa-miR-6746 | 2922 | CCGGGAGAAGGAGGUGGCCUGG | 2923 | CAGCCGCCGCCUGUCUCCACAG |
| hsa-miR-6747 | 2924 | UCCUGCCUUCCUCUGCACCAG | 2925 | AGGGGUGUGGAAAGAGGCAGAACA |
| hsa-miR-6748 | 2926 | UCCUGUCCCUGUCUCCUACAG | 2927 | UGUGGGUGGGAAGGACUGGAUU |
| hsa-miR-6749 | 2928 | UCGGCCUGGGGUUGGGGAGC | 2929 | CUCCUCCCCUGCCUGGCCCAG |
| hsa-miR-675 | 2930 | UGGUGCGGAGAGGGCCCACAGUG | 2931 | CUGUAUGCCCUCACCGCUCA |
| hsa-miR-6750 | 2932 | CAGGGAACAGCUGGGGUGAGCUGCU | 2933 | GAACUCACCCUCUGCUCCCAG |
| hsa-miR-6751 | 2934 | UUGGGGGUGAGGUUGGUGUCUGG | 2935 | ACUGAGCCUCUCUCUCUCCAG |

TABLE 1-continued miRNA Sequences

| miRNA | SEQ ID NO: | Sequence 1 | SEQ ID NO: | Sequence 2 |
|---|---|---|---|---|
| hsa-miR-6752 | 2936 | UCCCUGCCCCCAUACUCCCAG | 2937 | GGGGGGUGUGGAGCCAGGGGGC |
| hsa-miR-6753 | 2938 | UGGUCUGUCUCUGCCCUGGCAC | 2939 | CACCAGGGCAGAGCAGGGCUGA |
| hsa-miR-6754 | 2940 | UCUUCACCUGCCUCUGCCUGCA | 2941 | CCAGGGAGGCUGGUUUGGAGGA |
| hsa-miR-6755 | 2942 | UGUUGUCAUGUUUUUUCCCUAG | 2943 | UAGGGUAGACACUGACAACGUU |
| hsa-miR-6756 | 2944 | UCCCCUUCCUCCCUGCCCAG | 2945 | AGGGUGGGCUGGAGGUGGGGCU |
| hsa-miR-6757 | 2946 | UAGGGAUGGGAGGCCAGGAUGA | 2947 | AACACUGGCCUUGCUAUCCCCA |
| hsa-miR-6758 | 2948 | ACUCAUUCUCCUCUGUCCAG | 2949 | UAGAGAGGGGAAGGAUGUGAUGU |
| hsa-miR-6759 | 2950 | UUGUGGGUGGGCAGAAGUCUGU | 2951 | UGACCUUUGCCUCUCCCCUCAG |
| hsa-miR-676 | 2952 | CUGUCCUAAGGUUGUUGAGUU | 2953 | UCUUCAACCUCAGGACUUGCA |
| hsa-miR-6760 | 2954 | CAGGGAGAAGGUGGAAGUGCAGA | 2955 | ACACUGUCCCCUUCUCCCCAG |
| hsa-miR-6761 | 2956 | UCUGAGAGAGCUCGAUGGCAG | 2957 | UCCUACGCUGCUCUCUCACUCC |
| hsa-miR-6762 | 2958 | CGGGGCCAUGGAGCAGCCUGUGU | 2959 | UGGCUGCUUCCCUUGGUCUCCAG |
| hsa-miR-6763 | 2960 | CUGGGGAGUGGCUGGGGAG | 2961 | CUCCCCGCCUCUGCCCCCAG |
| hsa-miR-6764 | 2962 | UCUCUGGUCUUUCCUUGACAG | 2963 | UCCCAGGGUCUGGUCAGAGUUG |
| hsa-miR-6765 | 2964 | UCACCUGGCUGGCCCGCCCAG | 2965 | GUGAGGCGGGGCCAGGAGGGUGUGU |
| hsa-miR-6766 | 2966 | CGGGUGGGAGCAGAUCUUAUUGAG | 2967 | UGAUUGUCUUCCCCCACCCUCA |
| hsa-miR-6767 | 2968 | UCGCAGACAGGGACACAUGGAGA | 2969 | CCACGUGCUUCUCUUUCCGCAG |
| hsa-miR-6768 | 2970 | CAAAGGCCACAUUCUCCUGUGCAC | 2971 | CACACAGGAAAAGCGGGGCCCUG |
| hsa-miR-6769a | 2972 | GAGCCCCUCUCUGCUCUCCAG | 2973 | AGGUGGGUAUGGAGGAGCCCU |
| hsa-miR-6769b | 2974 | UGGUGGGUGGGGAGGAGAAGUGC | 2975 | CCCUCUCUGUCCCACCCAUAG |
| hsa-miR-6770 | 2976 | UGAGAAGGCACAGCUUGCACGUGA | 2977 | CUGGCGGCUGUGUCUUCACAG |
| hsa-miR-6771 | 2978 | CUCGGGAGGGCAUGGGCCAGGC | 2979 | CAAACCCCUGUCUACCCGCAG |
| hsa-miR-6772 | 2980 | UGGGUGUAGGCUGGAGCUGAGG | 2981 | UUGCUCCUGACUCUGUGCCCACA |
| hsa-miR-6773 | 2982 | ACUGUCACUUCUCUGCCCAUAG | 2983 | UUGGGCCCAGGAGUAAACAGGAU |
| hsa-miR-6774 | 2984 | ACUUGGGCAGGAGGGACCCUGUAUG | 2985 | UCGUGUCCCUCUUGUCCACAG |
| hsa-miR-6775 | 2986 | AGGCCCUGUCCUCUGCCCCAG | 2987 | UCGGGCAUGGGGAGGGAGGCUGG |
| hsa-miR-6776 | 2988 | UCUGGGUGCAGUGGGGGUU | 2989 | CAACCACCACUGUCUCUCCCCAG |
| hsa-miR-6777 | 2990 | UCCACUCUCCUGGCCCCCAG | 2991 | ACGGGGAGUCAGGCAGUGGUGGA |
| hsa-miR-6778 | 2992 | UGCCUCCCUGACAUUCCACAG | 2993 | AGUGGGAGGACAGGAGGCAGGU |
| hsa-miR-6779 | 2994 | AAGCCCUGUCUCCUCCCAUCU | 2995 | CUGGGAGGGCUGGGUUUGGC |
| hsa-miR-6780a | 2996 | CUCCUCUGUUUUCUUUCCUAG | 2997 | UUGGGAGGGAAGACAGCUGGAGA |
| hsa-miR-6780b | 2998 | UCCCUUGUCUCCUUUCCCUAG | 2999 | UGGGGAAGGCUUGGCAGGGAAGA |
| hsa-miR-6781 | 3000 | CGGGCCGGAGGUCAAGGGCGU | 3001 | UGCCUCUUUUCCACGGCCUCAG |
| hsa-miR-6782 | 3002 | UAGGGUGGGGGAAUUCAGGGGUGU | 3003 | CACCUUUGUGUCCCCAUCCUGCA |
| hsa-miR-6783 | 3004 | UUCCUGGGCUUCUCCUCUGUAG | 3005 | UAGGGGAAAAGUCCUGAUCCGG |
| hsa-miR-6784 | 3006 | UCUCACCCCAACUCUGCCCCAG | 3007 | GCCGGGGCUUUGGGUGAGGG |
| hsa-miR-6785 | 3008 | ACAUCGCCCCACCUUCCCCAG | 3009 | UGGGAGGGCGUGGAUGAUGGUG |

TABLE 1-continued miRNA Sequences

| miRNA | SEQ ID NO: | Sequence 1 | SEQ ID NO: | Sequence 2 |
|---|---|---|---|---|
| hsa-miR-6786 | 3010 | UGACGCCCCUUCUGAUUCUGCCU | 3011 | GCGGUGGGGCCGGAGGGGCGU |
| hsa-miR-6787 | 3012 | UCUCAGCUGCUGCCCUCUCCAG | 3013 | UGGCGGGGGUAGAGCUGGCUGC |
| hsa-miR-6788 | 3014 | CUGGGAGAAGAGUGGUGAAGA | 3015 | UUCGCCACUUCCCUCCCUGCAG |
| hsa-miR-6789 | 3016 | CGGCGCCCGUGUCUCCUCCAG | 3017 | GUAGGGGCGUCCCGGGCGCGGG |
| hsa-miR-6790 | 3018 | GUGAGUGUGGAUUUGGCGGGGUU | 3019 | CGACCUCGGCGACCCCUCACU |
| hsa-miR-6791 | 3020 | CCCCUGGGGCUGGGCAGGCGGA | 3021 | UGCCUCCUUGGUCUCCGGCAG |
| hsa-miR-6792 | 3022 | CUCCUCCACAGCCCCUGCUCAU | 3023 | GUAAGCAGGGGCUCUGGGUGA |
| hsa-miR-6793 | 3024 | UGUGGGUUCUGGGUUGGGGUGA | 3025 | UCCCCAACCCCUGCCCGCAG |
| hsa-miR-6794 | 3026 | CAGGGGGACUGGGGGUGAGC | 3027 | CUCACUCUCAGUCCCUCCCU |
| hsa-miR-6795 | 3028 | UGGGGGGACAGGAUGAGAGGCUGU | 3029 | ACCCCUCGUUUCUUCCCCCAG |
| hsa-miR-6796 | 3030 | GAAGCUCUCCCCUCCCCGCAG | 3031 | UUGUGGGGUUGGAGAGCUGGCUG |
| hsa-miR-6797 | 3032 | UGCAUGACCCUUCCCUCCCCAC | 3033 | AGGAGGGAAGGGGCUGAGAACAGGA |
| hsa-miR-6798 | 3034 | CCAGGGGGAUGGGCGAGCUUGGG | 3035 | CUACCCCCCAUCCCCCUGUAG |
| hsa-miR-6799 | 3036 | GGGGAGGUGUGCAGGGCUGG | 3037 | UGCCCUGCAUGGUGUCCCCACAG |
| hsa-miR-6800 | 3038 | GUAGGUGACAGUCAGGGGCGG | 3039 | CACCUCUCCUGGCAUCGCCCC |
| hsa-miR-6801 | 3040 | UGGUCAGAGGCAGCAGGAAAUGA | 3041 | ACCCCUGCCACUCACUGGCC |
| hsa-miR-6802 | 3042 | UUCACCCCUCUCACCUAAGCAG | 3043 | CUAGGUGGGGGCUUGAAGC |
| hsa-miR-6803 | 3044 | UCCCUCGCCUUCUCACCCUCAG | 3045 | CUGGGGGUGGGGGCUGGGCGU |
| hsa-miR-6804 | 3046 | UGAGGGUGUCAGCAGGUGACG | 3047 | CGCACCUGCCUCUCACCCACAG |
| hsa-miR-6805 | 3048 | UUGCUCUGCUCCCCCGCCCCAG | 3049 | UAGGGGGCGGCUUGUGGAGUGU |
| hsa-miR-6806 | 3050 | UGAAGCUCUGACAUUCCUGCAG | 3051 | UGUAGGCAUGAGGCAGGGCCCAGG |
| hsa-miR-6807 | 3052 | GUGAGCCAGUGGAAUGGAGAGG | 3053 | CACUGCAUUCCUGCUUGGCCAG |
| hsa-miR-6808 | 3054 | CAGGCAGGGAGGUGGGACCAUG | 3055 | GUGUGACCACCGUUCCUGCAG |
| hsa-miR-6809 | 3056 | CUUCUCUUCUCUCCUUCCCAG | 3057 | UGGCAAGGAAAGAAGAGGAUCA |
| hsa-miR-6810 | 3058 | AUGGGGACAGGGAUCAGCAUGGC | 3059 | UCCCCUGCUCCCUUGUUCCCAG |
| hsa-miR-6811 | 3060 | AGCCUGUGCUUGUCCCUGCAG | 3061 | AUGCAGGCCUGUGUACAGCACU |
| hsa-miR-6812 | 3062 | AUGGGGUGAGAUGGGGAGGAGCAGC | 3063 | CCGCUCUUCCCCUGACCCCAG |
| hsa-miR-6813 | 3064 | CAGGGGCUGGGGUUUCAGGUUCU | 3065 | AACCUUGGCCCCUCUCCCCAG |
| hsa-miR-6814 | 3066 | ACUCGCAUCCUUCCCUUGGCAG | 3067 | UCCCAAGGGUGAGAUGCUGCCA |
| hsa-miR-6815 | 3068 | UAGGUGGCGCCGGAGGAGUCAUU | 3069 | UGGCUUCUCUUGCACACCCAG |
| hsa-miR-6816 | 3070 | UGGGGCGGGGCAGGUCCCUGC | 3071 | GAAGGACCUGCACCUUCG |
| hsa-miR-6817 | 3072 | UCUGCCAUAGGAAGCUUGGAGUGG | 3073 | UCUCUCUGACUCCAUGGCA |
| hsa-miR-6818 | 3074 | UUGUGUGAGUACAGAGAGCAUC | 3075 | UUGUCUCUUGUUCCUCACACAG |
| hsa-miR-6819 | 3076 | UUGGGGUGGAGGGCCAAGGAGC | 3077 | AAGCCUCUGUCCCCACCCCAG |
| hsa-miR-6820 | 3078 | UGCGGCAGAGCUGGGGUCA | 3079 | UGUGACUUCUCCCCUGCCACAG |
| hsa-miR-6821 | 3080 | GUGCGUGGUGGCUCGAGGCGGGG | 3081 | UGACCUCUCCGCUCCGCACAG |
| hsa-miR-6822 | 3082 | AGGCUCUAACUGGCUUUCCCUGCA | 3083 | CAGGGAACCAGUUGGGGCUU |
| hsa-miR-6823 | 3084 | UCAGGGUUGGUAGGGGUUGCU | 3085 | UGAGCCUCUCCUUCCCUCCAG |

TABLE 1-continued miRNA Sequences

| miRNA | SEQ ID NO: | Sequence 1 | SEQ ID NO: | Sequence 2 |
|---|---|---|---|---|
| hsa-miR-6824 | 3086 | GUAGGGGAGGUUGGGCCAGGGA | 3087 | UCUCUGGUCUUGCCACCCCAG |
| hsa-miR-6825 | 3088 | GCGCUGACCCGCCUUCUCCGCA | 3089 | UGGGGAGGUGUGGAGUCAGCAU |
| hsa-miR-6826 | 3090 | CUCCCCUCUCUUUCCUGUUCAG | 3091 | UCAAUAGGAAAGAGGUGGGACCU |
| hsa-miR-6827 | 3092 | UGGGAGCCAUGAGGGUCUGUGC | 3093 | ACCGUCUCUUCUGUUCCCCAG |
| hsa-miR-6828 | 3094 | AUCUGCUCUCUUGUUCCCAG | 3095 | AGGAAGCAAGAGAACCCUGUGG |
| hsa-miR-6829 | 3096 | UGGGCUGCUGAGAAGGGGCA | 3097 | UGCCUCCUCCGUGGCCUCAG |
| hsa-miR-6830 | 3098 | CCAAGGAAGGAGGCUGGACAUC | 3099 | UGUCUUUCUUCUCUCCCUUGCAG |
| hsa-miR-6831 | 3100 | UAGGUAGAGUGUGAGGAGGAGGUC | 3101 | UGACUAACUCCCACUCUACAG |
| hsa-miR-6832 | 3102 | AGUAGAGAGGAAAAGUUAGGGUC | 3103 | ACCCUUUUCUCUUUCCCAG |
| hsa-miR-6833 | 3104 | UUUCUCUCUCCACUUCCUCAG | 3105 | GUGUGGAAGAUGGGAGGAGAAA |
| hsa-miR-6834 | 3106 | GUGAGGGACUGGGAUUUGUGG | 3107 | UAUGUCCCAUCCCUCCAUCA |
| hsa-miR-6835 | 3108 | AGGGGGUAGAAAGUGGCUGAAG | 3109 | AAAAGCACUUUUCUGUCUCCCAG |
| hsa-miR-6836 | 3110 | AUGCCUCCCCGGCCCCGCAG | 3111 | CGCAGGGCCCUGGCGCAGGCAU |
| hsa-miR-6837 | 3112 | ACCAGGGCCAGCAGGGAAUGU | 3113 | CCUUCACUGUGACUCUGCUGCAG |
| hsa-miR-6838 | 3114 | AAGCAGCAGUGGCAAGACUCCU | 3115 | AAGUCCGCUUCUGUUGCAG |
| hsa-miR-6839 | 3116 | UCUGGAUUGAAGAGACGACCCA | 3117 | UUGGGUUUUCUCUUCAAUCCAG |
| hsa-miR-6840 | 3118 | ACCCCCGGGCAAAGACCUGCAGAU | 3119 | GCCCAGGACUUUGUGCGGGGUG |
| hsa-miR-6841 | 3120 | UAGGGUACUCAGAGCAAGUUGU | 3121 | ACCUUGCAUCUGCAUCCCCAG |
| hsa-miR-6842 | 3122 | UGGGGGUGGUCUCUAGCCAAGG | 3123 | UUGGCUGGUCUCUGCUCCGCAG |
| hsa-miR-6843 | 3124 | AUGGUCUCCUGUUCUCUGCAG | 3125 | GCAGAGAACAGGAGACCAUUU |
| hsa-miR-6844 | 3126 | UUCUUUGUUUUUAAUUCACAG | 3127 | GUGAAUUAAAAACAAAGAAUU |
| hsa-miR-6845 | 3128 | CGGGGCCAGAGCAGAGAGC | 3129 | CCUCUCCUCCCUGUGCCCAG |
| hsa-miR-6846 | 3130 | UGACCCCUUCUGUCUCCCUAG | 3131 | UGGGGGCUGGAUGGGGUAGAGU |
| hsa-miR-6847 | 3132 | GGCUCAUGUGUCUGUCCUCUUC | 3133 | ACAGAGGACAGUGGAGUGUGAGC |
| hsa-miR-6848 | 3134 | UGGGGCUGGGAUGGGCCAUGGU | 3135 | GUGGUCUCUUGGCCCCCAG |
| hsa-miR-6849 | 3136 | ACCAGCCUGUGUCCACCUCCAG | 3137 | GAGUGGAUAGGGGAGUGUGUGGA |
| hsa-miR-6850 | 3138 | CCCGGCCGGAACGCCGCACU | 3139 | GUGCGGAACGCUGGCCGGGGCG |
| hsa-miR-6851 | 3140 | AGGAGGUGGUACUAGGGGCCAGC | 3141 | UGGCCCUUUGUACCCCUCCAG |
| hsa-miR-6852 | 3142 | CCCUGGGGUUCUGAGGACAUG | 3143 | UGUCCUCUGUUCCUCAG |
| hsa-miR-6853 | 3144 | AGCGUGGGAUGUCCAUGAAGUCAG | 3145 | UGUUCAUUGGAACCCUGCGCAG |
| hsa-miR-6854 | 3146 | UGCGUUUCUCCUCUUGAGCAG | 3147 | AAGCUCAGGUUUGAGAACUGCUGA |
| hsa-miR-6855 | 3148 | AGACUGACCUUCAACCCCACAG | 3149 | UUGGGGUUUGGGGUGCAGACAUUGC |
| hsa-miR-6856 | 3150 | UACAGCCCUGUGAUCUUUCCAG | 3151 | AAGAGAGGAGCAGUGGUGCUGUGG |
| hsa-miR-6857 | 3152 | UGACUGAGCUUCUCCCCACAG | 3153 | UUGGGGAUUGGGUCAGGCCAGU |
| hsa-miR-6858 | 3154 | CAGCCAGCCCUGCUCACCCCU | 3155 | GUGAGGAGGGGCUGGCAGGGAC |
| hsa-miR-6859 | 3156 | UGACCCCAUGUCGCCUCUGUAG | 3157 | GAGAGGAACAUGGGCUCAGGACA |
| hsa-miR-6860 | 3158 | ACUGGGCAGGGCUGUGGUGAGU | 3159 | UCACCACAGCCCUGCCCAGUUU |

TABLE 1-continued miRNA Sequences

| miRNA | SEQ ID NO: | Sequence 1 | SEQ ID NO: | Sequence 2 |
|---|---|---|---|---|
| hsa-miR-6861 | 3160 | ACUGGGUAGGUGGGGCUCCAGG | 3161 | UGGACCUCUCCUCCCCAG |
| hsa-miR-6862 | 3162 | CCUCACCCAGCUCUCUGGCCCUCU | 3163 | CGGGCAUGCUGGGAGAGACUUU |
| hsa-miR-6863 | 3164 | UAGACGUGGUGAAGGAUUGAGUG | 3165 | CUCAAUCCUUCACCACGUCUAUU |
| hsa-miR-6864 | 3166 | UUGAAGGGACAAGUCAGAUAUGCC | 3167 | GUGAGACUUCUCUCCCUUCAG |
| hsa-miR-6865 | 3168 | ACACCCUCUUUCCCUACCGCC | 3169 | UAGGUGGCAGAGGAGGGACUUCA |
| hsa-miR-6866 | 3170 | GAUCCCUUUAUCUGUCCUCUAG | 3171 | UUAGAGGCUGGAAUAGAGAUUCU |
| hsa-miR-6867 | 3172 | UGUGUGUGUAGAGGAAGAAGGGA | 3173 | CUCUCCCUCUUUACCCACUAG |
| hsa-miR-6868 | 3174 | ACUGGCAGAACACUGAAGCAGC | 3175 | UUCCUUCUGUUGUCUGUGCAG |
| hsa-miR-6869 | 3176 | GUGAGUAGUGGCGCGCGGCGGC | 3177 | CGCCGCGCGCAUCGGCUCAGC |
| hsa-miR-6870 | 3178 | UGGGGGAGAUGGGGGUUGA | 3179 | GCUCAUCCCCAUCUCCUUUCAG |
| hsa-miR-6871 | 3180 | CAUGGGAGUUCGGGGUGGUUGC | 3181 | CAGCACCCUGUGGCUCCCACAG |
| hsa-miR-6872 | 3182 | CCCAUGCCUCCUGCCGCGGUC | 3183 | UCUCGCAUCAGGAGGCAAGG |
| hsa-miR-6873 | 3184 | UUCUCUCUGUCUUUCUCUCUCAG | 3185 | CAGAGGGAAUACAGAGGGCAAU |
| hsa-miR-6874 | 3186 | AUGGAGCUGGAACCAGAUCAGGC | 3187 | CAGUUCUGCUGUUCUGACUCUAG |
| hsa-miR-6875 | 3188 | UGAGGGACCCAGGACAGGAGA | 3189 | AUUCUUCCUGCCCUGGCUCCAU |
| hsa-miR-6876 | 3190 | AGCUGUCUGUGUUUUCCUUCUCAG | 3191 | CAGGAAGGAGACAGGCAGUUCA |
| hsa-miR-6877 | 3192 | CAGCCUCUGCCCUUGGCCUCC | 3193 | AGGGCCGAAGGGUGGAAGCUGC |
| hsa-miR-6878 | 3194 | CUGGCCUCUUCUUUCUCCUAG | 3195 | AGGGAGAAAGCUAGAAGCUGAAG |
| hsa-miR-6879 | 3196 | UGUCACCCGCUCCUUGCCCAG | 3197 | CAGGGCAGGGAAGGUGGGAGAG |
| hsa-miR-6880 | 3198 | UGGUGGAGGAAGAGGGCAGCUC | 3199 | CCGCCUUCUCUCCUCCCCAG |
| hsa-miR-6881 | 3200 | AUCCUCUUUCGUCCUUCCCACU | 3201 | UGGGGUAAGGAUAGGAGGGUCA |
| hsa-miR-6882 | 3202 | UGCUGCCUCUCCUCUUGCCUGCAG | 3203 | UACAAGUCAGGAGCUGAAGCAG |
| hsa-miR-6883 | 3204 | UUCCCUAUCUCACUCUCCUCAG | 3205 | AGGGAGGGUGUGGUAUGGAUGU |
| hsa-miR-6884 | 3206 | CCCAUCACCUUUCCGUCUCCCU | 3207 | AGAGGCUGAGAAGGUGAUGUUG |
| hsa-miR-6885 | 3208 | AGGGGGGCACUGCGCAAGCAAAGCC | 3209 | CUUUGCUUCCUGCUCCCCUAG |
| hsa-miR-6886 | 3210 | UGCCCUUCUCUCCUCCUGCCU | 3211 | CCCGCAGGUGAGAUGAGGGCU |
| hsa-miR-6887 | 3212 | UCCCCUCCACUUUCCUCCUAG | 3213 | UGGGGGGACAGAUGGAGAGGACA |
| hsa-miR-6888 | 3214 | AAGGAGAUGCUCAGGCAGAU | 3215 | AUCUGUCUCGAUUGUUUCCAG |
| hsa-miR-6889 | 3216 | UCGGGGAGUCUGGGGUCCGGAAU | 3217 | UCUGUGCCCCUACUUCCCAG |
| hsa-miR-6890 | 3218 | CCACUGCCUAUGCCCCACAG | 3219 | CAUGGGGUAGGGCAGAGUAGG |
| hsa-miR-6891 | 3220 | CCCUCAUCUUCCCCUCCUUUC | 3221 | UAAGGAGGGGAUGAGGGG |
| hsa-miR-6892 | 3222 | GUAAGGGACCGGAGAGUAGGA | 3223 | UCCCUCUCCCACCCCUUGCAG |
| hsa-miR-6893 | 3224 | CCCUGCUGCCUUCACCUGCCAG | 3225 | CAGGCAGGUGUAGGGUGGAGC |
| hsa-miR-6894 | 3226 | UUGCCUGCCCUCUUCCUCCAG | 3227 | AGGAGGAUGGAGAGCUGGGCCAGA |
| hsa-miR-6895 | 3228 | CAGGGCCAGGCACAGAGUAAG | 3229 | UGUCUCUCGCCCUUGGCCUUAG |
| hsa-miR-7-1 | 3230 | UGGAAGACUAGUGAUUUUGUUGU | 3231 | CAACAAAUCACAGUCUGCCAUA |
| hsa-miR-7-2 | 3232 | UGGAAGACUAGUGAUUUUGUUGU | 3233 | CAACAAAUCCCAGUCUACCUAA |
| hsa-miR-708 | 3234 | CAACUAGACUGUGAGCUUCUAG | 3235 | AAGGAGCUUACAAUCUAGCUGGG |

TABLE 1-continued miRNA Sequences

| miRNA | SEQ ID NO: | Sequence 1 | SEQ ID NO: | Sequence 2 |
|---|---|---|---|---|
| hsa-miR-7106 | 3236 | UGGGAGGAGGGGAUCUUGGG | 3237 | AGCUCCCUGAAUCCCUGUCCCAG |
| hsa-miR-7107 | 3238 | UCGGCCUGGGGAGGAGGAAGGG | 3239 | UGGUCUGUUCAUUCUCUCUUUUUGGCC |
| hsa-miR-7108 | 3240 | GUGUGGCCGGCAGGCGGGUGG | 3241 | ACCCGCCCGUCUCCCCACAG |
| hsa-miR-7109 | 3242 | CAAGCCUCUCCUGCCCUUCCAG | 3243 | CUGGGGGGAGGAGACCCUGCU |
| hsa-miR-711 | 3244 | GGGACCCAGGGAGAGACGUAAG | 3245 | UACGUCUCUCCCUGGGUCCCUU |
| hsa-miR-7110 | 3246 | UCUCUCUCCCACUUCCCUGCAG | 3247 | UGGGGGUGUGGGGAGAGAGAG |
| hsa-miR-7111 | 3248 | AUCCUCUCUUCCCUCCUCCCAG | 3249 | UGGGGGAGGAAGGACAGGCCAU |
| hsa-miR-7112 | 3250 | UGCAUCACAGCCUUUGGCCCUAG | 3251 | ACGGGCAGGGCAGUGCACCCUG |
| hsa-miR-7113 | 3252 | UCCAGGGAGACAGUGUGUGAG | 3253 | CCUCCCUGCCCGCCUCUCUGCAG |
| hsa-miR-7114 | 3254 | UGACCCACCCCUCUCCACCAG | 3255 | UCUGUGGAGUGGGGUGCCUGU |
| hsa-miR-7150 | 3256 | CUGGCAGGGGAGAGGUA | 3257 | CCUCUCCCCUGCCAGUU |
| hsa-miR-7151 | 3258 | GAUCCAUCUCUGCCUGUAUUGGC | 3259 | CUACAGGCUGGAAUGGGCUCA |
| hsa-miR-7152 | 3260 | UCUGGUCCUGGACAGGAGGC | 3261 | UUUCCUGUCCUCCAACCAGACC |
| hsa-miR-7153 | 3262 | CACCAUGGACGGUUUACC | 3263 | UGAGAACUGACAAAUGUGGUAGG |
| hsa-miR-7154 | 3264 | UUCAUGAACUGGGUCUAGCUUGG | 3265 | AGGAGGACAAGUUGUGGGAU |
| hsa-miR-7155 | 3266 | UGGCCCAAGACCUCAGACC | 3267 | UCUGGGGUCUUGGGCCAUC |
| hsa-miR-7156 | 3268 | CUGCAGCCACUUGGGGAACUGGU | 3269 | UUGUUCUCAAACUGGCUGUCAGA |
| hsa-miR-7157 | 3270 | UCUGUGCUACUGGAUGAAGAGU | 3271 | UCAGCAUUCAUUGGCACCAGAGA |
| hsa-miR-7158 | 3272 | GGCUCAAUCUCUGGUCCUGCAGCC | 3273 | CUGAACUAGAGAUUGGGCCCA |
| hsa-miR-7159 | 3274 | UUUCUAUGUUAGUUGGAAG | 3275 | UUCAACAAGGGUGUAGGAUGG |
| hsa-miR-7160 | 3276 | CAGGGCCCUGGCUUUAGCAGA | 3277 | UGCUGAGGUCCGGGCUGUGCC |
| hsa-miR-7161 | 3278 | UAAAGACUGUAGAGGCAACUGGU | 3279 | UAGAUCUUUGACUCUGGCAGUCUCCAGG |
| hsa-miR-7162 | 3280 | UCUGAGGUGGAACAGCAGC | 3281 | UGCUUCCUUUCUCAGCUG |
| hsa-miR-718 | 3282 | CUUCCGCCCCGCCGGGCGUCG | 3283 | ACGCCCGGCGGGGCGGAAGUU |
| hsa-miR-744 | 3284 | UGCGGGGCUAGGGCUAACAGCA | 3285 | CUGUUGCCACUAACCUCAACCU |
| hsa-miR-7515 | 3286 | AGAAGGGAAGAUGGUGAC | 3287 | CACCAUCUUCCCUUCUUU |
| hsa-miR-758 | 3288 | UUUGUGACCUGGUCCACUAACC | 3289 | GAUGGUUGACCAGAGAGCACAC |
| hsa-miR-759 | 3290 | GCAGAGUGCAAACAAUUUUGAC | 3291 | CAAAAUUGUUUGCACUCUGCUU |
| hsa-miR-760 | 3292 | CGGCUCUGGGUCUGUGGGGA | 3293 | CCCACAGACCCAGAGCCGUU |
| hsa-miR-761 | 3294 | GCAGCAGGGUGAAACUGACACA | 3295 | UGUCAGUUUCACCCUGCUGCUU |
| hsa-miR-762 | 3296 | GGGGCUGGGGCCGGGGCCGAGC | 3297 | UCGGCCCCGGCCCCAGCCCCUU |
| hsa-miR-764 | 3298 | GCAGGUGCUCACUUGUCCUCCU | 3299 | GAGGACAAGUGAGCACCUGCUU |
| hsa-miR-7641 | 3300 | UUGAUCUCGGAAGCUAAGC | 3301 | UUAGCUUCCGAGAUCAAUU |
| hsa-miR-765 | 3302 | UGGAGGAGAAGGAAGGUGAUG | 3303 | UCACCUUCCUUCUCCUCCAUU |
| hsa-miR-766 | 3304 | AGGAGGAAUUGGUGCUGGUCUU | 3305 | ACUCCAGCCCCACAGCCUCAGC |
| hsa-miR-767 | 3306 | UGCACCAUGGUUGUCUGAGCAUG | 3307 | UCUGCUCAUACCCCAUGGUUUCU |
| hsa-miR-769 | 3308 | CUGGGAUCUCCGGGGUCUUGGUU | 3309 | UGAGACCUCUGGGUUCUGAGCU |

TABLE 1-continued miRNA Sequences

| miRNA | SEQ ID NO: | Sequence 1 | SEQ ID NO: | Sequence 2 |
|---|---|---|---|---|
| hsa-miR-770 | 3310 | UCCAGUACCACGUGUCAGGGCCA | 3311 | GCCCUGACACGUGGUACUGGAUU |
| hsa-miR-7702 | 3312 | CUUAGACUGCCAGACUCCCUGA | 3313 | AGGGAGUCUGGCAGUCUAAGUU |
| hsa-miR-7703 | 3314 | UUGCACUCUGGCCUUCUCCCAGG | 3315 | UGGGAGAAGGCCAGAGUGCAAUU |
| hsa-miR-7704 | 3316 | CGGGGUCGGCGGCGACGUG | 3317 | CGUCGCCGCCGACCCCGUU |
| hsa-miR-7705 | 3318 | AAUAGCUCAGAAUGUCAGUUCUG | 3319 | GAACUGACAUUCUGAGCUAUUUU |
| hsa-miR-7706 | 3320 | UGAAGCGCCUGUGCUCUGCCGAGA | 3321 | UCGGCAGAGCACAGGCGCUUCAUU |
| hsa-miR-7843 | 3322 | AUGAAGCCUUCUCUGCCUUACG | 3323 | GAGGGCAGAGCCAGCUUCCUGA |
| hsa-miR-7844 | 3324 | AAAACUAGGACUGUGUGGUGUA | 3325 | CACCACACAGUCCUAGUUUUUU |
| hsa-miR-7845 | 3326 | AAGGGACAGGGAGGGUCUGG | 3327 | ACGACCCUCCCUGUCCCUUUU |
| hsa-miR-7846 | 3328 | CAGCGGAGCCUGGAGAGAAGG | 3329 | UUCUCUCCAGGCUCCGCUGUU |
| hsa-miR-7847 | 3330 | CGUGGAGGACGAGGAGGAGGC | 3331 | CUCCUCCUCGUCCUCCACGUU |
| hsa-miR-7848 | 3332 | CUACCCUCGGUCUGCUUACCACA | 3333 | UGGUAAGCAGACCGAGGGUAGUU |
| hsa-miR-7849 | 3334 | GACAAUUGUUGAUCUUGGGCCU | 3335 | GCCCAAGAUCAACAAUUGUCUU |
| hsa-miR-7850 | 3336 | GUUUGGACAUAGUGUGGCUGG | 3337 | AGCCACACUAUGUCCAAACUU |
| hsa-miR-7851 | 3338 | UACCUGGGAGACUGAGGUUGGA | 3339 | CAACCUCAGUCUCCCAGGUAUU |
| hsa-miR-7852 | 3340 | UAUGUAGUAGUCAAAGGCAUUU | 3341 | AUGCCUUUGACUACUACAUAUU |
| hsa-miR-7853 | 3342 | UCAAAUGCAGAUCCUGACUUC | 3343 | AGUCAGGAUCUGCAUUUGAUU |
| hsa-miR-7854 | 3344 | UGAGGUGACCGCAGAUGGGAA | 3345 | CCCAUCUGCGGUCACCUCAUU |
| hsa-miR-7855 | 3346 | UUGGUGAGGACCCCAAGCUCGG | 3347 | GAGCUUGGGGUCCUCACCAAUU |
| hsa-miR-7856 | 3348 | UUUUAAGGACACUGAGGGAUC | 3349 | UCCCUCAGUGUCCUUAAAAUU |
| hsa-miR-7973 | 3350 | UGUGACCCUAGAAUAAUUAC | 3351 | AAUUAUUCUAGGGUCACAUU |
| hsa-miR-7974 | 3352 | AGGCUGUGAUGCUCUCCUGAGCCC | 3353 | GCUCAGGAGAGCAUCACAGCCUUU |
| hsa-miR-7975 | 3354 | AUCCUAGUCACGGCACCA | 3355 | GUGCCGUGACUAGGAUUU |
| hsa-miR-7976 | 3356 | UGCCCUGAGACUUUUGCUC | 3357 | GCAAAAGUCUCAGGGCAUU |
| hsa-miR-7977 | 3358 | UUCCCAGCCAACGCACCA | 3359 | GUGCGUUGGCUGGGAAUU |
| hsa-miR-7978 | 3360 | UCUGGUGUAUAGCGUUGCUCA | 3361 | AGCAACGCUAUACACCAGAUU |
| hsa-miR-802 | 3362 | CAGUAACAAAGAUUCAUCCUUGU | 3363 | AAGGAUGAAUCUUUGUUACUGUU |
| hsa-miR-8052 | 3364 | CGGGACUGUAGAGGGCAUGAGC | 3365 | UCAUGCCCUCUACAGUCCCGUU |
| hsa-miR-8053 | 3366 | UGGCGAUUUUGGAACUCAAUGGCA | 3367 | CCAUUGAGUUCCAAAAUCGCCAUU |
| hsa-miR-8054 | 3368 | GAAAGUACAGAUCGGAUGGGU | 3369 | CCAUCCGAUCUGUACUUUCUU |
| hsa-miR-8055 | 3370 | CUUUGAGCACAUGAGCAGACGGA | 3371 | CGUCUGCUCAUGUGCUCAAAGUU |
| hsa-miR-8056 | 3372 | CGUGGAUUGUCUGGAUGCAU | 3373 | GCAUCCAGACAAUCCACGUU |
| hsa-miR-8057 | 3374 | GUGGCUCUGUAGUAAGAUGGA | 3375 | CAUCUUACUACAGAGCCACUU |
| hsa-miR-8058 | 3376 | CUGGACUUUGAUCUUGCCAUAA | 3377 | AUGGCAAGAUCAAAGUCCAGUU |
| hsa-miR-8059 | 3378 | GGGGAACUGUAGAUGAAAGGC | 3379 | CUUUUCAUCUACAGUUCCCCUU |
| hsa-miR-8060 | 3380 | CCAUGAAGCAGUGGGUAGGAGGAC | 3381 | CCUCCUACCCACUGCUUCAUGGUU |
| hsa-miR-8061 | 3382 | CUUAGAUUAGAGGAUAUUGUU | 3383 | CAAUAUCCUCUAAUCUAAGUU |
| hsa-miR-8062 | 3384 | CAGUGAUUUGAGGAUUAUUGC | 3385 | AAUAAUCCUCAAAUCACUGUU |

TABLE 1-continued miRNA Sequences

| miRNA | SEQ ID NO: | Sequence 1 | SEQ ID NO: | Sequence 2 |
|---|---|---|---|---|
| hsa-miR-8063 | 3386 | UCAAAAUCAGGAGUCGGGGCUU | 3387 | GCCCCGACUCCUGAUUUUGAUU |
| hsa-miR-8064 | 3388 | AGCACACUGAGCGAGCGGAC | 3389 | CCGCUCGCUCAGUGUGCUUU |
| hsa-miR-8065 | 3390 | UGUAGGAACAGUUGAAUUUUGGCU | 3391 | CCAAAAUUCAACUGUUCCUACAUU |
| hsa-miR-8066 | 3392 | CAAUGUGAUCUUUUGGAUGUA | 3393 | CAUCCAAAAGAUCACAUUGUU |
| hsa-miR-8067 | 3394 | CCUAGAAACUGUAAACUUAGUC | 3395 | CUAAGUUUACAGUUUCUAGGUU |
| hsa-miR-8068 | 3396 | UGUUUGUUGUAAGGAUCGUUGU | 3397 | AACGAUCCUUACAACAAACAUU |
| hsa-miR-8069 | 3398 | GGAUGGUUGGGGGCGGUCGGCGU | 3399 | GCCGACCGCCCCCAACCAUCCUU |
| hsa-miR-8070 | 3400 | AUGUGAUUGACGGCUGACUCCA | 3401 | GAGUCAGCCGUCAAUCACAUUU |
| hsa-miR-8071 | 3402 | CGGUGGACUGGAGUGGGUGG | 3403 | ACCCACUCCAGUCCACCGUU |
| hsa-miR-8072 | 3404 | GGCGGCGGGGAGGUAGGCAG | 3405 | GCCUACCUCCCCGCCGCCUU |
| hsa-miR-8073 | 3406 | ACCUGGCAGCAGGGAGCGUCGU | 3407 | GACGCUCCCUGCUGCCAGGUUU |
| hsa-miR-8074 | 3408 | CUAUGGCGAGACUGGCAUGUACUC | 3409 | GUACAUGCCAGUCUCGCCAUAGUU |
| hsa-miR-8075 | 3410 | UGCUGAUGGCAGAUGUCGGGUCUG | 3411 | GACCCGACAUCUGCCAUCAGCAUU |
| hsa-miR-8076 | 3412 | UAUAUGGACUUUCUGAUACAAUG | 3413 | UUGUAUCAGAAAAGUCCAUAUAUU |
| hsa-miR-8077 | 3414 | GGCUGAGUGGGGUUCUGACUCC | 3415 | AGUCAGAACCCCACUCAGCCUU |
| hsa-miR-8078 | 3416 | GGUCUAGGCCCGGUGAGAGACUC | 3417 | GUCUCUCACCGGGCCUAGACCUU |
| hsa-miR-8079 | 3418 | CAGUGAUCGUCUCUGCUGGC | 3419 | CAGCAGAGACGAUCACUGUU |
| hsa-miR-8080 | 3420 | GAAGGACACUGGUGUCAACGGCU | 3421 | CCGUUGACACCAGUGUCCUUCUU |
| hsa-miR-8081 | 3422 | CUUGAGUCGUGCCUUUCUGAAUG | 3423 | UUCAGAAAGGCACGACUCAAGUU |
| hsa-miR-8082 | 3424 | UGAUGGAGCUGGGAAUACUCUG | 3425 | GAGUAUUCCCAGCUCCAUCAUU |
| hsa-miR-8083 | 3426 | CAGGACUUGACGGCUGCAACU | 3427 | UUGCAGCCGUCAAGUCCUGUU |
| hsa-miR-8084 | 3428 | GAAUACUAAGUAAAAAUCAGUA | 3429 | CUGAUUUUUACUUAGUAUUCUU |
| hsa-miR-8085 | 3430 | UGGGAGAGAGGACUGUGAGGC | 3431 | CUCACAGUCCUCUCUCCCAUU |
| hsa-miR-8086 | 3432 | UGCUAGUCUGGACUGAUAUGGU | 3433 | CAUAUCAGUCCAGACUAGCAUU |
| hsa-miR-8087 | 3434 | GAAGACUUCUUGGAUUACAGGGG | 3435 | CCUGUAAUCCAAGAAGUCUUCUU |
| hsa-miR-8088 | 3436 | CCUCGGUACUGGAAAGGGGUA | 3437 | CCCCUUUCCAGUACCGAGGUU |
| hsa-miR-8089 | 3438 | CCUGGGGACAGGGGAUUGGGCAG | 3439 | GCCCCAAUCCCCUGUCCCCAGGUU |
| hsa-miR-8485 | 3440 | CACACACACACACACACGUAU | 3441 | ACGUGUGUGUGUGUGUGUUU |
| hsa-miR-873 | 3442 | GCAGGAACUUGUGAGUCUCCU | 3443 | GGAGACUGAUGAGUUCCCGGGA |
| hsa-miR-874 | 3444 | CGGCCCACGCACCAGGGUAAGA | 3445 | CUGCCCUGGCCCGAGGGACCGA |
| hsa-miR-875 | 3446 | UAUACCUCAGUUUUAUCAGGUG | 3447 | CCUGGAAACACUGAGGUUGUG |
| hsa-miR-876 | 3448 | UGGAUUUCUUUGUGAAUCACCA | 3449 | UGGUGGUUUACAAAGUAAUUCA |
| hsa-miR-877 | 3450 | UCCUCUUCUCCCUCCUCCCAG | 3451 | GUAGAGGAGAUGGCGCAGGG |
| hsa-miR-885 | 3452 | UCCAUUACACUACCCUGCCUCU | 3453 | AGGCAGCGGGGUGUAGUGGAUA |
| hsa-miR-887 | 3454 | CUUGGGAGCCCUGUUAGACUC | 3455 | GUGAACGGGCGCCAUCCCGAGG |
| hsa-miR-888 | 3456 | UACUCAAAAAGCUGUCAGUCA | 3457 | GACUGACACCUCUUUGGGUGAA |
| hsa-miR-889 | 3458 | AAUGGCUGUCCGUAGUAUGGUC | 3459 | UUAAUAUCGGACAACCAUUGU |

TABLE 1-continued miRNA Sequences

| miRNA | SEQ ID NO: | Sequence 1 | SEQ ID NO: | Sequence 2 |
|---|---|---|---|---|
| hsa-miR-890 | 3460 | UACUUGGAAAGGCAUCAGUUG | 3461 | ACUGAUGCCUUUCCAAGUAUU |
| hsa-miR-891a | 3462 | AGUGGCACAUGUUUGUUGUGAG | 3463 | UGCAACGAACCUGAGCCACUGA |
| hsa-miR-891b | 3464 | UGCAACUUACCUGAGUCAUUGA | 3465 | AAUGACUCAGGUAAGUUGCAUU |
| hsa-miR-892a | 3466 | CACUGUGUCCUUUCUGCGUAG | 3467 | ACGCAGAAAGGACACAGUGUU |
| hsa-miR-892b | 3468 | CACUGGCUCCUUUCUGGGUAGA | 3469 | UACCCAGAAAGGAGCCAGUGUU |
| hsa-miR-892c | 3470 | CACUGUUUCCUUUCUGAGUGGA | 3471 | UAUUCAGAAAGGUGCCAGUCA |
| hsa-miR-9 | 3472 | UCUUUGGUUAUCUAGCUGUAUGA | 3473 | AUAAAGCUAGAUAACCGAAAGU |
| hsa-miR-920 | 3474 | GGGGAGCUGUGGAAGCAGUA | 3475 | CUGCUUCCACAGCUCCCCUU |
| hsa-miR-921 | 3476 | CUAGUGAGGGACAGAACCAGGAUUC | 3477 | AUCCUGGUUCUGUCCCUCACUAGUU |
| hsa-miR-922 | 3478 | GCAGCAGAGAAUAGGACUACGUC | 3479 | CGUAGUCCUAUUCUCUGCUGCUU |
| hsa-miR-924 | 3480 | AGAGUCUUGUGAUGUCUUGC | 3481 | AAGACAUCACAAGACUCUUU |
| hsa-miR-92a-1 | 3482 | UAUUGCACUUGUCCCGGCCUGU | 3483 | AGGUUGGGAUCGGUUGCAAUGCU |
| hsa-miR-92a-2 | 3484 | UAUUGCACUUGUCCCGGCCUGU | 3485 | GGGUGGGGAUUUGUUGCAUUAC |
| hsa-miR-92b | 3486 | UAUUGCACUCGUCCCGGCCUCC | 3487 | AGGGACGGGACGCGGUGCAGUG |
| hsa-miR-93 | 3488 | ACUGCUGAGCUAGCACUUCCCG | 3489 | CAAAGUGCUGUUCGUGCAGGUAG |
| hsa-miR-933 | 3490 | UGUGCGCAGGGAGACCUCUCCC | 3491 | GAGAGGUCUCCCUGCGCACAUU |
| hsa-miR-934 | 3492 | UGUCUACUACUGGAGACACUGG | 3493 | AGUGUCUCCAGUAGUAGACAUU |
| hsa-miR-935 | 3494 | CCAGUUACCGCUUCCGCUACCGC | 3495 | GGUAGCGGAAGCGGUAACUGGUU |
| hsa-miR-936 | 3496 | ACAGUAGAGGGAGGAAUCGCAG | 3497 | GCGAUUCCUCCCUCUACUGUUU |
| hsa-miR-937 | 3498 | AUCCGCGCUCUGACUCUCUGCC | 3499 | GUGAGUCAGGGUGGGCUGG |
| hsa-miR-938 | 3500 | UGCCCUUAAAGGUGAACCCAGU | 3501 | UGGGUUCACCUUUAAGGGCAUU |
| hsa-miR-939 | 3502 | CCCUGGGCCUCUGCUCCCCAG | 3503 | UGGGGAGCUGAGGCUCUGGGGGUG |
| hsa-miR-940 | 3504 | AAGGCAGGGCCCCCGCUCCCC | 3505 | GGAGCGGGGCCCUGCCUUUU |
| hsa-miR-941 | 3506 | CACCCGGCUGUGUGCACAUGUGC | 3507 | ACAUGUGCACACAGCCGGGUGUU |
| hsa-miR-942 | 3508 | UCUUCUCUGUUUUGGCCAUGUG | 3509 | CACAUGGCCGAAACAGAGAAGU |
| hsa-miR-943 | 3510 | CUGACUGUUGCCGUCCUCCAG | 3511 | GGAGGACGGCAACAGUCAGUU |
| hsa-miR-944 | 3512 | AAAUUAUUGUACAUCGGAUGAG | 3513 | CAUCCGAUGUACAAUAAUUUUU |
| hsa-miR-95 | 3514 | UCAAUAAAUGUCUGUUGAAUU | 3515 | UUCAACGGGUAUUUAUUGAGCA |
| hsa-miR-9500 | 3516 | AAGGGAAGAUGGUGACCAC | 3517 | GGUCACCAUCUUCCCUUUU |
| hsa-miR-96 | 3518 | UUUGGCACUAGCACAUUUUUGCU | 3519 | AAUCAUGUGCAGUGCCAAUAUG |
| hsa-miR-98 | 3520 | CUAUACAACUUACUACUUUCCC | 3521 | UGAGGUAGUAAGUUGUAUUGUU |
| hsa-miR-99a | 3522 | CAAGCUCGCUUCUAUGGGUCUG | 3523 | AACCCGUAGAUCCGAUCUUGUG |
| hsa-miR-99b | 3524 | CACCCGUAGAACCGACCUUGCG | 3525 | CAAGCUCGUGUCUGUGGGUCCG |

Example 2: Measurement of Activity of miRNA Library Sample

In order to determine whether the double-stranded miRNAs synthesized in Example 1 would be active, miR-34a, miR-100 and miR-125b were selected from the consisting of about 1700 kinds of miRNAs. The selected miRNAs were selected because there are many studies on target mRNAs whose functions and expressions are to be controlled and on regions binding to mRNA 3'UTR. The 3' UTR region of each of Bcl2, mTOR and Lin28b mRNA, expressions of which are known to be controlled by each of miR-34a, miR-100 and miR-125b, was substituted into the 3' UTR of a firefly luciferase vector, thereby constructing a vector corresponding to each of the miRNAs. Each vector and an miR control, or miR-34a, miR-100 or miR-125b corresponding to each vector, were co-transfected into HEK-293T cells by use of Lipofectamine 2000 (Lipofectamine 2000, Invitrogen) which is an intracellular oligo delivery reagent (preparation of triplicate samples), and the cells were cultured under the conditions of 37° C. and 5% (v/v) $CO_2$ for 24 hours. Luciferase activity was measured by a luminometer (Thermo scientific) to determine the activities of the synthesized miRNAs (FIG. 1).

Figure 2:
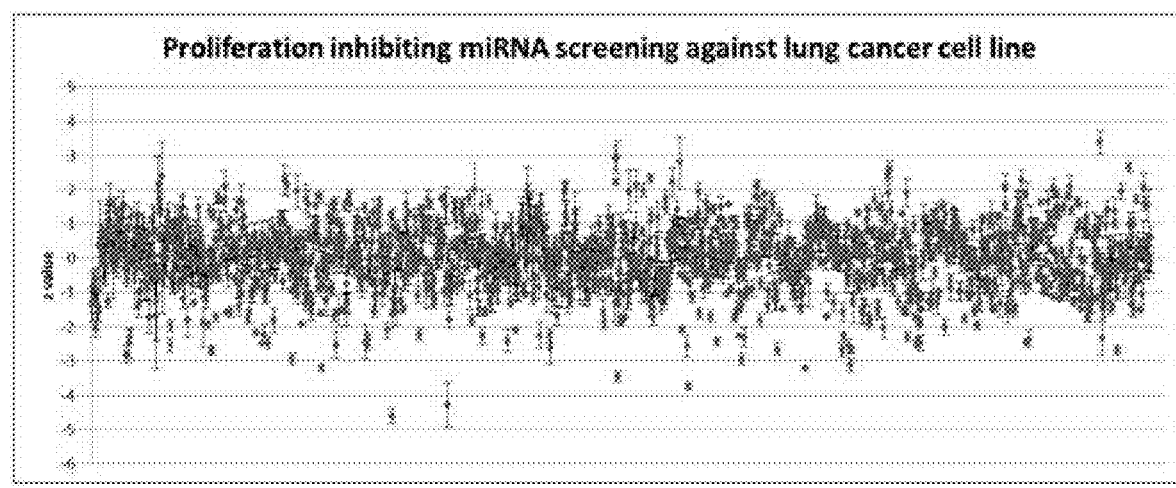
FIG. 2 shows the results obtained by treating lung cancer NCI-H460 cells with a screening library consisting of about 1700 kinds of miRNAs, quantifying the growth of the cells using Resazurin reagent, and expressing the quantification results as relative growth values.

Example 3: Screening for Identification of microRNAs that Inhibit Proliferation of Lung Cancer Cells 3,000-40,000 NCI-H460 cells were dispensed in each well of 96-well plates and cultured under the conditions of 37° C. and 5% (v/v) $CO_2$ for 24 hours, and then each of the miRNAs selected from the miRNA library was transfected into the cells to a final concentration of 100 nM by use of RNAiMAX reagent (Invitrogen). Since each miRNA was transfected three times, three 96-well plates were prepared per each miRNA. The cells were further cultured under the same conditions as described above for 24 hours, and then the fluorescence value generated by addition of Resazurin reagent (Promega) was measured using a fluorometer (Tecan). To comparatively evaluate the cell growth inhibitory abilities of the miRNAs, the mean value and standard deviation of the 96 values measured for the 96-well plate were calculated, and the standard deviation multiple (Z-score) of the value measured for each well (containing each miRNA) from the mean value was calculated using the following equation:

$$z_i = \frac{x_i - \mu}{\sigma}$$

wherein x is the value measured in each well, μ is the mean value of the values measured for all the wells of the plate, and σ is standard deviation. The standard deviation multiple $z_i$ of each well was the mean value of the values obtained for the triplicate plates, and about first candidate miRNAs showing a $z_i$ value smaller than −2 were selected (FIG. 2 and Table 2).

TABLE 2

First Selected miRNA Sequences

| | | |
|---|---|---|
| SEQ ID NO: 1 hsa-miR-23c | Strand 1 | AUCACAUUGCCAGUGAUUACCC |
| SEQ ID NO: 2 hsa-miR-23c | Strand 2 | GUAAUCACUGGCAAUGUGAUUU |
| SEQ ID NO: 3 hsa-miR-219b | Strand 1 | AGAUGUCCAGCCACAAUUCUCG |
| SEQ ID NO: 4 hsa-miR-219b | Strand 2 | AGAAUUGCGUUUGGACAAUCAGU |
| SEQ ID NO: 5 hsa-miR-378c | Strand 1 | ACUGGACUUGGAGUCAGAAGAGUGG |
| SEQ ID NO: 6 hsa-miR-378c | Strand 2 | ACUCUUCUGACUCCAAGUCCAGUUU |
| SEQ ID NO: 7 hsa-miR-548aa | Strand 1 | AAAAACCACAAUUACUUUUGCACCA |
| SEQ ID NO: 8 hsa-miR-548aa | Strand 2 | GUGCAAAAGUAAUUGUGGUUUUUUU |
| SEQ ID NO: 9 hsa-miR-548u | Strand 1 | CAAAGACUGCAAUUACUUUUGCG |
| SEQ ID NO: 10 hsa-miR-548u | Strand 2 | CAAAAGUAAUUGCAGUCUUUGUU |
| SEQ ID NO: 11 hsa-miR-571 | Strand 1 | UGAGUUGGCCAUCUGAGUGAG |
| SEQ ID NO: 12 hsa-miR-571 | Strand 2 | CACUCAGAUGGCCAACUCAUU |
| SEQ ID NO: 13 hsa-miR-641 | Strand 1 | AAAGACAUAGGAUAGAGUCACCUC |
| SEQ ID NO: 14 hsa-miR-641 | Strand 2 | GGUGACUCUAUCCUAUGUCUUUUU |
| SEQ ID NO: 15 hsa-miR-1244 | Strand 1 | AAGUAGUUGGUUUGUAUGAGAUGGUU |
| SEQ ID NO: 16 hsa-miR-1244 | Strand 2 | CCAUCUCAUACAAACCAACUACUUUU |
| SEQ ID NO: 17 hsa-miR-1248 | Strand 1 | ACCUUCUUGUAUAAGCACUGUGCUAAA |
| SEQ ID NO: 18 hsa-miR-1248 | Strand 2 | UAGCACAGUGCUUAUACAAGAAGGUUU |
| SEQ ID NO: 19 hsa-miR-1298 | Strand 1 | CAUCUGGGCAACUGACUGAAC |
| SEQ ID NO: 20 hsa-miR-1298 | Strand 2 | UUCAUUCGGCUGUCCAGAUGUA |
| SEQ ID NO: 21 hsa-miR-2392 | Strand 1 | UAGGAUGGGGGUGAGAGGUG |
| SEQ ID NO: 22 hsa-miR-2392 | Strand 2 | CCUCUCACCCCCAUCCUAUU |
| SEQ ID NO: 23 hsa-miR-3119 | Strand 1 | UGGCUUUUAACUUUGAUGGC |
| SEQ ID NO: 24 hsa-miR-3119 | Strand 2 | CAUCAAAGUUAAAAGCCAUU |

TABLE 2-continued

First Selected miRNA Sequences

| | | | |
|---|---|---|---|
| SEQ ID NO: 25 | hsa-miR-3164 | Strand 1 | UGUGACUUUAAGGGAAAUGGCG |
| SEQ ID NO: 26 | hsa-miR-3164 | Strand 2 | CCAUUUCCCUUAAAGUCACAUU |
| SEQ ID NO: 27 | hsa-miR-3188 | Strand 1 | AGAGGCUUUGUGCGGAUACGGGG |
| SEQ ID NO: 28 | hsa-miR-3188 | Strand 2 | CCGUAUCCGCACAAAGCCUCUUU |
| SEQ ID NO: 29 | hsa-miR-3609 | Strand 1 | CAAAGUGAUGAGUAAUACUGGCUG |
| SEQ ID NO: 30 | hsa-miR-3609 | Strand 2 | GCCAGUAUUACUCAUCACUUUGUU |
| SEQ ID NO: 31 | hsa-miR-3612 | Strand 1 | AGGAGGCAUCUUGAGAAAUGGA |
| SEQ ID NO: 32 | hsa-miR-3612 | Strand 2 | CAUUUCUCAAGAUGCCUCCUUU |
| SEQ ID NO: 33 | hsa-miR-3662 | Strand 1 | GAAAAUGAUGAGUAGUGACUGAUG |
| SEQ ID NO: 34 | hsa-miR-3662 | Strand 2 | UCAGUCACUACUCAUCAUUUUCUU |
| SEQ ID NO: 35 | hsa-miR-3670 | Strand 1 | AGAGCUCACAGCUGUCCUUCUCUA |
| SEQ ID NO: 36 | hsa-miR-3670 | Strand 2 | GAGAAGGACAGCUGUGAGCUCUUU |
| SEQ ID NO: 37 | hsa-miR-3943 | Strand 1 | UAGCCCCCAGGCUUCACUUGGCG |
| SEQ ID NO: 38 | hsa-miR-3943 | Strand 2 | CCAAGUGAAGCCUGGGGGCUAUU |
| SEQ ID NO: 39 | hsa-miR-4424 | Strand 1 | AGAGUUAACUCAAAAUGGACUA |
| SEQ ID NO: 40 | hsa-miR-4424 | Strand 2 | GUCCAUUUUGAGUUAACUCUUU |
| SEQ ID NO: 41 | hsa-miR-4461 | Strand 1 | GAUUGAGACUAGUAGGGCUAGGC |
| SEQ ID NO: 42 | hsa-miR-4461 | Strand 2 | CUAGCCCUACUAGUCUCAAUCUU |
| SEQ ID NO: 43 | hsa-miR-4477a | Strand 1 | CUAUUAAGGACAUUUGUGAUUC |
| SEQ ID NO: 44 | hsa-miR-4477a | Strand 2 | AUCACAAAUGUCCUUAAUAGUU |
| SEQ ID NO: 45 | hsa-miR-4477b | Strand 1 | AUUAAGGACAUUUGUGAUUGAU |
| SEQ ID NO: 46 | hsa-miR-4477b | Strand 2 | CAAUCACAAAUGUCCUUAAUUUU |
| SEQ ID NO: 47 | hsa-miR-4765 | Strand 1 | UGAGUGAUUGAUAGCUAUGUUC |
| SEQ ID NO: 48 | hsa-miR-4765 | Strand 2 | ACAUAGCUAUCAAUCACUCAUU |
| SEQ ID NO: 49 | hsa-miR-4773 | Strand 1 | CAGAACAGGAGCAUAGAAAGGC |
| SEQ ID NO: 50 | hsa-miR-4773 | Strand 2 | CUUUCUAUGCUCCUGUUCUGUU |
| SEQ ID NO: 51 | hsa-miR-4776 | Strand 1 | GUGGACCAGGAUGGCAAGGGCU |
| SEQ ID NO: 52 | hsa-miR-4776 | Strand 2 | CUUGCCAUCCUGGUCCACUGCAU |
| SEQ ID NO: 53 | hsa-miR-4999 | Strand 1 | UGCUGUAUUGUCAGGUAGUGA |
| SEQ ID NO: 54 | hsa-miR-4999 | Strand 2 | UCACUACCUGACAAUACAGU |
| SEQ ID NO: 55 | hsa-miR-5096 | Strand 1 | GUUUCACCAUGUUGGUCAGGC |
| SEQ ID NO: 56 | hsa-miR-5096 | Strand 2 | CUGACCAACAUGGUGAAACUU |
| SEQ ID NO: 57 | hsa-miR-5697 | Strand 1 | UCAAGUAGUUUCAUGAUAAAGG |
| SEQ ID NO: 58 | hsa-miR-5697 | Strand 2 | UUUAUCAUGAAACUACUUGAUU |
| SEQ ID NO: 59 | hsa-miR-5705 | Strand 1 | UGUUUCGGGGCUCAUGGCCUGUG |
| SEQ ID NO: 60 | hsa-miR-5705 | Strand 2 | CAGGCCAUGAGCCCCGAAACAUU |
| SEQ ID NO: 61 | hsa-miR-5707 | Strand 1 | ACGUUUGAAUGCUGUACAAGGC |
| SEQ ID NO: 62 | hsa-miR-5707 | Strand 2 | CUUGUACAGCAUUCAAACGUUU |
| SEQ ID NO: 63 | hsa-miR-8053 | Strand 1 | UGGCGAUUUUGGAACUCAAUGGCA |

TABLE 2-continued

First Selected miRNA Sequences

| SEQ ID NO: 64 | hsa-miR-8053 | Strand 2 | CCAUUGAGUUCCAAAAUCGCCAUU |
| SEQ ID NO: 65 | hsa-miR-8078 | Strand 1 | GGUCUAGGCCCGGUGAGAGACUC |
| SEQ ID NO: 66 | hsa-miR-8078 | Strand 2 | GUCUCUCACCGGGCCUAGACCUU |

Figure 3:
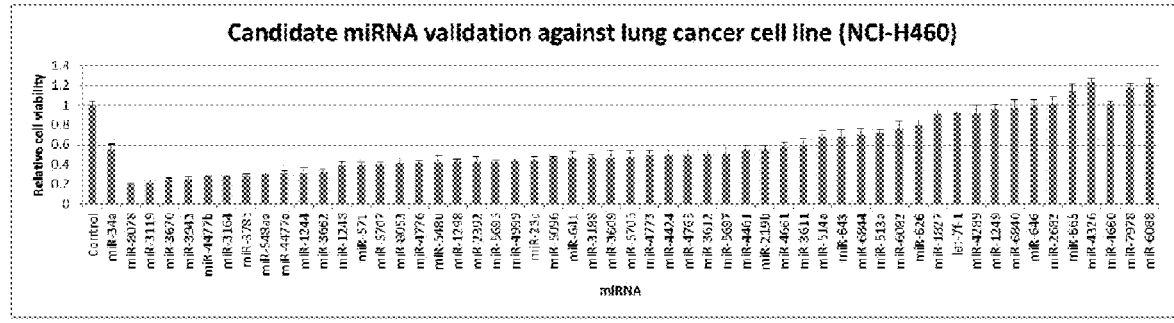
FIG. 3 shows the results obtained by selecting about 50 kinds of miRNAs showing excellent efficacy in the NCI-H460 cell line, and measuring the relative cancer cell growth inhibitory abilities of the selected miRNAs using WST-1 reagent.

Example 4: Second Screening for Identification of miRNAs that Inhibit Proliferation of Lung Cancer Cells Using about 50 miRNA candidates obtained in first screening, second screening was performed with increased measurement precision. The experiment was performed under the same conditions as first screening, except that WST-1 reagent (Roche) was used instead of the Resazurin reagent to measure the proliferation potential of the cells. WST-1 has an advantage over Resazurin in that the intensity of signals can be more quantitatively measured. The values obtained by measuring the cell proliferation inhibitory ability of each miRNA were expressed as values relative to the control, and the results are shown in FIG. 3. As a positive control, miR-34a was used.

Example 5: Analysis of the Ability to Induce Cell Apoptosis

Figure 4:
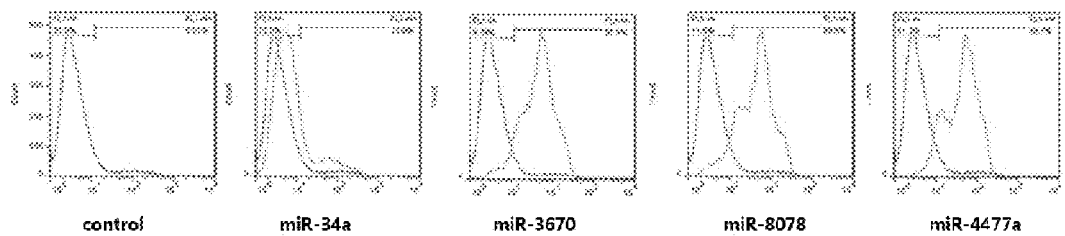
FIG. 4 shows the results obtained by transfecting each of miR-34a, miR-3670, miR-8078 and miR-4477a into a lung cancer cell line, staining the cells with FITC-labeled Annexin V, and analyzing the stained cells by flow cytometery to determine the apoptotic effect of the miRNAs on the lung cancer cell line.

The method used in screening is a method of measuring the relative inhibition of cell proliferation by quantitatively measuring the number of cells. Mechanisms by which cell proliferation is inhibited include a method of reducing cell division rate, and a method of inducing apoptosis. In order to analyze the mechanism by which the miRNAs found in the present invention inhibit cell proliferation, the degree of apoptosis was analyzed using the Fluorescence Activated Cell Sorter (FACS). Specifically, cells were dispensed in 6-well plates, and the miRNA was transfected into the cells by use of RNAiMAX reagent, and then the cells were cultured under the same conditions as described above for 48 hours. Next, the cells treated with FITC-labeled Annexin V and analyzed using the Fluorescence Activated Cell Sorter (FACS) (FIG. 4). The results of the analysis indicated that the cells treated with each of miR-3670, miR-4477a and miR-8078 were mostly dead. This suggests that the tumor cell growth inhibitory effect of the miRNA identified in screening resulted from induction of apoptosis (Table 3).

Example 6: Inhibition of Tumor Cell Growth on Soft Agar by miRNAs

Figure 5:
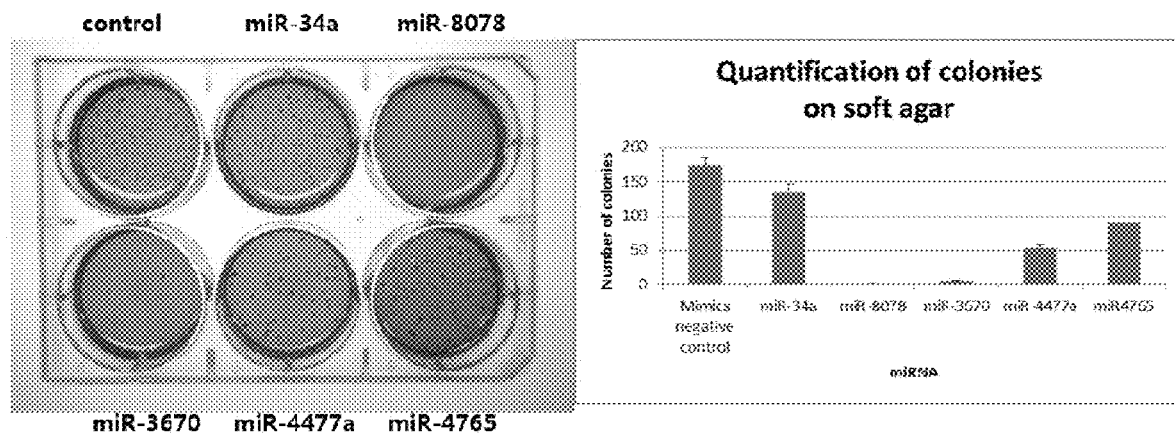
FIG. 5 shows the results obtained by transfecting each miRNA into a lung cancer cell line, culturing the cells on soft agar for 2 weeks, and measuring the effects of the miRNAs against the colony-forming ability of the lung cancer cell line.

When tumor cells were cultured using soft agar, the characteristic of tumor cells can be measured. Normal cells require a support such as a culture dish for growth, whereas tumor cells are characterized by growing even in an environment such as soft agar, which is free of a physically strong support. Using this tumor-specific characteristic, cell colony-forming ability on soft agar was examined NCI-H460 lung cancer cells were treated with each of control miRNA, miR-34a, miR-8078, miR-3670, miR-4477a and miR-4765, and cultured for 24 hours. Next, the cells were mixed with soft agar and cultured in 6-well plates for 2 weeks. The cells were stained with crystal violet, and the number of colonies in each group was measured (FIG. 5). As a result, it could be seen that the cells treated with miR-8078 or miR-3670 formed little or no colonies, and the cells treated with miR-4477a showed colony-forming ability equal to about 30% of that of the control group.

Example 7: Measurement of Cell Proliferation Inhibitory Effects of miRNAs Upon Knock-Down of Target mRNA Target mRNA whose expression is controlled by miRNA has a sequence complementary to a portion of the miRNA sequence. The seed region sequence of the miRNA is particularly important in inhibition of mRNA, because the seed region sequence binds to mRNA having a sequence complementary thereto to inhibit gene expression. However, since the seed region sequence is relatively short (8-9 nucleotides), mRNAs to be targeted by miRNA are predicted using software. However, it is known that, even when software is used, only some of predicted targets are substantial targets. In order to overcome this disadvantage, the

TABLE 3

Finally Selected miRNA Sequences

| SEQ ID NO: 35 | hsa-miR-3670 | Strand 1 | AGAGCUCACAGCUGUCCUUCUCUA |
| SEQ ID NO: 36 | hsa-miR-3670 | Strand 2 | GAGAAGGACAGCUGUGAGCUCUUU |
| SEQ ID NO: 67 | miR-3670-IC | IC | GACUGGUAUAGCUGCUUUUGGAGCCUCA |
| SEQ ID NO: 43 | hsa-miR-4477a | Strand 1 | CUAUUAAGGACAUUUGUGAUUC |
| SEQ ID NO: 44 | hsa-miR-4477a | Strand 2 | AUCACAAAUGUCCUUAAUAGUU |
| SEQ ID NO: 68 | miR-4477a-IC | IC | AUCACAAAUGUCCUUAAUGGCA |
| SEQ ID NO: 65 | hsa-miR-8078 | Strand 1 | GGUCUAGGCCCGGUGAGAGACUC |
| SEQ ID NO: 66 | hsa-miR-8078 | Strand 2 | GUCUCUCACCGGGCCUAGACCUU |
| SEQ ID NO: 69 | miR-8078-IC | IC | CUCCACCGGGCUGACCGGCCUG | intracellular contents of target genes predicted through software were reduced using siRNA, and then whether or not the growth of the cells would be inhibited was determined, thereby selecting target genes. To predict target mRNAs to be targeted by miRNA, TargetScan that is generally used in the art was used as target prediction software, and about 600 kinds of genes predicted to be targeted by miR-3670, miR-4477a or miR-8078 were selected. For each of the selected genes, 3 kinds of siRNAs were synthesized, and using the synthesized siRNAs, the experiment was performed in the same manner as described in Example 3. Specifically, cells were dispensed in 96-well plates, treated with each siRNA, and then cultured for 48 hours, after which the ability of the cell to proliferate was measured using Resazurin. In the same manner as described in Example 3, the Z-score of each gene was calculated from the mean of the values measured for a total of 1800 samples (about 600 genes×three different siRNAs). The results are shown in FIG. 6.

Example 8: Analysis of mRNA Targeted by miRNA miRNA acts to inhibit protein from being produced from mRNA and to induce degradation of most mRNAs targeted thereby. Thus, miRNA is transfected into cells, and the intracellular content of mRNA to be targeted by miRNA is analyzed by qPCR to determine whether or not the content would be reduced, thereby determining whether or not the miRNA would target the mRNA. In order to determine whether or not the intracellular contents of the target genes found in Example 7 would be substantially reduced when miRNA was delivered into cells, each of miR-3670, miR-4477a and miR-8078 was transfected into lung cancer cells which were then cultured for 48 hours, after which RNA was extracted from each cell, and the content of RNA in the cells was quantitatively measured (FIG. 7). As a result, it could be seen that the content of mRNA predicted to be targeted by each of miR-3670, miR-4477a and miR-8078 was significantly reduced.

Example 9: Examination of Target mRNA by Luciferase Assay miRNA binds to the 3' UTR (untranslated region) of target mRNA to inhibit protein from being produced from the target mRNA. For this reason, a luciferase assay method is generally used to directly measures the relationship between miRNA and target mRNA. Under TargetScan software, a 3' UTR sequence containing a miRNA-binding sequence was provided. As described in Example 2 above, the 3' UTR sequence was cloned into the 3' UTR of firefly luciferase to construct a vector. The constructed vector and miRNA were co-transfected into human embryonic kidney (HEK) cells, and the luciferase expression level of the vector was measured. To correct transfection efficiency, renilla luciferase was also transfected. After co-transfection of miRNA, firefly luciferase and renilla luciferase, the cells were cultured for 48 hours, and the luciferase activity of the cells was measured by a luminometer (FIG. 9). As a result, it could be seen that the target mRNA was controlled directly by the corresponding miRNA.

INDUSTRIAL APPLICABILITY

As described above, the pharmaceutical composition for treatment of cancer according to the present invention contains, as an active ingredient, one or more miRNAs selected from the group consisting of miR-3670, miR-4477a, and miR-8078. The pharmaceutical composition of the present invention exhibits improved anticancer effects compared to miR-34a, which is currently under clinical trials to determine suitability as an anticancer agent, and other pharmaceutical compositions for treatment of cancer, which contain other miRNAs as active ingredients. Thus, the pharmaceutical composition of the present invention can be widely used as an anticancer composition.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10612026B2). An electronic copy of the "Sequence Listing" will also be available from the USPTO upon request and payment of the fee set forth in 37 CFR 1.19(b)(3).

What is claimed is:

1. A method for treating cancer, comprising administering a pharmaceutical composition comprising miR-8078 as an active ingredient to a patient/subject in need of cancer treatment, wherein the miR-8078 comprises a double-stranded RNA represented by the nucleotide sequences of SEQ ID NO: 65 and SEQ ID NO: 66; or SEQ ID NO: 65 and SEQ ID NO: 69, as an active ingredient.

2. The method of claim 1, wherein the miRNA induces cancer cell apoptosis to treat the cancer.

3. The method of claim 1, wherein the cancer is one or more cancers selected from the group consisting of: primary cancers; metastatic carcinomas arising from metastasis to other organs from a primary cancer site of origin; and neoplastic cell disease caused by the promotion of abnormally excessive cell division.

4. The method of claim 1, wherein the cancer is one or more primary cancers.

5. The method of claim 4, wherein said primary cancers comprise lung cancer, liver cancer, stomach cancer, colorectal cancer, pancreatic cancer, gallbladder and bile duct cancer, breast cancer, leukemia, esophageal cancer, non-Hodgkin lymphoma, thyroid cancer, cervical cancer, and skin cancer.

6. The method of claim 1, wherein the cancer is a metastatic carcinoma arising from metastasis to other organs from a primary cancer site of origin.

7. The method of claim 1, wherein the cancer is a neoplastic cell disease caused by the promotion of abnormally excessive cell division.

8. The method of claim 1, wherein the miRNA is a miRNA mimic.

9. The method of claim 8, wherein the miRNA mimic is selected from the group consisting of: one partially including a phosphorothioate structure in which a RNA phosphate backbone structure is substituted with another element; one in which RNA is wholly or partially substituted with DNA, PNA (peptide nucleic acid) or LNA (locked nucleic acid) molecule; and one in which 2' hydroxyl group of RNA sugar is substituted with various functional structures.

10. The method of claim 9, wherein said another element is sulfur.

11. The method of claim 9, wherein said various functional structures include at least one of methylation, methoxylation, and fluorination.

12. The method of claim 8, the miRNA mimic consists of a miRNA precursor in the form of pri-miRNA or precursor miRNA; or a miRNA precursor in the form of plasmid.

13. The method of claim 12, wherein the miRNA precursor is selected from the group consisting of: one partially comprising a phosphorothioate structure in which a RNA phosphate backbone structure is substituted with another element; one in which RNA is wholly or partially substituted with DNA, PNA (peptide nucleic acid) or LNA (locked nucleic acid) molecule; and one in which 2' hydroxyl group of RNA sugar is substituted with various functional structures.

14. The method of claim 13, wherein said another element is sulfur.

15. The method of claim 13, wherein said various functional structures include at least one of methylation, methoxylation, and fluorination.

* * * * *

UNITED STATES PATENT AND TRADEMARK OFFICE
CERTIFICATE OF CORRECTION

PATENT NO. : 10,612,026 B2
APPLICATION NO. : 16/371026
DATED : April 7, 2020
INVENTOR(S) : Taewoo Lee Page 1 of 1

It is certified that error appears in the above-identified patent and that said Letters Patent is hereby corrected as shown below:

In the Specification

Column 105, Line 16: "3,000-40,000" should be -- 3,000~10,000 --.

Signed and Sealed this
Second Day of June, 2020

Andrei Iancu
*Director of the United States Patent and Trademark Office*